US009540660B2

(12) United States Patent
Steigerwald

(10) Patent No.: US 9,540,660 B2
(45) Date of Patent: Jan. 10, 2017

(54) VECTOR COMPRISING MULTIPLE HOMOLOGOUS NUCLEOTIDE SEQUENCES

(71) Applicant: BAVARIAN NORDIC A/S, Kvistgaard (DK)

(72) Inventor: Robin Steigerwald, Munich (DE)

(73) Assignee: BAVARIAN NORDIC A/S, Kvistgaard (DK)

( * ) Notice: Subject to any disclaimer, the term of this patent is extended or adjusted under 35 U.S.C. 154(b) by 0 days.

(21) Appl. No.: 14/641,669

(22) Filed: Mar. 9, 2015

(65) Prior Publication Data
US 2016/0017369 A1    Jan. 21, 2016

Related U.S. Application Data

(63) Continuation of application No. 13/123,605, filed as application No. PCT/EP2009/008275 on Nov. 20, 2009, now Pat. No. 8,999,637.

(60) Provisional application No. 61/116,672, filed on Nov. 21, 2008.

(51) Int. Cl.
*C12N 15/86*    (2006.01)
(52) U.S. Cl.
CPC ..... *C12N 15/86* (2013.01); *C12N 2710/24134* (2013.01); *C12N 2710/24143* (2013.01); *C12N 2710/24151* (2013.01); *C12N 2740/11022* (2013.01); *C12N 2760/14122* (2013.01)
(58) Field of Classification Search
None
See application file for complete search history.

(56) References Cited

U.S. PATENT DOCUMENTS

| | | |
|---|---|---|
| 7,300,658 B2 | 11/2007 | Howley et al. |
| 7,338,662 B2 | 3/2008 | Howley et al. |
| 7,501,127 B2 | 3/2009 | Howley et al. |
| 7,550,147 B2 | 6/2009 | Howley et al. |
| 7,759,116 B2 | 7/2010 | Howley et al. |
| 2005/0244428 A1 | 11/2005 | Howley et al. |
| 2006/0165727 A1 | 7/2006 | Howley et al. |
| 2012/0121617 A1 | 5/2012 | Steigerwald et al. |

FOREIGN PATENT DOCUMENTS

| | | |
|---|---|---|
| WO | 90/12880 A1 | 11/1990 |
| WO | 03/097846 A1 | 11/2003 |

OTHER PUBLICATIONS

Antonis et al, Vaccination with recombinant modified vaccinia virus Ankara expressing bovine respiratory syncytial virus (bRSV) proteins protects calves against RSV challenge, Vaccine 25 (2007) 4818-4827.
Ball, High-Frequency Homologous Recombination in Vaccinia Virus DNA, Journal of Virology 61(6): (1987).
Chakrabarti et al, Intramolecular Recombination between Transfected Repeated Sequences in Mammalian cells Nonconservative, Molecular and Cellular Biology 6(7): 2520-2526 (1986).
Choi et al, Effects of Adeno-Associated Virus DNA Hairpin Structure on Recombination, Journal of Virology 6801-6807 (2005). q 79(11).
Dutch et al., Herpes Simplex Virus Type 1 Recombination: Role of DNA Replication and Viral a Sequences, Journal of Virology 66(1): 277-285 (1992).
Fuller et al, Helper Plasmids for Production of HIV-1-Derived Vectors, Human Gene Therapy 12: 2081-2093.
Gritz et al, Generation of Hybrid Genes and Proteins by Vaccinia Virus-Mediated Recombination: Application to Human Immunodeficiency Virus Type 1 env, Journal of Virology 64(12): 5948-5957 (1990).
Howley et al., A vaccinia virus transfer vector using a GUS reporter gene inserted into the 14L locus, Gene 172: 233-237 (1996).
Hruby et al., Assembly and analysis of a functional vaccinia virus "amplicon" containing the C-repeat region from the M protein of Streptococcus pyogenes, Proc. Natl. Acad. Sci. USA vol. 88, pp. 3190-3194, Apr. 1991.
Miller et al, Redesign of Retrovirus Packaging Cell Lines to Avoid Recombination Leading to Helper Virus Production, Molecular and Cellular Biology 6(8): 2895-2902 (1986).
Rubnitz et al., The Minimum Amount of Homology Required for Homologous Recombination in Mammalian Cells, Molecular and Cellular Biology 4(11): 2253-2258 (1984).
Zhang et al., Evidence for Retroviral Intramolecular Recombinations, Journal of Virology 75(14): 6348-6358 (2001).
European Patent Office, European Search Report, Appln. EP09003326.7, May 12, 2009.
International Searching Authority, International Search Report and Written Opinion, PCT/EP2009/008275, Apr. 14, 2010.
Zhao et al., Analysis of synonymous codon usage in 11 human bocavirus isolates, Biosystems 92(3):207-14 (2008) (Abstract only).
Wu et al., The FK520 gene cluster of *Streptomyces hygroscopicus* var. *ascomyceticus* (ATCC 14891) contains genes for biosynthesis of unusual polyketide extender units; Gene, vol. 251, pp. 81-90, 2000.
Genbank, kbA sequence; Genbank Accession No. Y10438.1; accessed Jan. 3, 2013.
Fuller et al., Helper plasmids for production of HIV-1-derived vectors, Human Gene Therapy, vol. 12, pp. 2081-2093, 2001.
USPTO, lalign output file amino acid alignment of fkbA 20-430 vs 1900-2320 created Mar. 13, 2013.
USPTO, lalign output file nucleic acid alignment of fkbA 60/1290 vs 5700-6960 created Mar. 13, 2013.
Rutigiano Identification of an H-2Db-restricted CD8+ cytotoxic T lymphocyte epitope in the matrix protein of respiratory syncytial virus; Virology, vol. 337, pp. 335-343, 2005.

(Continued)

*Primary Examiner* — Addison D Ault

(57) ABSTRACT

The invention relates to vectors comprising two or more homologous nucleotide sequences and methods for generating them. The invention concerns substituting bases in the homologous nucleotide sequences with different bases that do not alter the encoded amino acid sequence. The invention allows for the reduction of intramolecular recombination between homologous nucleotide sequences, in particular in mammalian cells. The invention further relates to nucleotide sequences containing substituted bases.

8 Claims, 32 Drawing Sheets

(56) References Cited

OTHER PUBLICATIONS

Ternette et al, Expression of RNA virus proteins by RNA polymerase II dependent expression plasmids is hindered at multiple steps; Virology Journal, vol. 4, No. 51, published Jun. 5, 2007, pp. 1-10.
Ternette et al, Immunogenicity and efficacy of codon optimized DNA vaccines encoding the F-protein of respiratory syncytial virus; Vaccine, vol. 25, pp. 7271-7279, 2007.
USPTO, Alignment, Applicant's Seq ID No. 1 vs Ternette codon-optimized RSV-F Genbank ID EF566942.1.

```
           Start F and F_trunc                                    50
F       (1)  ATGGATTGCCAATCCTCAAAACAAATGCAATTACCACAATCTTTGCTGC
F_trunc (1)  ATGGATCTCCCCATTCTCAAGACCAACGCCATCACCACCATCTTCGCCGC 51                                                  100
F       (51) AGTCACACTCTGTTTCGCTTCCAGTCAAAACATCACTGTAGAATTTTATC
F_trunc (51) CGTGACCCTGTGTTTCGCCAGCAGCCAGAACATCACCGTGGAGTTCTACC 101                                                 150
F      (101) AATCAACATGCAGTGCAGTTAGCAAAGGCTATCTTAGTGCTTTAAGAACT
F_trunc(101) AGAGCACCTGCAGCGCCGTGAGCAAGGGCTACCTGAGCGCCCTGAGGACC 151                                                 200
F      (151) GGTTGGTATACTAGTGTTATAACTATAGAATTAAGTAATATCAAGGAAAA
F_trunc(151) GGCTGGTACACCAGCGTGATCACCATCGAGCTGTCCAACATCAAAGAAAA 201                                                 250
F      (201) TAAGTGTAATGGAACAGACGCTAAGGTAAAATTGATAAAACAAGAATTAG
F_trunc(201) CAAGTGCAACGGCACCGACGCCAAAGTGAAGCTGATCAAGCAGGAACTGC 251                                                 300
F      (251) ATAAATATAAAAATGCTGTAACAGAATTGCAGTTGCTCATGCAAAGCACA
F_trunc(251) ACAAGTACAAGAACGCCGTGACCGAGCTGCAGCTGCTGATGCAGAGCACC 301                                                 350
F      (301) CCAGCAGCCAACAATCGGGCCAGAAGAGAACTACCAAGGTTTATGAATTA
F_trunc(301) CCTGCCGCCAACAACAGAGCCAGGCGCGAGCTGCCCCGGTTCATGAACTA 351
F      (351) TACACTCAACAATACCAAAAATAACAATGTAACATTAAGCAAGAAAAGGA
F_trunc(351) CACCCTGAACAACACCAAGAACAACAACGTGACCCTGAGCAAGAAGCGGA 401                                                 450
F      (401) AAACAAGATTTCTTGGCTTCTTGTTAGGTGTTGGATCTGCAATCGCCAGT
F_trunc(401) AGCGGCGGTTCCTGGGCTTTCTGCTGGGCGTGGGCAGCGCCATTGCCAGC primer A1
             451                 ------------------->            500
F      (451) GGCATTGCTGTATCTAAAGTCCTGCACCTAGAAGGGAAGTGAACAAAAT
F_trunc(451) GGCATTGCCGTGTCTAAGGTCCTGCATCTGGAAGGCGAGGTCAACAAGAT 501                                                 550
F      (501) CAAAAGTGCTTTACTATCCACAAACAAGGCTGTAGTCAGCTTATCAAATG
F_trunc(501) TAAGAGCGCCCTGCTGTCCACCAACAAGGCCGTGGTGTCCCTGAGCAACG 551                                                 600
F      (551) CAGTTAGTGTCTTAACCAGCAAAGTGTTAGACCTCAAAAACTATATAGAT
F_trunc(551) CCGTGAGCGTGCTGACCAGCAAGGTGCTGGATCTGAAGAACTACATCGAC 601                                                 650
F      (601) AAACAATTGTTACCCATTGTGAACAAGCAAAGCTGCAGCATATCAAACAT
F_trunc(601) AAGCAGCTGCTGCCCATCGTGAATAAGCAGTCCTGCAGCATCAGCAACAT
```

Figure 1

```
              651                                                    700
F      (651)  TGAAACTGTGATAGAATTCCAACAAAAGAGCAACAGACTACTAGAGATTA
Ftrunc (651)  CGAGACAGTGATCGAGTTCCACCAGAAGAGCAACCGGCTGCTGGAAATCA 701                                                    750
F      (701)  CCAGGGAATTTAGTGTTAATGCAGGTGTAACTACACCTGTAAGCACTTAT
Ftrunc (701)  CCCGGGAGTTCAGCGTGAATGCCGGCGTGACCACCCCGTGTCCACCTAC 751                                                    800
F      (751)  ATGTTAACAAATAGTGAATTATTATCATTAATCAATGATATGCCTATAAC
Ftrunc (751)  ATGCTGACCAACAGCGAGCTGCTGTCCCTGATCAATGACATGCCCATCAC 801                                                    850
F      (801)  AAATGATCAGAAAAAGTTAATGTCCAACAATGTTCAAATAGTTAGACAGC
Ftrunc (801)  CAACGACCAAAAGAAACTGATGAGCAACAACGTGCAGATCGTGCGGCAGC 851                                                    900
F      (851)  AAGTTACTCTATCATGTCCATAATAAAGGAGGAAGTCTTAGCATATGTA
Ftrunc (851)  AGAGCTACAGCATCATGAGCATCATCAAAGAAGAGGTGCTGGCCTACGTG 901                                                    950
F      (901)  GTACAATTACCACTATATGGTGTAATAGATACACCTTGTTGGAAACTACA
Ftrunc (901)  GTGCAGCTGCCCCTGTACGGCGTGATCGACACCCCTGCTGGAAGCTGCA 951                                                   1000
F      (951)  CACATCCCCTCTATGCACAACCAACACAAAGGAAGGGTCCAACATCTGTT
Ftrunc (951)  CACCAGCCCCCTGTGCACCACCAACACCAAAGAGGCGCAGCAACATCTGCC 1001                                                   1050
F     (1001)  TAACAAGAACCGACAGAGGATGGTACTGTGACAATGCAGGATCAGTGTCT
Ftrunc(1001)  TGACCCGGACCGATAGGGGCTGGTACTGCGACAACGCCGGCAGCGTGTCC 1051                                                   1100
F     (1051)  TTCTTCCCACAAGCTGAAACATGCAAAGTTCAATCGAATCGAGTATTTTG
Ftrunc(1051)  TTCTTTCCCCAAGCCGAGACTTGCAAGGTGCAGAGCAACAGGCTGTTCTG
                                    <------------------
                                         Primer B2
             1101                                                   1150
F     (1101)  TGACACAATGAACAGTTTAACATTACCAAGTGAAGTAAATCTCTGCAACA
Ftrunc(1101)  CGACACCATGAACAGCCTGACCCTGCCCAGCGAAGTGAACCTGTGCAACA 1151                                                   1200
F     (1151)  TTGACATATTCAACCCTAAATATGATTGCAAAATTATGACTTCAAAAACA
Ftrunc(1151)  TCGACATCTTTAACCCCAAGTACGACTGCAAGATCATGACCTCCAAGACC 1201                                                   1250
F     (1201)  GATGTAAGCAGCTCCGTTATCACATCTCTAGGAGCCATTGTGTCATGCTA
Ftrunc(1201)  GACGTGTCCAGCTCCGTGATTACCAGCCTGGGCGCCATCGTGTCCTGCTA 1251                                                   1300
F     (1251)  TGGCAAAACTAAATGTACAGCATCCAATAAAAATCGTGGAATCATAAAGA
Ftrunc(1251)  CGGCAAGACCAAGTGCACCGCCAGCAACAAGAACCGGGGCATCATCAAGA
```

Figure 1 (continued)

```
              1301                                              1350
F      (1301) CATTTTCTAACGGGTGTGATTATGTATCAAACAAGGGGGTGGACACTGTA
Ftrunc (1301) CCTTCAGCAACGGCTGCGACTACGTGTCCAATAAGGGCGTGGACACCGTG 1351                                              1400
F      (1351) TCTGTAGGTAATACGTTATATTATGTAAATAAGCAAGAAGGAAAAAGTCT
Ftrunc (1351) TCCGTGGGCAACACACTGTACTACGTGAACAAGCAGGAAGGCAAGAGCCT 1401                                              1450
F      (1401) CTATGTAAAAGGTGAACCAATAATAAATTTCTATGACCCATTAGTGTTCC
Ftrunc (1401) GTACGTGAAGGGCGAGCCCATCATCAACTTCTACGACCCCCTGGTGTTCC 1451                                              1500
F      (1451) CTTCTGATGAATTTGATGCATCAATATCTCAAGTCAATGAGAAGATTAAC
Ftrunc (1451) CCAGCGACGAGTTCGACGCCAGCATCAGCCAAGTGAACGAGAAGATCAAT 1501                                              1550
F      (1501) CAGAGCCTAGCATTTATTCGTAAATCCGATGAATTATTACATAATGTAAA
Ftrunc (1501) CAGTCCCTGGCCTTCATCAGGAAGAGCGACGAGCTGCTGCACAATGTGAA 1551                                              1600
F      (1551) TGTTGGTAAATCCACCACAAATATCATGATAACTACTATAATTATAGTGA
Ftrunc (1551) CGTGGGCAAGTCCACCACCAACTGA--------------------------
                                         stop Ftrunc
              1601                                              1650
F      (1601) TTATAGTAATATTGTTATTATTAATTGCAGTTGGGCTGTTCCTATACTGC
Ftrunc (1576) --------------------------------------------------

1651                                              1700
F      (1651) AAGGCCAGAAGCACACCAGTCACACTAAGCAAGGATCAACTGAGTGGTAT
Ftrunc (1576) --------------------------------------------------

1701           1725
F      (1701) AAATAATATTGCATTTAGTAACTGA    stop F
Ftrunc (1576) -------------------------
```

Figure 1 (continued)

```
BN_F-trunc optimized vs.BN_F full length
Score =  992 bits (2564),  Expect = 0.0,  Identities = 524/524 (100%),
Positives = 524/524 (100%), Gaps = 0/524 (0%)

F          1    MDLPILKTNAITTIFAAVTLCFASSQNITVEFYQSTCSAVSKGYLSALRTGWYTSVITIE    60
F_trunc    1    MDLPILKTNAITTIFAAVTLCFASSQNITVEFYQSTCSAVSKGYLSALRTGWYTSVITIE    60

F          61   LSNIKENKCNGTDAKVKLIKQELDKYKNAVTELQLLMQSTPAANNRARRELPREMNYTLN    120
F_trunc    61   LSNIKENKCNGTDAKVKLIKQELDKYKNAVTELQLLMQSTPAANNRARRELPREMNYTLN    120

F          121  NTKNNNVTLSKKRKRRFLGFLLGVGSAIASGIAVSKVLHLEGEVNKIKSALLSTNKAVVS    180
F_trunc    121  NTKNNNVTLSKKRKRRFLGFLLGVGSAIASGIAVSKVLHLEGEVNKIKSALLSTNKAVVS    180

F          181  LSNGVSVLTSKVLDLKNYIDKQLLPIVNKQSCSISNIETVIEFQQKSNRLLEITREFSVN    240
F_trunc    181  LSNGVSVLTSKVLDLKNYIDKQLLPIVNKQSCSISNIETVIEFQQKSNRLLEITREFSVN    240

F          241  AGVTTPVSTYMLTNSELLSLINDMPITNDQKKLMSNNVQIVRQQSYSIMSIIKEEVLAYV    300
F_trunc    241  AGVTTPVSTYMLTNSELLSLINDMPITNDQKKLMSNNVQIVRQQSYSIMSIIKEEVLAYV    300

F          301  VQLPLYGVIDTPCWKLHTSPLCTTNTKEGSNICLTRTDRGWYCDNAGSVSFFPQAETCKV    360
F_trunc    301  VQLPLYGVIDTPCWKLHTSPLCTTNTKEGSNICLTRTDRGWYCDNAGSVSFFPQAETCKV    360

F          361  QSNRVFCDTMNSLTLPSEVNLCNIDIFNPKYDCKIMTSKTDVSSSVITSLGAIVSCYGKT    420
F_trunc    361  QSNRVFCDTMNSLTLPSEVNLCNIDIFNPKYDCKIMTSKTDVSSSVITSLGAIVSCYGKT    420

F          421  KCTASNKNRGIIKTFSNGCDYVSNKGVDTVSVGNTLYYVNKQEGKSLYVKGEPIINFYDP    480
F_trunc    421  KCTASNKNRGIIKTFSNGCDYVSNKGVDTVSVGNTLYYVNKQEGKSLYVKGEPIINFYDP    480

F          481  LVFPSDEFDASISQVNEKINQSLAFIRKSDELLHNVNVGKSTTNIMITTIIVIIVILLI    540
F_trunc    481  LVFPSDEFDASISQVNEKINQSLAFIRKSDELLHNVNVGKSTTN-----    524

F          541  LIAVGLFLYCKARSTPVTLSKDQLSGINNIAFSN    574
F_trunc    541  ----------------------------------
```

```
                        1                                                50
EBOV-B non-opt    (1)   ATGGTTACATCAGGAATTCTACAATTGCCCCGTGAACGCTTCAGAAAAAC
EBOV-S non-opt    (1)   ATGGGGGGTCTTAGCCTACTCCAATTGCCCAGGGACAAATTTCGGAAAAG
                        51                                               100
EBOV-B non-opt    (51)  ATCATTTTTTGTTTGGGTAATAATCCTATTTCACAAAGTTTTCCCTATCC
EBOV-S non-opt    (51)  CTCTTTCTTTGTTTGGGTCATCATCTTATTCCAAAAGGCCTTTTCCATGC
                        101                                              150
EBOV-B non-opt    (101) CATTGGGCGTAGTTCACAACAACACTCTCCAGGTAAGTGATATAGATAAA
EBOV-S non-opt    (101) CTTTGGGTGTTGTGACTAACAGCACTTTAGAAGTAACAGAGATTGACCAG
                        151                                              200
EBOV-B non-opt    (151) TTGGTGTGCCGGGATAAACTTTCCTCCACAAGTCAGCTGAAATCGGTCGG
EBOV-S non-opt    (151) CTAGTCTGCAAGGATCATCTTGCATCTACTGACCAGCTGAAATCAGTTGG
                        201                                              250
EBOV-B non-opt    (201) GCTTAATCTAGAAGGTAATGGAGTTGCCACAGATGTACCAACAGCAACGA
EBOV-S non-opt    (201) TCTCAACCTCGAGGGGAGCGGAGTATCTACTGATATCCCATCTGCAACAA
                        251                                              300
EBOV-B non-opt    (251) AGAGATGGGGATTCCGAGCTGGTGTTCCACCCAAAGTGGTGAACTACGAA
EBOV-S non-opt    (251) AGCGTTGGGGCTTCAGATCTGGTGTTCCTCCCAAGGTGGTCAGCTATGAA
                        301                                              350
EBOV-B non-opt    (301) GCTGGGGAGTGGGCTGAAAACTGCTACAACCTGGACATCAAGAAAGCAGA
EBOV-S non-opt    (301) GCGGGAGAATGGGCTGAAAATTGCTACAATCTTGAAATAAAGAAGCCGGA
                        351                                              400
EBOV-B non-opt    (351) TGGTAGCGAATGCCTACCTGAAGCCCCTGAGGGTGTAAGAGGCTTCCCTC
EBOV-S non-opt    (351) CGGGAGCGAATGCTTACCCCCACCGCCAGATGGTGTCAGAGGCTTTCCAA
                        401                                              450
EBOV-B non-opt    (401) GCTGCCGTTATGTGCACAAGGTTTCTGGAACAGGGCCGTGCCCTGAAGGT
EBOV-S non-opt    (401) GGTGCCGCTATGTTCACAAAGCCCAAGGAACCGGGCCCTGCCCAGGTGAC
                        451                                              500
EBOV-B non-opt    (451) TACGCTTTCCACAAAGAAGGCGCTTTCTTCCTGTATGATCGACTGGCATC
EBOV-S non-opt    (451) TACGCCTTTCACAAGGATGGAGCTTTCTTCCTCTATGACAGGCTGGCTTC
                        501                                              550
EBOV-B non-opt    (501) AACAATCATCTATCGAAGCACCACGTTTTCAGAAGGTGTTGTGGCTTTCT
EBOV-S non-opt    (501) AACTGTAATTTACAGAGGAGTCAATTTTGCTGAGGGGGTAATTGCATTCT
                        551                                              600
EBOV-B non-opt    (551) TGATCCTCCCCGAAACTAAAAAGGACTTTTTCCAATCGCCACCACTACAT
EBOV-S non-opt    (551) TGATATTGGCTAAACCAAAAGAAACGTTCCTTCAGTCACCCCCCATTCGA
                        601                                              650
EBOV-B non-opt    (601) GAACCGGCCAATATGACAACAGACCCATCCAGCTACTACCACACAGTCAC
EBOV-S non-opt    (601) GAGGCAGTAAACTACACTGAAATACATCAAGTTATTATGCCACATCCTA
                        651                                              700
EBOV-B non-opt    (651) ACTTAATTATGTGGCTGACAATTTTGGGACCAATATGACTAACTTTCTGT
EBOV-S non-opt    (651) CTTGGAGTATGAAATCGAAAATTTTGGTGCTCAACACTCCACGACCCTTT
                        701                                              750
EBOV-B non-opt    (701) TTCAAGTGGATCATCTAACTTATGTGCAACTTGAACCAAGATTCACACCA
EBOV-S non-opt    (701) TCAAAATTGACAATAATACTTTTGTTCGTCTGGACAGGCCCCACACGCCT
                        751                                              800
EBOV-B non-opt    (751) CAATTTCTTGTCCAACTCAATGAGACCATTTATACTAATGGGCGTCGCAG
EBOV-S non-opt    (751) CAGTTCCTTTTCCAGCTGAATGATACCATTCACCTTCACCAACAGTTGAG
                        801                                              850
EBOV-B non-opt    (801) CAACACCACAGGAACACTAATTTGGAAAGTAAATCCTACTGTTGACACCG
EBOV-S non-opt    (801) TAATACAACTGGGACACTAATTTGGACACTAGATGCTAATATCAATGCTG
                        851                                              900
EBOV-B non-opt    (851) GCGTAGGTGAATGGGCCTTCTGGGAAAATAAGAAGAACTTCACAAAAACC
EBOV-S non-opt    (851) ATATTGGTGAATGGGCTTTTTGGGAAAATAAAAAAAATCTCTCCGAACAA
                        901                                              950
EBOV-B non-opt    (901) CTTTCAAGTGAAGAGCTGTCTGTCATATTTGTACCAAGAGCCCAGGATCC
EBOV-S non-opt    (901) CTACGTGGAGAAGAGCTGTCTTTCGAAGCTTTATCGCTCAACGAGACAGA
                        951                                              1000
EBOV-B non-opt    (951) AGGCAGCAACCAGAAGACGAAGGTCACTCCCACCAGCTTCGCCAACAACC
EBOV-S non-opt    (951) AGACGATGATGCGGCATCGTCGAGAATTACAAAGGGAAGAATCTCCGACC
```

Figure 9A

```
                            1001                                              1050
EBOV-B non-opt   (1001)  AAACCTCCAAGAACCACGAAGACTTGGTTCCAGAGGATCCCGCTTCAGTG
EBOV-S non-opt   (1001)  GGGCCACCAGGAAGTATTCGGACCTGGTTCCAAAGAATTCCCCTGGGATG
                            1051                                              1100
EBOV-B non-opt   (1051)  GTTCAAGTGCGAGACCTCCAGAGGGAAAACACAGTGCCGACCCCACCCCC
EBOV-S non-opt   (1051)  GTTCCATTGCACATACCAGAAGGGGAAACAACATTGCCGTCTCAGAATTC
                            1101                                              1150
EBOV-B non-opt   (1101)  AGACACAGTCCCCACAACTCTGATCCCCGACACAATGGAGGAACAAACCA
EBOV-S non-opt   (1101)  GACAGAAGGTCGAAGAGTAGGTGTGAACACTCAGGAGACCATTACAGAGA
                            1151                                              1200
EBOV-B non-opt   (1151)  CCAGCCACTACGAACCACCAAACATTTCCAGAAACCATCAAGAGAGGAAC
EBOV-S non-opt   (1151)  CAGCTGCAACAATTATAGGCACTAACGGCAACCATATGCAGATCTCCACC
                            1201                                              1250
EBOV-B non-opt   (1201)  AACACCGCACACCCCGAAACTCTCGCCAACAATCCCCCAGACAACACAAC
EBOV-S non-opt   (1201)  ATCGGGATAAGACCGAGCTCCAGCCAAATCCCGAGTTCCTCACCGACCAC
                            1251                                              1300
EBOV-B non-opt   (1251)  CCCGTCGACACCACCTCAAGACGGTGAGCGGACAAGTTCCCACACAACAC
EBOV-S non-opt   (1251)  GGCACCAAGCCCTGAGGCTCAGACCCCCACAACCCACACATCAGGTCCAT
                            1301                                              1350
EBOV-B non-opt   (1301)  CCTCCCCCCGCCCAGTCCCAACCAGCACAATCCATCCCACCACACGAGAG
EBOV-S non-opt   (1301)  CAGTGATGGCCACCGAGGAACCAACAACACCACCGGGAAGCTCCCCCGGC
                            1351                                              1400
EBOV-B non-opt   (1351)  ACTCACATTCCCACCACAATGACAACAAGCCATGACACCGACAGCAATCG
EBOV-S non-opt   (1351)  CCAACAACAGAAGCACCCACTCTCACCACCCCAGAAAATATAACAACAGC
                            1401                                              1450
EBOV-B non-opt   (1401)  ACCCAACCCAATTGACATCAGCGAGTCTACAGAGCCAGGACCACTCACCA
EBOV-S non-opt   (1401)  GGTTAAAACTGTCCTGCCACAGGAGTCCACAAGCAACGGTCTAATAACTT
                            1451                                              1500
EBOV-B non-opt   (1451)  ACACCACAAGAGGGGCTGCAAATCTGCTGACAGGCTCAAGAAGAACCCGA
EBOV-S non-opt   (1451)  CAACAGTAACAGGGATTCTTGGGAGTCTTGGGCTTCGAAAACGCAGCAGA
                            1501                                              1550
EBOV-B non-opt   (1501)  AGGGAAATCACCCTGAGAACACAAGCCAAATGCAACCCAAACCTACACTA
EBOV-S non-opt   (1501)  AGACAAACTAACACCAAAGCCACGGGTAAGTGCAATCCCAACTTACACTA
                            1551                                              1600
EBOV-B non-opt   (1551)  TTGGACAACCCAAGATGAAGGGGCTGCCATTGGTTTAGCCTGGATACCTT
EBOV-S non-opt   (1551)  CTGGACTGCACAAGAACAACATAATGCTGCTGGGATTGCCTGGATCCCGT
                            1601                                              1650
EBOV-B non-opt   (1601)  ACTTCGGGCCCGCAGCAGAGGGAATTTATACGGAAGGGATAATGCACAAT
EBOV-S non-opt   (1601)  ACTTTGGACCGGGTGCGGAAGGCATATACACTGAAGGCCTGATGCATAAC
                            1651                                              1700
EBOV-B non-opt   (1651)  CAAAATGGGCTAATTTGCGGGTTGAGGCAGCTAGCAAATGAGACGACTCA
EBOV-S non-opt   (1651)  CAAAATGCCTTAGTCTGTGGACTTAGGCAACTTGCAAATGAAACAACTCA
                            1701                                              1750
EBOV-B non-opt   (1701)  AGCCCTACAGTTATTCTTGCGTGCTACCACGGAATTGCGCACTTTCTCTA
EBOV-S non-opt   (1701)  AGCTCTGCAGCTTTTCTTAAGAGCCACAACGGAGCTGCGGACATATACCA
                            1751                                              1800
EBOV-B non-opt   (1751)  TATTGAATCGAAAAGCCATCGACTTTTTACTCCAAAGATGGGGAGGAACG
EBOV-S non-opt   (1751)  TACTCAATAGGAACGCCATAGATTTCCTTCTGCCACGATGGGCGGGACA
                            1801                                              1850
EBOV-B non-opt   (1801)  TGCCACATCTTAGGCCCAGATTGCTGTATTGAGCCCCATGATTGGACTAA
EBOV-S non-opt   (1801)  TGCAGGATCCTGGGACCAGATTGTTGCATTGAGCCACATGATTGGACAAA
                            1851                                              1900
EBOV-B non-opt   (1851)  GAACATTACTGACAAAATAGATCAAATCATTCATGATTTCATTGATAAAC
EBOV-S non-opt   (1851)  AAACATCACTGATAAAATCAACCAAATCATCCATGATTTCATCGACAACC
                            1901                                              1950
EBOV-B non-opt   (1901)  CTCTACCAGATCAAACAGATAATGACAATTGGTGGACAGGGTGGAGGCAA
EBOV-S non-opt   (1901)  CCTTACCTAATCAGGATAATGATGATAATTGGTGGACGGGCTGGAGACAG
                            1951                                              2000
EBOV-B non-opt   (1951)  TGGGTTCCTGCCGGGATCGGGATCACGGGGGTAATAATCGCAGTTATAGC
EBOV-S non-opt   (1951)  TGGATCCCTGCAGGAATAGGCATTACTGGAATTATTATTGCAATTATTGC
```

Figure 9A (continued)

```
                                 2001                    2031
EBOV-B non-opt      (2001) ACTGCTGTGTATTTGCAAATTTCTACTCTAA
EBOV-S non-opt      (2001) TCTTCTTTGCGTTTGCAAGCTGCTTTGCTGA 1                                                  50
EBOV-B non-opt       (1)   ATGGTTACATCAGGAATTCTACAATTGCCCCGTGAACGCTTCAGAAAAAC
EBOV-Z non-opt       (1)   ATGGGCGTTACAGGAATATTGCAGTTACCTCGTGATCGATTCAAGAGGAC
                                 51                                                 100
EBOV-B non-opt       (51)  ATCATTTTTTGTTTGGGTAATAATCCTATTTCACAAAGTTTTCCCTATCC
EBOV-Z non-opt       (51)  ATCATTCTTTCTTTGGGTAATTATCCTTTTCCAAAGAACATTTTCCATCC
                                 101                                                150
EBOV-B non-opt       (101) CATTGGGCGTAGTTCACAACAACACTCTCCAGGTAAGTGATATAGATAAA
EBOV-Z non-opt       (101) CACTTGGAGTCATCCACAATAGCACATTACAGGTTAGTGATGTCGACAAA
                                 151                                                200
EBOV-B non-opt       (151) TTGGTGTGCCGGGATAAACTTTCCTCCACAAGTCAGCTGAAATCGGTCGG
EBOV-Z non-opt       (151) CTAGTTTGTCGTGACAAACTGTCATCCACAAATCAATTGAGATCAGTTGG
                                 201                                                250
EBOV-B non-opt       (201) GCTTAATCTAGAAGGTAATGGAGTTGCCACAGATGTACCAACAGCAACGA
EBOV-Z non-opt       (201) ACTGAATCTCGAAGGGAATGGAGTGGCAACTGACGTGCCATCTGCAACTA
                                 251                                                300
EBOV-B non-opt       (251) AGAGATGGGGATTCCGAGCTGGTGTTCCACCCAAAGTGGTGAACTACGAA
EBOV-Z non-opt       (251) AAAGATGGGGCTTCAGGTCCGGTGTCCCACCAAAGGTGGTCAATTATGAA
                                 301                                                350
EBOV-B non-opt       (301) GCTGGGGAGTGGGCTGAAAACTGCTACAACCTGGACATCAAGAAAGCAGA
EBOV-Z non-opt       (301) GCTGGTGAATGGGCTGAAAACTGCTACAATCTTGAAATCAAAAAACCTGA
                                 351                                                400
EBOV-B non-opt       (351) TGGTAGCGAATGCCTACCTGAAGCCCCTGAGGGTGTAAGAGGCTTCCCTC
EBOV-Z non-opt       (351) CGGGAGTGAGTGTCTACCAGCAGCGCCAGACGGGATTCGGGGCTTCCCCC
                                 401                                                450
EBOV-B non-opt       (401) GCTGCCGTTATGTGCACAAGGTTTCTGGAACAGGGCCGTGCCCTGAAGGT
EBOV-Z non-opt       (401) GGTGCCGGTATGTGCACAAAGTATCAGGAACGGGACCGTGTGCCGGAGAC
                                 451                                                500
EBOV-B non-opt       (451) TACGCTTTCCACAAAGAAGGCGCTTTCTTCCTGTATGATCGACTGGCATC
EBOV-Z non-opt       (451) TTTGCCTTCCATAAAGAGGGTGCTTTCTTCCTGTATGATCGACTTGCTTC
                                 501                                                550
EBOV-B non-opt       (501) AACAATCATCTATCGAAGCACCACGTTTTCAGAAGGTGTTGTGGCTTTCT
EBOV-Z non-opt       (501) CACAGTTATCTACCGAGGAACGACTTTCGCTGAAGGTGTCGTTGCATTTC
                                 551                                                600
EBOV-B non-opt       (551) TGATCCTCCCCGAAACTAAAAAGGACTTTTTCCAATCGCCACCACTACAT
EBOV-Z non-opt       (551) TGATACTGCCCCAAGCTAAGAAGGACTTCTTCAGCTCACACCCCTTGAGA
                                 601                                                650
EBOV-B non-opt       (601) GAACCGGCCAATATGACAACAGACCCATCCAGCTACTACCACACAGTCAC
EBOV-Z non-opt       (601) GAGCCGGTCAATGCAACGGAGGACCCGTCTAGTGGCTACTATTCTACCAC
                                 651                                                700
EBOV-B non-opt       (651) ACTTAATTATGTGGCTGACAATTTTGGGACCAATATGACTAACTTTCTGT
EBOV-Z non-opt       (651) AATTAGATATCAGGCTACCGGTTTTGGAACCAATGAGACAGAGTACTTGT
                                 701                                                750
EBOV-B non-opt       (701) TTCAAGTGGATCATCTAACTTATGTGCAACTTGAACCAAGATTCACACCA
EBOV-Z non-opt       (701) TCGAGGTTGACAATTTGACCTACGTCCAACTTGAATCAAGATTCACACCA
                                 751                                                800
EBOV-B non-opt       (751) CAATTTCTTGTCCAACTCAATGAGACCATTTATACTAATGGGCGTCGCAG
EBOV-Z non-opt       (751) CAGTTTCTGCTCCAGCTGAATGAGACAATATATACAAGTGGGAAAAGGAG
                                 801                                                850
EBOV-B non-opt       (801) CAACACCACAGGAACACTAATTTGGAAAGTAAATCCTACTGTTGACACCG
EBOV-Z non-opt       (801) CAATACCACGGGAAAACTAATTTGGAAGGTCAACCCCGAAATTGATACAA
                                 851                                                900
EBOV-B non-opt       (851) GCGTAGGTGAATGGGCCTTCTGGGAAAATAAGAAGAACTTCACAAAAAACC
EBOV-Z non-opt       (851) CAATCGGGGAGTGGGCCTTCTGGGAAACTAAAAAAAACCTCACTAGAAAA
```

Figure 9A (continued)

```
                              901                                             950
EBOV-B non-opt         (901)  CTTTCAAGTGAAGAGCTGTCTGTCATATTTGTACCAAGAGCCCAGGATCC
EBOV-Z non-opt         (901)  ATTCGCAGTGAAGAGTTGTCTTTCACAGTTGTATCAAACGGAGCCAAAAA
                              951                                            1000
EBOV-B non-opt         (951)  AGGCAGCAACCAGAAGACGAAGGTCACTCCCACCAGCTTCGCCAACAACC
EBOV-Z non-opt         (951)  CATCAGTGGTCAGAGTCCGGCGCGAACTTCTTCCGACCCAGGGACCAACA
                              1001                                           1050
EBOV-B non-opt        (1001)  AAACCTCCAAGAACCACGAAGACTTGGTTCCAGAGGATCCCGCTTCAGTG
EBOV-Z non-opt        (1001)  CAACAACTGAAGACCACAAAATCATGGCTTCAGAAAATTCCTCTGCAATG
                              1051                                           1100
EBOV-B non-opt        (1051)  GTTCAAGTGCGAGACCTCCAGAGGGAAAACACAGTGCCGACCCCACCCCC
EBOV-Z non-opt        (1051)  GTTCAAGTGCACAGTCAAGGAAGGGAAGCTGCAGTGTCGCATCTAACAAC
                              1101                                           1150
EBOV-B non-opt        (1101)  AGACACAGTCCCCACAACTCTGATCCCCGACACAATGGAGGAACAAACCA
EBOV-Z non-opt        (1101)  CCTTGCCACAATCTCCACGAGTCCCCAATCCCTCACAACCAAACCAGGTC
                              1151                                           1200
EBOV-B non-opt        (1151)  CCAGCCACTACGAACCACCAAACATTTCCAGAAACCATCAAGAGAGGAAC
EBOV-Z non-opt        (1151)  CGGACAACAGCACCCATAATACACCCGTGTATAAACTTGACATCTCTGAG
                              1201                                           1250
EBOV-B non-opt        (1201)  AACACCGCACACCCCGAAACTCTCGCCAACAATCCCCCAGACAACACAAC
EBOV-Z non-opt        (1201)  GCAACTCAAGTTGAACAACATCACCGCAGAACAGACAACGACAGCACAGC
                              1251                                           1300
EBOV-B non-opt        (1251)  CCCGTCGACACCACCTCAAGACGGTGAGCGGACAAGTTCCCACACAACAC
EBOV-Z non-opt        (1251)  CTCCGACACTCCCTCTGCCACGACCGCAGCCGGACCCCCAAAAGCAGAGA
                              1301                                           1350
EBOV-B non-opt        (1301)  CCTCCCCCCGCCCAGTCCCAACCAGCACAATCCATCCCACCACACGAGAG
EBOV-Z non-opt        (1301)  ACACCAACACGAGCAAGAGCACTGACTTCCTGGACCCCGCCACCACAACA
                              1351                                           1400
EBOV-B non-opt        (1351)  ACTCACATTCCCACCACAATGACAACAAGCCATGACACCGACAGCAATCG
EBOV-Z non-opt        (1351)  AGTCCCCAAAACCACAGCGAGACCGCTGGCAACAACAACACTCATCACCA
                              1401                                           1450
EBOV-B non-opt        (1401)  ACCCAACCCAATTGACATCAGCGAGTCTACAGAGCCAGGACCACTCACCA
EBOV-Z non-opt        (1401)  AGATACCGGAGAAGAGAGTGCCAGCAGCGGGAAGCTAGGCTTAATTACCA
                              1451                                           1500
EBOV-B non-opt        (1451)  ACACCACAAGAGGGGCTGCAAATCTGCTGACAGGCTCAAGAAGAACCCGA
EBOV-Z non-opt        (1451)  ATACTATTGCTGGAGTCGCAGGACTGATCACAGGCGGGAGAAGAACTCGA
                              1501                                           1550
EBOV-B non-opt        (1501)  AGGGAAATCACCCTGAGAACACAAGCCAAATGCAACCCAAACCTACACTA
EBOV-Z non-opt        (1501)  AGAGAAGCAATTGTCAATGCTCAACCCAAATGCAACCCTAATTTACATTA
                              1551                                           1600
EBOV-B non-opt        (1551)  TTGGACAACCCAAGATGAAGGGGCTGCCATTGGTTTAGCCTGGATACCTT
EBOV-Z non-opt        (1551)  CTGGACTACTCAGGATGAAGGTGCTGCAATCGGACTCGCCTGGATACCAT
                              1601                                           1650
EBOV-B non-opt        (1601)  ACTTCGGGCCCGCAGCAGAGGGAATTTATACGGAAGGGATAATGCACAAT
EBOV-Z non-opt        (1601)  ATTTCGGGCCAGCAGCCGAGGGAATTTACATAGAGGGGCTAATGCACAAT
                              1651                                           1700
EBOV-B non-opt        (1651)  CAAAATGGGCTAATTTGCGGGTTGAGGCAGCTAGCAAATGAGACGACTCA
EBOV-Z non-opt        (1651)  CAAGATGGTTTAATCTGTGGGTTGAGACAGCTGGCCAACGAGACGACTCA
                              1701                                           1750
EBOV-B non-opt        (1701)  AGCCCTACAGTTATTCTTGCGTGCTACCACGGAATTGCGCACTTTCTCTA
EBOV-Z non-opt        (1701)  AGCTCTTCAACTGTTCCTGAGAGCCACAACTGAGCTACGCACCTTTTCAA
                              1751                                           1800
EBOV-B non-opt        (1751)  TATTGAATCGAAAAGCCATCGACTTTTTACTCCAAAGATGGGGAGGAACG
EBOV-Z non-opt        (1751)  TCCTCAACCGTAAGGCAATTGATTTCTTGCTGCAGCGATGGGGCGGCACA
                              1801                                           1850
EBOV-B non-opt        (1801)  TGCCACATCTTAGGCCCAGATTGCTGTATTGAGCCCCATGATTGGACTAA
EBOV-Z non-opt        (1801)  TGCCACATTCTGGGACCGGACTGCTGTATCGAACCACATGATTGGACCAA
```

Figure 9A (continued)

```
                                    1851                                1900
EBOV-B non-opt      (1851) GAACATTACTGACAAAATAGATCAAATCATTCATGATTTCATTGATAAAC
EBOV-Z non-opt      (1851) GAACATAACAGACAAAATTGATCAGATTATTCATGATTTTGTTGATAAAA
                                    1901                                1950
EBOV-B non-opt      (1901) CTCTACCAGATCAAACAGATAATGACAATTGGTGGACAGGGTGGAGGCAA
EBOV-Z non-opt      (1901) CCCTTCCGGACCAGGGGGACAATGACAATTGGTGGACAGGATGGAGACAA
                                    1951                                2000
EBOV-B non-opt      (1951) TGGGTTCCTGCCGGGATCGGGATACACGGGGGTAATAATCGCAGTTATAGC
EBOV-Z non-opt      (1951) TGGATACCGGCAGGTATTGGAGTTACAGGCGTTATAATTGCAGTTATCGC
                                    2001            2031
EBOV-B non-opt      (2001) ACTGCTGTGTATTTGCAAATTTCTACTCTAA
EBOV-Z non-opt      (2001) TTTATTCTGTATATGCAAATTTGTCTTTTAG 1                                   50
EBOV-S non-opt         (1) ATGGGGGGTCTTAGCCTACTCCAATTGCCCAGGGACAAATTTCGGAAAAG
EBOV-Z non-opt         (1) ATGGGCGTTACAGGAATATTGCAGTTACCTCGTGATCGATTCAAGAGGAC
                                    51                                  100
EBOV-S non-opt        (51) CTCTTTCTTTGTTTGGGTCATCATCTTATTCCAAAAGGCCTTTTCCATGC
EBOV-Z non-opt        (51) ATCATTCTTTCTTTGGGTAATTATCCTTTTCCAAAGAACATTTTCCATCC
                                    101                                 150
EBOV-S non-opt       (101) CTTTGGGTGTTGTGACTAACAGCACTTTAGAAGTAACAGAGATTGACCAG
EBOV-Z non-opt       (101) CACTTGGAGTCATCCACAATAGCACATTACAGGTTAGTGATGTCGACAAA
                                    151                                 200
EBOV-S non-opt       (151) CTAGTCTGCAAGGATCATCTTGCATCTACTGACCAGCTGAAATCAGTTGG
EBOV-Z non-opt       (151) CTAGTTTGTCGTGACAAACTGTCATCCACAAATCAATTGACATCAGTTGG
                                    201                                 250
EBOV-S non-opt       (201) TCTCAACCTCGAGGGGAGCGGAGTATCTACTGATATCCCATCTGCAACAA
EBOV-Z non-opt       (201) ACTGAATCTCGAAGGGAATGGAGTGGCAACTGACGTGCCATCTGCAACTA
                                    251                                 300
EBOV-S non-opt       (251) AGCGTTGGGGCTTCAGATCTGGTGTTCCTCCCAAGGTGGTCAGCTATGAA
EBOV-Z non-opt       (251) AAAGATGGGGCTTCAGGTCCGGTGTCCCACCAAAGGTGGTCAATTATGAA
                                    301                                 350
EBOV-S non-opt       (301) GCGGGAGAATGGGCTGAAAATTGCTACAATCTTGAAATAAAGAAGCCGGA
EBOV-Z non-opt       (301) GCTGGTGAATGGGCTGAAAACTGCTACAATCTTGAAATCAAAAAACCTGA
                                    351                                 400
EBOV-S non-opt       (351) CGGGAGCGAATGCTTACCCCCACCGCCAGATGGTGTCAGAGGCTTTCCAA
EBOV-Z non-opt       (351) CGGGAGTGAGTGTCTACCAGCAGCGCCAGACGGGATTCGGGGCTTCCCCC
                                    401                                 450
EBOV-S non-opt       (401) GGTGCCGCTATGTTCACAAAGCCCAAGGAACCGGGCCCTGCCCAGGTGAC
EBOV-Z non-opt       (401) GGTGCCGGTATGTGCACAAAGTATCAGGAACGGGACCGTGTGCCGGAGAC
                                    451                                 500
EBOV-S non-opt       (451) TACGCCTTTCACAAGGATGGAGCTTTCTTCCTCTATGACAGGCTGGCTTC
EBOV-Z non-opt       (451) TTTGCCTTCCATAAAGAGGGTGCTTTCTTCCTGTATGATCGACTTGCTTC
                                    501                                 550
EBOV-S non-opt       (501) AACTGTAATTTACAGAGGAGTCAATTTTGCTGAGGGGGTAATTGCATTCT
EBOV-Z non-opt       (501) CACAGTTATCTACCGAGGAACGACTTTCGCTGAAGGTGTCGTTGCATTTC
                                    551                                 600
EBOV-S non-opt       (551) TGATATTGGCTAAACCAAAAGAAACGTTCCTTCAGTCACCCCCCATTCGA
EBOV-Z non-opt       (551) TGATACTGCCCCAAGCTAAGAAGGACTTCTTCAGCTCACACCCCTTGAGA
                                    601                                 650
EBOV-S non-opt       (601) GAGGCAGTAAACTACACTGAAAATACATCAAGTTATTATGCCACATCCTA
EBOV-Z non-opt       (601) GAGCCGGTCAATGCAACGGAGGACCCGTCTAGTGGCTACTATTCTACCAC
                                    651                                 700
EBOV-S non-opt       (651) CTTGGAGTATGAAATCGAAATTTTGGTGCTCAACACTCCACGACCCTTT
EBOV-Z non-opt       (651) AATTAGATATCAGGCTACCGGTTTTGGAACCAATGAGACAGAGTACTTGT
                                    701                                 750
EBOV-S non-opt       (701) TCAAAATTGACAATAATACTTTTGTTCGTCTGGACAGGCCCCACACGCCT
EBOV-Z non-opt       (701) TCGAGGTTGACAATTTGACCTACGTCCAACTTGAATCAAGATTCACACCA
```

Figure 9A (continued)

```
                         751                                                800
EBOV-S non-opt    (751)  ░░░░░░TTT░░░░░░░░░░░░T░C░░TC░CCTTCACCAAC░GTT░░░
EBOV-Z non-opt    (751)  ░░░░T░░GC░░░░░░░░░G░░░░A░░ATA░TACAAGTGGGA░AAGG░░
                         801                                                850
EBOV-S non-opt    (801)  T░░T░░A░T░░GA░A░T░░T░░ACAC░AGA░GT░T░T░CA░TG░TG
EBOV-Z non-opt    (801)  C░░T░C░░G░░A░A░T░░T░░AGG░CA░CC░CG░A░TG░T░CAA
                         851                                                900
EBOV-S non-opt    (851)  AT░TT░░T░AA░TGG░T░░TT░░CAA░A░AA░A░A░ATCTCT░CGA░C░░
EBOV-Z non-opt    (851)  CA░TC░░G░A░GTGG░░C░TTC░GG░AAA░C░AA░AA░A░CCT░AGTAG░AA░
                         901                                                950
EBOV-S non-opt    (901)  C░A░TG░A░░A░GA░C░TC░TT░░GA░GC░TT░░░GCT░AAC░AG░C░AG░
EBOV-Z non-opt    (901)  A░T░CAGT░GA░A░T░░TC░TT░CAC░GT░GT░AA░AAA░GGA░CC░A░A░
                         951                                               1000
EBOV-S non-opt    (951)  AGA░GA░GA░TGC░GGCAT░GT░GA░G░AT░TA░AAAG░GAAG░ATCT░░G░C░
EBOV-Z non-opt    (951)  CAT░AG░░GT░CA░AGTC░GC░GC░CAAC░TT░TTCC░ACCC░GGGAC░A░GA
                         1001                                              1050
EBOV-S non-opt   (1001)  GGG░C░░CAGGA░GTATTCGGA░C░░GT░C░AAG░A░TTC░CT░GGA░░
EBOV-Z non-opt   (1001)  CAA░A░TGAAG░CC░CAAAAT░A░TC░CT░C░A░A░TTC░T░C░CA░░░
                         1051                                              1100
EBOV-S non-opt   (1051)  ░░░░C░TT░G░C░░TA░C░G░A░G░░░A░AA░A░TT░CC░TC░AC░ATT░
EBOV-Z non-opt   (1051)  ░░░CA░GT░CAC░AGT░C░AAGG░A░G░C░AAG░TGC░AG░TT░CA░TA░CAA░
                         1101                                              1150
EBOV-S non-opt   (1101)  GACA░AAGGTCGAAGAGTAGG░░GTGA░CA░T░AGGAG░░░ATTA░░GAGA
EBOV-Z non-opt   (1101)  CCTT░CCACAATCTCCACGA░T░CCCC░AT░C░TCACA░CC░AAAC░░GGTC
                         1151                                              1200
EBOV-S non-opt   (1151)  ░A░CTGCA░CA░TTATAGGC░░TAA░░GCA░CC░TA░GC░GA░T░░CACC
EBOV-Z non-opt   (1151)  ░G░ACAAC░GC░CCCATAATA░ACC░░TGT░TA░AC░TG░C░T░░TGAG
                         1201                                              1250
EBOV-S non-opt   (1201)  ATCGGGAT░AGACCGAGCTCCAG░░AA░TCC░GAGTTC░TCACCG░░CA░
EBOV-Z non-opt   (1201)  GCAACTCA░GTTGAACAACATCA░GC░GAA░AGACAAGGACAGC░░AG░
                         1251                                              1300
EBOV-S non-opt   (1251)  GG░ACCA░GC░░TGAG░░TCA░░CC░C░CA░AACC░A░AC░ATC░░GTCCAT
EBOV-Z non-opt   (1251)  CT░CGAC░CT░░CTCT░░CAC░A░CG░AG░CGGA░C░CC░AAA░░CAGAGA
                         1301                                              1350
EBOV-S non-opt   (1301)  CAGTGA░TGG░░C░AC░░GA░░GAAC░AACAACA░CACCGGGAAG░T░░C░C░GGC
EBOV-Z non-opt   (1301)  ACACC░ACA░G░G░A░AGCA░TGACTTC░TGGACCCCGC░A░GA░AACA
                         1351                                              1400
EBOV-S non-opt   (1351)  CCAA░AAC░AG░AGCACC░ACTCT░A░CAC░CCAG░A░TA░TAACAACAGC
EBOV-Z non-opt   (1351)  AGTC░CCA░A░CCACAG░GAGAC░G░TGG░AACA░CA░C░CTCATCACCA
                         1401                                              1450
EBOV-S non-opt   (1401)  G░T░AAACT░TCCT░CCACAGGAGTC░ACA░GCAAC░GTC░░A░T░T
EBOV-Z non-opt   (1401)  A░A░CCGGA░AAGA░AGTGCCAGCAG░GGG░AGCTA░GCT░░A░T░CA
                         1451                                              1500
EBOV-S non-opt   (1451)  CA░AG░TAA░A░GGA░TCTT░GGAGTC░TGGGCTTC░AAAAC░C░AGCA░░
EBOV-Z non-opt   (1451)  AT░░TA░TG░T░GA░G░CGCA░GACTGA░CACAGGCGG░G░G░A░CTC░░
                         1501                                              1550
EBOV-S non-opt   (1501)  ░░░C░AA░T░AACAC░░AA░G░CACGGGT░AG░T░░A░TTC░AAC░TT░AC░░
EBOV-Z non-opt   (1501)  ░░░G░AG░C░A░TTGT░A░T░CTCAACCC░AA░T░CA░CC░TAA░TT░A░T░░
                         1551                                              1600
EBOV-S non-opt   (1551)  ░░░░░░░G░A░░AG░A░AC░░CA░AA░G░TGCT░░GA░T░░░G░░A░C░░G░
EBOV-Z non-opt   (1551)  ░░░░░░░A░T░AG░░TGA░GG░GC░T░░AATC░AC░TG░C░TG░░TA░░G░
                         1601                                              1650
EBOV-S non-opt   (1601)  AC░TT░░A░G░GGT░CG░░AG░CATA░CACT░A░GC░CT░GA░TC░TA░C
EBOV-Z non-opt   (1601)  A░TT░CG░CC░A░CA░C░AG░░A░TT░ACATA░GGG░GT░A░TG░CA░T
                         1651                                              1700
EBOV-S non-opt   (1651)  ░A░AT░CCT░AGT░T░T░GAC░T░AGG░A░T░CA░ATG░A░░A░CTC░
EBOV-Z non-opt   (1651)  ░AAGA░GT░TT░AT░T░T░GGT░GA░A░AG░T░GG░AA░AG░AG░TCA
                         1701                                              1750
EBOV-S non-opt   (1701)  ░░░░░C░░G░GC░TTT░░T░A░░░CAC░░AG░GC░░░GG░GA░A░A░G░C░
EBOV-Z non-opt   (1701)  ░GCT░░T░AT░GT░TC░C░GA░A░CC░ACA░C░T░░G░TACGCA░C░T░T░T░AA
```

Figure 9A (continued)

```
                    1751                                                  1800
EBOV-S non-opt (1751) AACTCAATAGGAAGGCCATAGATTTCCTTCGGACGATGGGCGGGACA
EBOV-Z non-opt (1751) CCTCAACCGTAAGGCAATTCATTTCTTGCTGCAGCGATGGGCGGCACA
                    1801                                                  1850
EBOV-S non-opt (1801) TGCAGGATCCTGGGACCAGATTGTTGCATTGAGCCACATGATGGACAAA
EBOV-Z non-opt (1801) TGCCACATTCTGGGACCGGACTGCTGTATCGACCACATGATGGACCAA
                    1851                                                  1900
EBOV-S non-opt (1851) AAACATCACTGATAAAATCAACAAAACATCGATGATTTCATCGACAACC
EBOV-Z non-opt (1851) GAACATAACAGACAAAATTGATCAGATTATTCATGATTTGTTGATAAAA
                    1901                                                  1950
EBOV-S non-opt (1901) CCTAACTAATCAGGATAATGATGATAATTGTTGCAGGGGCTGGAGACAG
EBOV-Z non-opt (1901) CCTTCGGACCAGGGGGACAATGACAATTGTTGCACAGGATGGAGACAA
                    1951                                                  2000
EBOV-S non-opt (1951) TGGATCCCTTGCAGGAATAAGCATTACTGGAATTATTATTGGAATTATTGG
EBOV-Z non-opt (1951) TGGATACCGGCAGGTATTGGAGTTACAGGCGTTAATTGCAGTTATCGG
                    2001           2031
EBOV-S non-opt (2001) ACTTCTTTCGTTTGCAAGCTGCTTGCTGA
EBOV-Z non-opt (2001) TTTATTCTTATAATGCAAATTGTCTTTAG
```

Figure 9A (continued)

```
                          1                                               50
EBOV-B opt      (1)   ATGGTCACATCTGGAATTCTCCAGCTCCCTAGGGAACGGTTCCGGAAAAC
EBOV-S opt      (1)   ATGGGCGGCCTGAGCCTGCTGCAGCTGCCCCGGGACAAGTTCCGGAAGTC
                          51                                              100
EBOV-B opt     (51)   CAGTTTCTTTGTCTGGGTCATCATCCTCTTCCATAAGGTGTTCCCTATCC
EBOV-S opt     (51)   CAGCTTCTTCGTGTGGGTGATCATCCTGTTCCAGAAAGCCTTCAGCATGC
                          101                                             150
EBOV-B opt    (101)   CCCTGGGGGTCGTCCATAACAATACATTGCAAGTGTCAGATATCGATAAG
EBOV-S opt    (101)   CCCTGGGCGTGGTGACCAACAGCACCCTGGAAGTGACCGAGATCGACCAG
                          151                                             200
EBOV-B opt    (151)   TTGGTGTGTCGCGATAAACTGTCATCTACCTCTCAGCTGAAAAGCGTCGG
EBOV-S opt    (151)   CTGGTGTGCAAGGACCACCTGGCCAGCACCGATCAGCTGAAGTCCGTGGG
                          201                                             250
EBOV-B opt    (201)   CCTCAACCTCGAAGGGAATGGTGTCGCCACTGATGTCCCTACTGCCACAA
EBOV-S opt    (201)   CCTGAACCTGGAAGGCAGCGGCGTGAGCACCGACATCCCCAGCGCCACCA
                          251                                             300
EBOV-B opt    (251)   AACGATGGGGTTTCCGGGCTGGTGTCCCCCCAAAAGTGGTCAACTATGAA
EBOV-S opt    (251)   AGAGATGGGGCTTCAGATCCGGCGTGCCCCCCAAGGTGGTGTCTTATGAG
                          301                                             350
EBOV-B opt    (301)   GCTGGCGAATGGGCAGAGAATTGCTATAATCTGGACATTAAAAAGGCCGA
EBOV-S opt    (301)   GCCGGCGAGTGGGCCGAGAACTGCTACAACCTGGAAATCAAGAAGCCCGA
                          351                                             400
EBOV-B opt    (351)   TGGCTCCGAGTGTCTCCCTGAAGCTCCTGAGGGCGTGCGGGGATTCCCAA
EBOV-S opt    (351)   CGGCAGCGAGTGTCTGCCTCCCCCTCCCGATGGCGTGAGAGGCTTCCCCC
                          401                                             450
EBOV-B opt    (401)   GATGTCGCTACGTCCATAAAGTGTCTGGCACCGGCCCTTGCCCTGAAGGA
EBOV-S opt    (401)   GGTGCAGATACGTGCACAAGGCACAAGGCACCGGTCCATGCCCAGGCGAC
                          451                                             500
EBOV-B opt    (451)   TACGCCTTTCATAAAGAAGGGGCCTTTTTCCTCTATGATCGCCTGGCTTC
EBOV-S opt    (451)   TACGCCTTCCACAAGGACGGCGCCTTTTTCCTGTACGACCGGCTGGCCTC
                          501                                             550
EBOV-B opt    (501)   CACAATTATCTATCGCTCTACTACCTTTTCCGAGGGGGTGGTCGCTTTTC
EBOV-S opt    (501)   CACCGTGATCTACCGGGGCGTGAACTTTGCCGAGGGCGTGATCGCCTTCC
                          551                                             600
EBOV-B opt    (551)   TCATCCTCCCCGAGACAAAGAAAGATTTCTTTCAGAGTCCCCCCCTGCAT
EBOV-S opt    (551)   TGATCCTGGCCAAGCCCAAAGAGACATTCCTGCAGAGCCCCCCCATCCGG
                          601                                             650
EBOV-B opt    (601)   GAGCCTGCCAATATGACTACCGATCCTTCCTCTTACTATCATACCGTGAC
EBOV-S opt    (601)   GAGGCCGTGAACTACACCGAGAACACCAGCAGCTACTACGCCACCTCCTA
                          651                                             700
EBOV-B opt    (651)   ACTCAATTATGTCGCTGATAACTTCGGCACTAACATGACCAACTTTCTGT
EBOV-S opt    (651)   CCTGGAATACGAGATCGAGAACTTCGGCGCCCAGCACAGCACCACCCTGT
                          701                                             750
EBOV-B opt    (701)   TCCAGGTCGACCACCTGACATATGTCCAGCTCGAGCCTCGCTTTACCCCA
EBOV-S opt    (701)   TCAAGATCGACAACAACACCTTCGTGCGGCTGGACAGACCCCACACCCCC
                          751                                             800
EBOV-B opt    (751)   CAGTTCCTGGTCCAGCTCAATGAAACTATCTATACTAACGGACGGCGCTC
EBOV-S opt    (751)   CAGTTTCTGTTCCAGCTGAACGACACCATCCATCTGCATCAGCAGCTGTC
                          801                                             850
EBOV-B opt    (801)   TAATACCACCGGGACCCTCATTTGGAAAGTCAATCCCACTGTCGATACCG
EBOV-S opt    (801)   CAACACCACCGGCAGACTGATCTGGACCCTGGACGCCAACATCAACGCCG
                          851                                             900
EBOV-B opt    (851)   GCGTCGGAGAGTGGGCCTTTTGGGAAAACAAGAAGAACTTTACCAAGACC
EBOV-S opt    (851)   ACATCGGTGAATGGGCTTTTTGGGAGAACAAGAAGAATCTGAGCGAGCAG
                          901                                             950
EBOV-B opt    (901)   CTGAGTAGCGAGGAACTCTCTGTGATCTTTGTGCCTCGCGCTCAGGATCC
EBOV-S opt    (901)   CTGCGGGGCGAAGAACTCAGCTTCGAGGCCCTGAGCCTGAACGAGACAGA
                          951                                             1000
EBOV-B opt    (951)   TGGATCCAACCAGAAAACCAAAGTGACACCTACATCTTTTGCCAACAACC
EBOV-S opt    (951)   GGACGACGACGCCGCCAGCAGCGGATCACCAAGGGCCGGATCAGCGACC
                          1001                                            1050
EBOV-B opt   (1001)   AGACAAGCAAGAACCATGAGGACCTCGTCCCCGAAGATCCTGCCTCTGTG
EBOV-S opt   (1001)   GGGCCACCAGAAAGTACAGCGACCTGGTGCCCAAGAACAGCCCCGGCATG
```

Figure 9B

```
              1051                                           1100
EBOV-B opt  (1051) GTCCAGGTCCGGGACCTCCAGCGCGAAAATACCGTGCCTACTCCCCCCCC
EBOV-S opt  (1051) GTGCCTCTGCACATCCCCGAGGGCGAGACAACTCTCCCTAGTCAGAATAG
              1101                                           1150
EBOV-B opt  (1101) TGATACCGTCCCTACTACCCTCATTCCCGATACAATGGAAGAACAGACCA
EBOV-S opt  (1101) CACCGAGGGCAGACGCGTGGGCGTGAACACCCAGGAAACCATCACCGAGA
              1151                                           1200
EBOV-B opt  (1151) CCTCTCATTACGAGCCACCTAACATCTCCAGAAATCACCAGGAACGAAAT
EBOV-S opt  (1151) CAGCCGCCACCATCATTGGTACTAACGGCAACCACATGCAGATCAGCACC
              1201                                           1250
EBOV-B opt  (1201) AACACCGCTCATCCCGAGACTCTGGCTAATAACCCCCCCGACAATACTAC
EBOV-S opt  (1201) ATCGGCATCCGGCCCAGCAGCAGCCAGATCCCAAGTAGTAGTCCTACCAC
              1251                                           1300
EBOV-B opt  (1251) CCCTAGTACCCCCCCTCAGGACGGGGAGAGAACCAGTTCCCATACTACAC
EBOV-S opt  (1251) AGCCCCTAGCCCTGAGGCCCAGACCCCTACCACACACCAGCGGCCCTA
              1301                                           1350
EBOV-B opt  (1301) CCTCCCCAAGACCCGTCCCTACATCTACCATTCATCCCACCACCCGCGAG
EBOV-S opt  (1301) GCGTGATGGCCACCGAGGAACCTACCACCCCTCCTGGCAGCAGCCCAGGT
              1351                                           1400
EBOV-B opt  (1351) ACACACATTCCTACCACTATGACCACATCCCATGACACCGATTCCAATCG
EBOV-S opt  (1351) CCAACTACCGAGGCACCAACCCTGACCACCCCCGAGAACATCACCACCGC
              1401                                           1450
EBOV-B opt  (1401) CCCTAACCCCATCGATATCAGCGAATCTACCGAGCCCGGACCCCTCACAA
EBOV-S opt  (1401) CGTGAAAACCGTGCTGCCCCAGGAAAGCACCAGCAACGGCCTGATCACCA
              1451                                           1500
EBOV-B opt  (1451) ATACAACCCGCGGAGCCGCTAATCTGCTGACTGGCTCCCGGCGCACTCGA
EBOV-S opt  (1451) GCACCGTGACCGGCATCCTGGGCAGCCTGGGCCTGCGGAAGCGGAGCAGA
              1501                                           1550
EBOV-B opt  (1501) AGAGAAATCACCCTGCGAACACAGGCCAAGTGTAACCCAAACCTCCATTA
EBOV-S opt  (1501) CGGCAGACCAACACCAAGGCCACCGGCAAGTGCAACCCCAACCTGCACTA
              1551                                           1600
EBOV-B opt  (1551) TTGGACAACCCAGGATGAAGGGGCCGCTATTGGCCTCGCTTGGATCCCTT
EBOV-S opt  (1551) CTGGACCGCCCAGGAACAGCACAACGCCGCTGGGATCGCCTGGATCCCCT
              1601                                           1650
EBOV-B opt  (1601) ATTTCGGGCCTGCAGCCGAGGGGATCTATACCGAAGGTATAATGCATAAT
EBOV-S opt  (1601) ACTTTGGTCCTGGTGCTGAGGGAATATACACCGAGGGCCTGATGCACAAC
              1651                                           1700
EBOV-B opt  (1651) CAGAACGGGCTGATTTGCGGGCTGCGCCAGCTCGCCAACGAGACTACCCA
EBOV-S opt  (1651) CAGAACGCCCTGGTGTGCGGCCTGAGACAGCTGGCCAACGAAACCACTCA
              1701                                           1750
EBOV-B opt  (1701) GGCCCTCCAGCTCTTTCTCCGGGCTACTACCGAACTGCGAACCTTTTCCA
EBOV-S opt  (1701) GGCACTGCAGCTGTTCCTGCGGGCCACCACCGAGCTGCGGACCTACACCA
              1751                                           1800
EBOV-B opt  (1751) TTCTCAATAGGAAAGCTATCGATTTCTTGCTCCAGCGCTGGGGGGGAACC
EBOV-S opt  (1751) TCCTGAACAGGAAGGCCATCGACTTTCTGCTGCGGAGATGGGGCGGCACC
              1801                                           1850
EBOV-B opt  (1801) TGTCATATCCTCGGACCCGATTGCTGTATTGAGCCACATGATTGGACTAA
EBOV-S opt  (1801) TGTAGAATCCTGGGCCCCGACTGCTGCATCGAGCCCCACGACTGGACCAA
              1851                                           1900
EBOV-B opt  (1851) AAACATCACTGACAAAATTGATCAGATCATTCATGATTTCATTGATAAAC
EBOV-S opt  (1851) GAATATCACCGACAAGATCAACCAGATCATCCACGACTTCATCGACAACC
              1901                                           1950
EBOV-B opt  (1901) CCCTCCCCGATCAGACTGATAATGACAATTGGTGGACGGGATGGCGCCAG
EBOV-S opt  (1901) CCCTGCCCAACCAGGACAACGACGACAACTGGTGGACTGGTTGGCGACAG
              1951                                           2000
EBOV-B opt  (1951) TGGGTGCCCGCTGGGATTGGCATTACAGGTGTCATTATTGCCGTGATTGC
EBOV-S opt  (1951) TGGATCCCTGCCGGCATCGGCATCACCGGCATCATCATTGCCATTATCGC
              2001                    2031
EBOV-B opt  (2001) ACTCCTGTGTATCTGTAAATTTCTGCTGTGA
EBOV-S opt  (2001) TCTCCTCTGCGTGTGCAAGCTCCTCTGCTGA
```

1                                                50
EBOV-S opt    (1)    ATGGGCGCCTGAGCCTGCTTCAGCTGCCTCGGGACAAGTTCGGAAGTC
EBOV-Z opt    (1)    ATGGGCGTGACAGGCATCTTCCAGCTCCTCAGAGACAGATTCAACGGCA
                                51                                               100
EBOV-S opt    (51)   GAGCTTCTTGGTGTGGGCGATCATCCTGTTCCAGAAAGCCTTCAGCATGG
EBOV-Z opt    (51)   GTCCTTTTTCCTCTGGGCCATCATTCTGTTTCAGCGGACCTTCTCCATCC
                                101                                              150
EBOV-S opt    (101)  GCTTCGGCGTGCGACAAGCAGCAGCCGGAAGTGACCAGCATCCAGCCAG
EBOV-Z opt    (101)  GTCTGGGCGTGACCCACAATAGCACCCTCCAGCTGTCCGACGTGGACAAG
                                151                                              200
EBOV-S opt    (151)  CTGCTGTGCAAGGACCACGTGGCAGCACCGATCGCCTGAAGTCCGTGGG
EBOV-Z opt    (151)  CTCCGTGTGCCGGGACAAGCTGTCCTCCAGCAACCAGCTGAGAAGCGTGGG
                                201                                              250
EBOV-S opt    (201)  CCTGAACCTGGAAGGCAGCGGCCGTGAGCCAGCGACATCCTGAGCGCCACCA
EBOV-Z opt    (201)  GCTGAATCTCCACGGCAATGCCCGTGCCACAGAACCTGCCCTCCGCCACAA
                                251                                              300
EBOV-S opt    (251)  AGAGATGGGGCTTCAGATCGCCCGGCCCAAGGTGGTGTCTTATGAC
EBOV-Z opt    (251)  AGCGCTGGGGCTTCGAGGCCCCGTCCTAAAGTCCTGAACTACGAG
                                301                                              350
EBOV-S opt    (301)  GCCGGCGAGTGGGCCGAGAACTGCTACAACCTGGAAATCAAGAAGCCGG
EBOV-Z opt    (301)  GAGGCAATGGCTGAAAATTGTTACAATCTCGAGATCAAAAAGCCAGA
                                351                                              400
EBOV-S opt    (351)  CGGCAGCCAGTGTCTGCCTCCCCTGCCGATGGGCGTGAGAGGCTTCCCCC
EBOV-Z opt    (351)  TGGCTCTGAGTGCCCTGCCGGCACCACGGCATCAGGGCTTCCCTA
                                401                                              450
EBOV-S opt    (401)  GGTGCAGATACGTGCAACAAGGCACAAGGCACCGGTCCATGCCCAGGGCGAC
EBOV-Z opt    (401)  GATGCCGCTATGCGCACAAGGTGAGTGGCTACAGGCCCTTGTGCCGGCGAT
                                451                                              500
EBOV-S opt    (451)  TACGCCTTCCACAAGGAGCGGCGGCTTTTCCTGTACGACCGGCTGGCCTC
EBOV-Z opt    (451)  TTTGCCTTCACAAAGAGGGCGTTCCTTCTGTACGACAGGCTCGCCAG
                                501                                              550
EBOV-S opt    (501)  CACCGTGATCTACCGGGCGTGAACTTTGCCGAGGCCGTGATCGCCCTCC
EBOV-Z opt    (501)  TACAGTGATATACCGAGGTACTACCTTCCCCGAAGGCGTCGCTGGCCTTTC
                                551                                              600
EBOV-S opt    (551)  TGATCCTGGCCAAGCCCAAGAGACATTCCTGCAGAGGCCCGGCATCCGG
EBOV-Z opt    (551)  TCATTCTGCCCCAGGGCCAAGAAGGACTTCTTCAGCAGGGCACGCCTGAGA
                                601                                              650
EBOV-S opt    (601)  GAGGCCGTGAACTACACCGAGAACCACCAGCAGCTACTACGCCACCTCCTA
EBOV-Z opt    (601)  GAACCCGTGAACGCCAGAGAGGAGCCCAGCAGCGGCTACTACAGCACCAC
                                651                                              700
EBOV-S opt    (651)  CCTGGAATACGAGATCGAGAACTTCGGCGCCAGCACAGCACCACGGTGT
EBOV-Z opt    (651)  AATCAGATACCAGGCCACAGGCTTCGGCACCAATGAGACAGAGTACCTGT
                                701                                              750
EBOV-S opt    (701)  TCAAGATCGACAACAACACCTTCGTCGGCTGACAGACCCCACAGCCCC
EBOV-Z opt    (701)  TCGAGGTGGACAACCTGACCTACGTCCAGCTGGAAGCCGGGTTTACCCCT
                                751                                              800
EBOV-S opt    (751)  AGCTTTCTGTTCCAGCTGAGCGACATCCATCTGCATCAGCAGCTGTC
EBOV-Z opt    (751)  AGCTTCCTCCTGCAGCTCAACGGAGACAATCTACACCTCCGGCAAGCGGAG
                                801                                              850
EBOV-S opt    (801)  CAACACCACCGGAGACGATCTGGACCCTGGACGCCAACATCAACGGCG
EBOV-Z opt    (801)  CAACACAAGCAGGCAAGCCATCGGCAAGTGAACCCCGAGATCGATACCA
                                851                                              900
EBOV-S opt    (851)  ACATCCGTGAATGGGCTTTGGGAGACAAGAACAATCTGAGCGAGCAG
EBOV-Z opt    (851)  CTATAGGGAGTGGGCTCCTGGGAAACTAAGAACAACCTCACCCGGAAG
                                901                                              950
EBOV-S opt    (901)  CTGCGGGGCGAAGAACTCAGCTTCGAGGCCCTGAGCCTGAACGAGACAGA
EBOV-Z opt    (901)  ATCAGATCCGAGGAACGTCCTTCACCGTGGTGTCCAACGGCGCCAAGAA
                                951                                              1000
EBOV-S opt    (951)  GGACGACACGCCGCCAGGAGCCGGATCACCAAGGGCGGGATCGCGACC
EBOV-Z opt    (951)  CATTTCAGGACAGAGCCCGCCAGAACAGCAGCCACCCCGGCACCAACA Figure 9B (continued)

```
            1951                                               2000
EBOV-S opt (1951) TGCATCCGTGCCGGCATCGGCATCACCGGCATCATCATGCCATATCCG
EBOV-Z opt (1951) TGCATTGAGCGGGATGCCGTGACCGGCGTGATATCGCCGTGATGCG
            2001            2031
EBOV-S opt (2001) TCTCCGCTGCGGTGTGCAAGCTCCTCTGCTGA
EBOV-Z opt (2001) CGTGTGCTGGATCTGCAAGTTCGAGTTCTGA
```

Figure 9B (continued)

SEQUENCE LISTING

```
<160> NUMBER OF SEQ ID NOS: 13

<210> SEQ ID NO 1
<211> LENGTH: 1725
<212> TYPE: DNA
<213> ORGANISM: respiratory syncytial virus

<400> SEQUENCE: 1
atggatttgc caatcctcaa aacaaatgca attaccacaa tctttgctgc agtcacactc      60
tgtttcgctt ccagtcaaaa catcactgta gaattttatc aatcaacatg cagtgcagtt     120
agcaaaggct atcttagtgc tttaagaact ggttggtata ctagtgttat aactatagaa     180
ttaagtaata tcaaggaaaa taagtgtaat ggaacagacg ctaaggtaaa attgataaaa     240
caagaattag ataaatataa aaatgctgta acagaattgc agttgctcat gcaaagcaca     300
ccagcagcca acaatcgggc cagaagagaa ctaccaaggt ttatgaatta tacactcaac     360
aataccaaaa ataacaatgt aacattaagc aagaaaagga aagaagatt tcttggcttc      420 ttgttaggtg ttggatctgc aatcgccagt ggcattgctg tatctaaagt cctgcaccta     480
gaaggggaag tgaacaaaat caaaagtgct ttactatcca caacaaggc tgtagtcagc       540 ttatcaaatg gagttagtgt cttaaccagc aaagtgttag acctcaaaaa ctatatagat      600
aaacaattgt tacccattgt gaacaagcaa agctgcagca tatcaaacat tgaaactgtg      660
atagaattcc aacaaaagag caacagacta ctagagatta ccagggaatt tagtgttaat      720
gcaggtgtaa ctacacctgt aagcacttat atgttaacaa atagtgaatt attatcatta     780
atcaatgata tgcctataac aaatgatcag aaaagttaa tgtccaacaa tgttcaaata      840
gttagacagc aaagttactc tatcatgtcc ataataaagg aggaagtctt agcatatgta     900
gtacaattac cactatatgg tgtaatagat acaccttgtt ggaaactaca cacatcccct     960
ctatgcacaa ccaacacaaa ggaagggtcc aacatctgtt taacaagaac cgacagagga   1020
tggtactgtg acaatgcagg atcagtgtct ttcttcccac aagctgaaac atgcaaagtt   1080
caatcgaatc gagtattttg tgacacaatg aacagtttaa cattaccaag tgaagtaaat    1140
ctctgcaaca ttgacatatt caaccctaaa tatgattgca aaattatgac ttcaaaaaca    1200
gatgtaagca gctccgttat cacatctcta ggagccattg tgtcatgcta tggcaaaact   1260
```

-continued

```
aaatgtacag catccaataa aaatcgtgga atcataaaga cattttctaa cgggtgtgat   1320
tatgtatcaa acaagggggt ggacactgta tctgtaggta atacgttata ttatgtaaat   1380
aagcaagaag gaaaaagtct ctatgtaaaa ggtgaaccaa taataaattt ctatgaccca   1440
ttagtgttcc cttctgatga atttgatgca tcaatatctc aagtcaatga gaagattaac   1500
cagagcctag catttattcg taaatccgat gaattattac ataatgtaaa tgttggtaaa   1560
tccaccacaa atatcatgat aactactata attatagtga ttatagtaat attgttatta   1620
ttaattgcag ttgggctgtt cctatactgc aaggccagaa gcacaccagt cacactaagc   1680
aaggatcaac tgagtggtat aaataatatt gcatttagta actga                   1725

<210> SEQ ID NO 2
<211> LENGTH: 1575
<212> TYPE: DNA
<213> ORGANISM: respiratory syncytial virus

<400> SEQUENCE: 2
atggatctcc ccattctcaa gaccaacgcc atcaccacca tcttcgccgc cgtgaccctg     60
tgtttcgcca gcagccagaa catcaccgtg gagttctacc agagcacctg cagcgccgtg    120
agcaagggct acctgagcgc cctgaggacc ggctggtaca ccagcgtgat caccatcgag    180
ctgtccaaca tcaaagaaaa caagtgcaac ggcaccgacg ccaaagtgaa gctgatcaag    240
caggaactgg acaagtacaa gaacgccgtg accgagctgc agctgctgat gcagagcacc    300
cctgccgcca acaacagagc caggcgcgag ctgccccggt tcatgaacta caccctgaac    360
aacaccaaga acaacaacgt gaccctgagc aagaagcgga agcggcggtt cctgggcttt    420
ctgctgggcg tgggcagcgc cattgccagc ggcattgccg tgtctaaggt cctgcatctg    480
gaaggcgagg tcaacaagat taagagcgcc ctgctgtcca ccaacaaggc cgtggtgtcc    540
ctgagcaacg gcgtgagcgt gctgaccagc aaggtgctgg atctgaagaa ctacatcgac    600
aagcagctgc tgcccatcgt gaataagcag tcctgcagca tcagcaacat cgagacagtg    660
atcgagttcc agcagaagag caaccggctg ctggaaatca cccgggagtt cagcgtgaat    720
gccggcgtga ccacccccgt gtccacctac atgctgacca acagcgagct gctgtccctg    780
atcaatgaca tgcccatcac caacgaccaa aagaaactga tgagcaacaa cgtgcagatc    840
gtgcggcagc agagctacag catcatgagc atcatcaaag aagaggtgct ggcctacgtg    900
gtgcagctgc ccctgtacgg cgtgatcgac acccccctgct ggaagctgca caccagcccc    960
ctgtgcacca ccaacaccaa agagggcagc aacatctgcc tgacccggac cgataggggc   1020
tggtactgcg acaacgccgg cagcgtgtcc ttctttcccc aagccgagac ttgcaaggtg   1080
cagagcaaca gggtgttctg cgacaccatg aacagcctga ccctgcccag cgaagtgaac   1140
ctgtgcaaca tcgacatctt taaccccaag tacgactgca agatcatgac ctccaagacc   1200
gacgtgtcca gctccgtgat taccagcctg ggcgccatcg tgtcctgcta cggcaagacc   1260
aagtgcaccg ccagcaacaa gaaccggggc atcatcaaga ccttcagcaa cggctgcgac   1320
tacgtgtcca ataagggcgt ggacaccgtg tccgtgggca acacactgta ctacgtgaac   1380
aagcaggaag gcaagagcct gtacgtgaag ggcgagccca tcatcaactt ctacgacccc   1440
ctggtgttcc ccagcgacga gttcgacgcc agcatcagcc aagtgaacga gaagatcaat   1500
cagtccctgg ccttcatcag gaagagcgac gagctgctgc acaatgtgaa cgtgggcaag   1560
tccaccacca actga                                                    1575
```

<210> SEQ ID NO 3
<211> LENGTH: 574
<212> TYPE: PRT
<213> ORGANISM: respiratory syncytial virus

<400> SEQUENCE: 3

```
Met Asp Leu Pro Ile Leu Lys Thr Asn Ala Ile Thr Thr Ile Phe Ala
1               5                   10                  15

Ala Val Thr Leu Cys Phe Ala Ser Ser Gln Asn Ile Thr Val Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Asn Asn Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Ser Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Ile
    370                 375                 380
```

```
Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu His Asn Val Asn Val Gly Lys Ser Thr Thr Asn Ile Met Ile Thr
            515                 520                 525

Thr Ile Ile Ile Val Ile Ile Val Ile Leu Leu Leu Ile Ala Val
            530                 535                 540

Gly Leu Phe Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
            565                 570

<210> SEQ ID NO 4
<211> LENGTH: 524
<212> TYPE: PRT
<213> ORGANISM: respiratory syncytial virus

<400> SEQUENCE: 4

Met Asp Leu Pro Ile Leu Lys Thr Asn Ala Ile Thr Thr Ile Phe Ala
1               5                   10                  15

Ala Val Thr Leu Cys Phe Ala Ser Ser Gln Asn Ile Thr Val Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Asn Asn Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
```

```
                  180                 185                 190
Leu Asp Leu Lys Asn Tyr Ile Asp Lys Gln Leu Leu Pro Ile Val Asn
            195                 200                 205

Lys Gln Ser Cys Ser Ile Ser Asn Ile Glu Thr Val Ile Glu Phe Gln
            210                 215                 220

Gln Lys Ser Asn Arg Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
            290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Ile
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu His Asn Val Asn Val Gly Lys Ser Thr Thr Asn
            515                 520

<210> SEQ ID NO 5
<211> LENGTH: 676
<212> TYPE: PRT
<213> ORGANISM: Ebolavirus bundibugyo

<400> SEQUENCE: 5

Met Val Thr Ser Gly Ile Leu Gln Leu Pro Arg Glu Arg Phe Arg Lys
1               5                   10                  15

Thr Ser Phe Phe Val Trp Val Ile Leu Phe His Lys Val Phe Pro
            20                  25                  30
```

```
Ile Pro Leu Gly Val Val His Asn Asn Thr Leu Gln Val Ser Asp Ile
             35                  40                  45
Asp Lys Leu Val Cys Arg Asp Lys Leu Ser Ser Thr Ser Gln Leu Lys
 50                  55                  60
Ser Val Gly Leu Asn Leu Glu Gly Asn Gly Val Ala Thr Asp Val Pro
 65                  70                  75                  80
Thr Ala Thr Lys Arg Trp Gly Phe Arg Ala Gly Val Pro Pro Lys Val
                 85                  90                  95
Val Asn Tyr Glu Ala Gly Glu Trp Ala Glu Asn Cys Tyr Asn Leu Asp
            100                 105                 110
Ile Lys Lys Ala Asp Gly Ser Glu Cys Leu Pro Glu Ala Pro Glu Gly
        115                 120                 125
Val Arg Gly Phe Pro Arg Cys Arg Tyr Val His Lys Val Ser Gly Thr
    130                 135                 140
Gly Pro Cys Pro Glu Gly Tyr Ala Phe His Lys Glu Gly Ala Phe Phe
145                 150                 155                 160
Leu Tyr Asp Arg Leu Ala Ser Thr Ile Ile Tyr Arg Ser Thr Thr Phe
                165                 170                 175
Ser Glu Gly Val Val Ala Phe Leu Ile Leu Pro Glu Thr Lys Lys Asp
            180                 185                 190
Phe Phe Gln Ser Pro Pro Leu His Glu Pro Ala Asn Met Thr Thr Asp
        195                 200                 205
Pro Ser Ser Tyr Tyr His Thr Val Thr Leu Asn Tyr Val Ala Asp Asn
    210                 215                 220
Phe Gly Thr Asn Met Thr Asn Phe Leu Phe Gln Val Asp His Leu Thr
225                 230                 235                 240
Tyr Val Gln Leu Glu Pro Arg Phe Thr Pro Gln Phe Leu Val Gln Leu
                245                 250                 255
Asn Glu Thr Ile Tyr Thr Asn Gly Arg Arg Ser Asn Thr Thr Gly Thr
            260                 265                 270
Leu Ile Trp Lys Val Asn Pro Thr Val Asp Thr Gly Val Gly Glu Trp
        275                 280                 285
Ala Phe Trp Glu Asn Lys Lys Asn Phe Thr Lys Thr Leu Ser Ser Glu
    290                 295                 300
Glu Leu Ser Val Ile Phe Val Pro Arg Ala Gln Asp Pro Gly Ser Asn
305                 310                 315                 320
Gln Lys Thr Lys Val Thr Pro Thr Ser Phe Ala Asn Asn Gln Thr Ser
                325                 330                 335
Lys Asn His Glu Asp Leu Val Pro Glu Asp Pro Ala Ser Val Val Gln
            340                 345                 350
Val Arg Asp Leu Gln Arg Glu Asn Thr Val Pro Thr Pro Pro Pro Asp
        355                 360                 365
Thr Val Pro Thr Thr Leu Ile Pro Asp Thr Met Glu Glu Gln Thr Thr
    370                 375                 380
Ser His Tyr Glu Pro Pro Asn Ile Ser Arg Asn His Gln Glu Arg Asn
385                 390                 395                 400
Asn Thr Ala His Pro Glu Thr Leu Ala Asn Asn Pro Pro Asp Asn Thr
                405                 410                 415
Thr Pro Ser Thr Pro Pro Gln Asp Gly Glu Arg Thr Ser His Thr
            420                 425                 430
Thr Pro Ser Pro Arg Pro Val Pro Thr Ser Thr Ile His Pro Thr Thr
        435                 440                 445
Arg Glu Thr His Ile Pro Thr Thr Met Thr Thr Ser His Asp Thr Asp
```

```
                    450                 455                 460
Ser Asn Arg Pro Asn Pro Ile Asp Ile Ser Glu Ser Thr Glu Pro Gly
465                 470                 475                 480

Pro Leu Thr Asn Thr Thr Arg Gly Ala Ala Asn Leu Leu Thr Gly Ser
                485                 490                 495

Arg Arg Thr Arg Arg Glu Ile Thr Leu Arg Thr Gln Ala Lys Cys Asn
            500                 505                 510

Pro Asn Leu His Tyr Trp Thr Thr Gln Asp Glu Gly Ala Ala Ile Gly
            515                 520                 525

Leu Ala Trp Ile Pro Tyr Phe Gly Pro Ala Ala Glu Gly Ile Tyr Thr
        530                 535                 540

Glu Gly Ile Met His Asn Gln Asn Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
610                 615                 620

Gln Ile Ile His Asp Phe Ile Asp Lys Pro Leu Pro Asp Gln Thr Asp
625                 630                 635                 640

Asn Asp Asn Trp Trp Thr Gly Trp Arg Gln Trp Val Pro Ala Gly Ile
                645                 650                 655

Gly Ile Thr Gly Val Ile Ile Ala Val Ile Ala Leu Leu Cys Ile Cys
            660                 665                 670

Lys Phe Leu Leu
        675

<210> SEQ ID NO 6
<211> LENGTH: 676
<212> TYPE: PRT
<213> ORGANISM: Sudan ebolavirus strain Gulu

<400> SEQUENCE: 6

Met Gly Gly Leu Ser Leu Leu Gln Leu Pro Arg Asp Lys Phe Arg Lys
1               5                   10                  15

Ser Ser Phe Phe Val Trp Val Ile Ile Leu Phe Gln Lys Ala Phe Ser
                20                  25                  30

Met Pro Leu Gly Val Val Thr Asn Ser Thr Leu Glu Val Thr Glu Ile
            35                  40                  45

Asp Gln Leu Val Cys Lys Asp His Leu Ala Ser Thr Asp Gln Leu Lys
        50                  55                  60

Ser Val Gly Leu Asn Leu Glu Gly Ser Gly Val Ser Thr Asp Ile Pro
65                  70                  75                  80

Ser Ala Thr Lys Arg Trp Gly Phe Arg Ser Gly Val Pro Pro Lys Val
                85                  90                  95

Val Ser Tyr Glu Ala Gly Glu Trp Ala Glu Asn Cys Tyr Asn Leu Glu
            100                 105                 110

Ile Lys Lys Pro Asp Gly Ser Glu Cys Leu Pro Pro Pro Asp Gly
        115                 120                 125

Val Arg Gly Phe Pro Arg Cys Arg Tyr Val His Lys Ala Gln Gly Thr
    130                 135                 140
```

```
Gly Pro Cys Pro Gly Asp Tyr Ala Phe His Lys Asp Gly Ala Phe Phe
145                 150                 155                 160

Leu Tyr Asp Arg Leu Ala Ser Thr Val Ile Tyr Arg Gly Val Asn Phe
            165                 170                 175

Ala Glu Gly Val Ile Ala Phe Leu Ile Leu Ala Lys Pro Lys Glu Thr
        180                 185                 190

Phe Leu Gln Ser Pro Pro Ile Arg Glu Ala Val Asn Tyr Thr Glu Asn
        195                 200                 205

Thr Ser Ser Tyr Tyr Ala Thr Ser Tyr Leu Glu Tyr Glu Ile Glu Asn
        210                 215                 220

Phe Gly Ala Gln His Ser Thr Thr Leu Phe Lys Ile Asp Asn Asn Thr
225                 230                 235                 240

Phe Val Arg Leu Asp Arg Pro His Thr Pro Gln Phe Leu Phe Gln Leu
            245                 250                 255

Asn Asp Thr Ile His Leu His Gln Gln Leu Ser Asn Thr Thr Gly Arg
            260                 265                 270

Leu Ile Trp Thr Leu Asp Ala Asn Ile Asn Ala Asp Ile Gly Glu Trp
            275                 280                 285

Ala Phe Trp Glu Asn Lys Lys Asn Leu Ser Glu Gln Leu Arg Gly Glu
        290                 295                 300

Glu Leu Ser Phe Glu Ala Leu Ser Leu Asn Glu Thr Glu Asp Asp Asp
305                 310                 315                 320

Ala Ala Ser Ser Arg Ile Thr Lys Gly Arg Ile Ser Asp Arg Ala Thr
            325                 330                 335

Arg Lys Tyr Ser Asp Leu Val Pro Lys Asn Ser Pro Gly Met Val Pro
            340                 345                 350

Leu His Ile Pro Glu Gly Glu Thr Thr Leu Pro Ser Gln Asn Ser Thr
            355                 360                 365

Glu Gly Arg Arg Val Gly Val Asn Thr Gln Glu Thr Ile Thr Glu Thr
            370                 375                 380

Ala Ala Thr Ile Ile Gly Thr Asn Gly Asn His Met Gln Ile Ser Thr
385                 390                 395                 400

Ile Gly Ile Arg Pro Ser Ser Ser Gln Ile Pro Ser Ser Ser Pro Thr
            405                 410                 415

Thr Ala Pro Ser Pro Glu Ala Gln Thr Pro Thr Thr His Thr Ser Gly
            420                 425                 430

Pro Ser Val Met Ala Thr Glu Glu Pro Thr Thr Pro Gly Ser Ser
            435                 440                 445

Pro Gly Pro Thr Thr Glu Ala Pro Thr Leu Thr Thr Pro Glu Asn Ile
    450                 455                 460

Thr Thr Ala Val Lys Thr Val Leu Pro Gln Glu Ser Thr Ser Asn Gly
465                 470                 475                 480

Leu Ile Thr Ser Thr Val Thr Gly Ile Leu Gly Ser Leu Gly Leu Arg
            485                 490                 495

Lys Arg Ser Arg Arg Gln Thr Asn Thr Lys Ala Thr Gly Lys Cys Asn
            500                 505                 510

Pro Asn Leu His Tyr Trp Thr Ala Gln Glu Gln His Asn Ala Ala Gly
            515                 520                 525

Ile Ala Trp Ile Pro Tyr Phe Gly Pro Gly Ala Glu Gly Ile Tyr Thr
            530                 535                 540

Glu Gly Leu Met His Asn Gln Asn Ala Leu Val Cys Gly Leu Arg Gln
545                 550                 555                 560

Leu Ala Asn Glu Thr Thr Gln Ala Leu Gln Leu Phe Leu Arg Ala Thr
```

-continued

```
                        565                 570                 575
Thr Glu Leu Arg Thr Tyr Thr Ile Leu Asn Arg Lys Ala Ile Asp Phe
                580                 585                 590

Leu Leu Arg Arg Trp Gly Gly Thr Cys Arg Ile Leu Gly Pro Asp Cys
            595                 600                 605

Cys Ile Glu Pro His Asp Trp Thr Lys Asn Ile Thr Asp Lys Ile Asn
        610                 615                 620

Gln Ile Ile His Asp Phe Ile Asp Asn Pro Leu Pro Asn Gln Asp Asn
625                 630                 635                 640

Asp Asp Asn Trp Trp Thr Gly Trp Arg Gln Trp Ile Pro Ala Gly Ile
                645                 650                 655

Gly Ile Thr Gly Ile Ile Ile Ala Ile Ile Ala Leu Leu Cys Val Cys
                660                 665                 670

Lys Leu Leu Cys
            675

<210> SEQ ID NO 7
<211> LENGTH: 676
<212> TYPE: PRT
<213> ORGANISM: Zaire ebolavirus Mayinga strain

<400> SEQUENCE: 7

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255
```

-continued

```
Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Val Val Ser Asn Gly Ala Lys Asn Ile Ser Gly
305                 310                 315                 320

Gln Ser Pro Ala Arg Thr Ser Ser Asp Pro Gly Thr Asn Thr Thr Thr
                325                 330                 335

Glu Asp His Lys Ile Met Ala Ser Glu Asn Ser Ser Ala Met Val Gln
            340                 345                 350

Val His Ser Gln Gly Arg Glu Ala Ala Val Ser His Leu Thr Thr Leu
        355                 360                 365

Ala Thr Ile Ser Thr Ser Pro Gln Ser Leu Thr Thr Lys Pro Gly Pro
    370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
                405                 410                 415

Ala Ser Asp Thr Pro Ser Ala Thr Thr Ala Ala Gly Pro Pro Lys Ala
            420                 425                 430

Glu Asn Thr Asn Thr Ser Lys Ser Thr Asp Phe Leu Asp Pro Ala Thr
        435                 440                 445

Thr Thr Ser Pro Gln Asn His Ser Glu Thr Ala Gly Asn Asn Asn Thr
    450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Ile
    530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670

Lys Phe Val Phe
```

675

<210> SEQ ID NO 8
<211> LENGTH: 2031
<212> TYPE: DNA
<213> ORGANISM: Ebolavirus bundibugyo

<400> SEQUENCE: 8

```
atggttacat caggaattct acaattgccc cgtgaacgct tcagaaaaac atcatttttt      60
gtttgggtaa taatcctatt tcacaaagtt ttccctatcc cattgggcgt agttcacaac     120
aacactctcc aggtaagtga tatagataaa ttggtgtgcc gggataaact ttcctccaca     180
agtcagctga atcggtcgg gcttaatcta aaggtaatg gagttgccac agatgtacca      240
acagcaacga agagatgggg attccgagct ggtgttccac ccaaagtggt gaactacgaa     300
gctggggagt gggctgaaaa ctgctacaac ctggacatca agaaagcaga tggtagcgaa     360
tgcctacctg aagccctga gggtgtaaga ggcttccctc gctgccgtta tgtgcacaag     420
gtttctggaa cagggccgtg ccctgaaggt tacgctttcc acaagaagg cgctttcttc      480
ctgtatgatc gactggcatc aacaatcatc tatcgaagca ccacgttttc agaaggtgtt     540
gtggctttct tgatcctccc cgaaactaaa aaggactttt ccaatcgcc accactacat     600
gaaccggcca atatgacaac agacccatcc agctactacc acacagtcac acttaattat     660
gtggctgaca atttgggac caatatgact aactttctgt tcaagtgga tcatctaact      720
tatgtgcaac ttgaaccaag attcacacca caatttcttg tccaactcaa tgagaccatt     780
tatactaatg gcgtcgcag caacaccaca ggaacactaa tttggaaagt aaatcctact     840
gttgacaccg gcgtaggtga atgggccttc tgggaaaata gaagaactt cacaaaaacc     900
ctttcaagtg aagagctgtc tgtcatattt gtaccaagag cccaggatcc aggcagcaac     960
cagaagacga aggtcactcc caccagcttc gccaacaacc aaacctccaa gaaccacgaa    1020
gacttggttc cagaggatcc cgcttcagtg gttcaagtgc agacctcca gagggaaaac    1080
acagtgccga ccccacccc agacacagtc cccacaactc tgatccccga cacaatggag    1140
gaacaaacca ccagccacta cgaaccacca aacatttcca gaaaccatca agagagaac     1200
aacaccgcac accccgaaac tctcgccaac aatcccccag acaacacaac cccgtcgaca    1260
ccacctcaag acgtgagcg acaagttcc cacacaacac cctcccccg cccagtccca      1320
accagcacaa tccatcccac cacgagag actcacattc ccaccacaat gacaacaagc     1380
catgacaccg acagcaatcg acccaaccca attgacatca gcgagtctac agagccagga    1440
ccactcacca acaccacaag aggggctgca atctgctga caggctcaag aagaacccga    1500
agggaaatca ccctgagaac acaagccaaa tgcaacccaa acctacacta ttggacaacc    1560
caagatgaag gggctgccat tggtttagcc tggataccct acttcgggcc cgcagcagag    1620
ggaattata cggaagggat aatgcacaat caaatgggc taatttgcgg ttgaggcag      1680
ctagcaaatg agacgactca gccctacag ttattcttgc gtgctaccac ggaattgcgc    1740
actttctcta tattgaatcg aaaagccatc gactttttac tccaaagatg gggaggaacg    1800
tgccacatct taggcccaga ttgctgtatt gagccccatg attggactaa gaacattact    1860
gacaaaatag atcaaatcat tcatgatttc attgataaac ctctaccaga tcaaacagat    1920
aatgacaatt ggtggacagg gtggaggcaa tgggttcctg ccgggatcgg gatcacgggg    1980
gtaataatcg cagttatagc actgctgtgt atttgcaaat ttctactcta a             2031
```

<210> SEQ ID NO 9
<211> LENGTH: 2031
<212> TYPE: DNA
<213> ORGANISM: Sudan ebolavirus strain Gulu

<400> SEQUENCE: 9

```
atgggggtc ttagcctact ccaattgccc agggacaaat ttcggaaaag ctctttcttt      60
gtttgggtca tcatcttatt ccaaaaggcc ttttccatgc ctttgggtgt tgtgactaac     120
agcactttag aagtaacaga gattgaccag ctagtctgca aggatcatct tgcatctact     180
gaccagctga aatcagttgg tctcaacctc gaggggagcg agtatctac tgatatccca     240
tctgcaacaa agcgttgggg cttcagatct ggtgttcctc caaggtggt cagctatgaa     300
gcgggagaat gggctgaaaa ttgctacaat cttgaaataa agaagccgga cgggagcgaa     360
tgcttacccc caccgccaga tggtgtcaga ggctttccaa ggtgccgcta tgttcacaaa     420
gcccaaggaa ccgggccctg cccaggtgac tacgcctttc acaaggatgg agctttcttc     480
ctctatgaca ggctggcttc aactgtaatt tacagaggag tcaattttgc tgaggggta     540
attgcattct tgatattggc taaaccaaaa gaaacgttcc ttcagtcacc ccccattcga     600
gaggcagtaa actacactga aaatacatca agttattatg ccacatccta cttggagtat     660
gaaatcgaaa attttggtgc tcaacactcc acgaccctt tcaaaattga caataatact     720
tttgttcgtc tggacaggcc ccacacgcct cagttccttt tccagctgaa tgataccatt     780
caccttcacc aacagttgag taatacaact gggagactaa tttggacact agatgctaat     840
atcaatgctg atattggtga atgggctttt tgggaaaata aaaaaaatct ctccgaacaa     900
ctacgtggag aagagctgtc tttcgaagct ttatcgctca acgagacaga agacgatgat     960
gcggcatcgt cgagaattac aaagggaaga atctccgacc gggccaccag gaagtattcg    1020
gacctggttc caaagaattc ccctgggatg gttccattgc ataccaga agggaaaca    1080
acattgccgt ctcagaattc gacagaaggt cgaagagtag gtgtgaacac tcaggagacc    1140
attacagaga cagctgcaac aattataggc actaacggca accatatgca gatctccacc    1200
atcgggataa gaccgagctc cagccaaatc ccgagttcct caccgaccac ggcaccaagc    1260
cctgaggctc agaccccac aacccacaca tcaggtccat cagtgatggc caccgaggaa    1320
ccaacaacac caccgggaag ctcccccggc ccaacaacag aagcacccac tctcaccacc    1380
ccagaaaata taacaacagc ggttaaaact gtcctgccac aggagtccac aagcaacggt    1440
ctaataactt caacagtaac agggattctt gggagtcttg gcttcgaaa acgcagcaga    1500
agacaaacta caccaaagc cacgggtaag tgcaatccca acttacacta ctggactgca    1560
caagaacaac ataatgctgc tgggattgcc tggatcccgt actttggacc gggtgcggaa    1620
ggcatataca ctgaaggcct gatgcataac caaaatgcct tagtctgtgg acttaggcaa    1680
cttgcaaatg aaacaactca agctctgcag ctttctta gagccacaac ggagctgcgg    1740
acatatacca tactcaatag aaggccata gatttcctc tgcgacgatg gggcgggaca    1800
tgcaggatcc tgggaccaga ttgttgcatt gagccacatg attggacaaa aacatcact    1860
gataaaatca accaaatcat ccatgatttc atcgacaacc ccttacctaa tcaggataat    1920
gatgataatt ggtggacggg ctggagacag tggatccctg caggaatagg cattactgga    1980
attattattg caattattgc tcttctttgc gtttgcaagc tgctttgctg a             2031
```

<210> SEQ ID NO 10
<211> LENGTH: 2031
<212> TYPE: DNA

<213> ORGANISM: Zaire ebolavirus Mayinga strain

<400> SEQUENCE: 10

```
atgggcgtta caggaatatt gcagttacct cgtgatcgat tcaagaggac atcattcttt      60
ctttgggtaa ttatccttt  ccaaagaaca ttttccatcc cacttggagt catccacaat     120
agcacattac aggttagtga tgtcgacaaa ctagtttgtc gtgacaaact gtcatccaca     180
aatcaattga gatcagttgg actgaatctc gaagggaatg gagtggcaac tgacgtgcca     240
tctgcaacta aagatgggg  cttcaggtcc ggtgtccac  caaaggtggt caattatgaa     300
gctggtgaat gggctgaaaa ctgctacaat cttgaaatca aaaaacctga cgggagtgag     360
tgtctaccag cagcgccaga cgggattcgg ggcttccccc ggtgccggta tgtgcacaaa     420
gtatcaggaa cgggaccgtg tgccggagac tttgccttcc ataaagaggg tgctttcttc     480
ctgtatgatc gacttgcttc cacagttatc taccgaggaa cgactttcgc tgaaggtgtc     540
gttgcatttc tgatactgcc ccaagctaag aaggacttct tcagctcaca cccctttgaga    600
gagccggtca tgcaacgga  ggacccgtct agtggctact attctaccac aattagatat     660
caggctaccg gttttggaac caatgagaca gagtacttgt tcgaggttga caatttgacc    720
tacgtccaac ttgaatcaag attcacacca cagtttctgc tccagctgaa tgagacaata    780
tatacaagtg ggaaaggag  caataccacg ggaaaactaa tttggaaggt caaccccgaa    840
attgatacaa caatcgggga gtgggccttc tgggaaacta aaaaaaacct cactagaaaa    900
attcgcagtg aagagttgtc tttcacagtt gtatcaaacg agccaaaaa  catcagtggt    960
cagagtccgg cgcgaacttc ttccgaccca gggaccaaca caacaactga agaccacaaa   1020
atcatggctt cagaaaattc ctctgcaatg gttcaagtgc acagtcaagg aagggaagct   1080
gcagtgtcgc atctaacaac ccttgccaca atctccacga gtcccaatc  cctcacaacc   1140
aaaccaggtc cggacaacag cacccataat acaccgtgt  ataaacttga catctctgag   1200
gcaactcaag ttgaacaaca tcaccgcaga acagacaacg acagcacagc ctccgacact   1260
ccctctgcca cgaccgcagc cggacccca  aaagcagaga acaccaacac gagcaagagc   1320
actgacttcc tggaccccgc caccacaaca agtccccaaa accacagcga gaccgctggc   1380
aacaacaaca ctcatcacca agataccgga gaagagagtg ccagcagcgg gaagctaggc   1440
ttaattacca atactattgc tggagtcgca ggactgatca caggcgggag aagaactcga   1500
agagaagcaa ttgtcaatgc tcaacccaaa tgcaacccta tttacattac tggactact    1560
caggatgaag tgctgcaat  cggactggcc tggataccat atttcgggcc agcagccgag   1620
ggaatttaca tagaggggct aatgcacaat caagatggtt taatctgtgg gttgagacag   1680
ctggccaacg agacgactca agctcttcaa ctgttcctga gagccacaac tgagctacgc   1740
acctttttca atcctcaaccg taaggcaatt gatttcttgc tgcagcgatg gggcggcaca   1800
tgccacattc tgggaccgga ctgctgtatc gaaccacatg attggaccaa gaacataaca   1860
gacaaaattg atcagattat tcatgatttt gttgataaaa cccttccgga ccaggggac   1920
aatgacaatt ggtggacagg atggagacaa tggataccgg caggtattgg agttacaggc    1980
gttataattg cagttatcgc tttattctgt atatgcaaat tgtctttta g             2031
```

<210> SEQ ID NO 11
<211> LENGTH: 2031
<212> TYPE: DNA
<213> ORGANISM: Ebolavirus bundibugyo

<400> SEQUENCE: 11

```
atggtcacat ctggaattct ccagctccct agggaacggt tccggaaaac cagtttcttt     60
gtctgggtca tcatcctctt ccataaggtg ttccctatcc cctgggggt cgtccataac    120
aatacattgc aagtgtcaga tatcgataag ttggtgtgtc gcgataaact gtcatctacc    180
tctcagctga aaagcgtcgg cctcaacctc gaagggaatg tgtcgccac tgatgtccct    240
actgccacaa acgatgggg tttccgggct ggtgtccccc caaaagtggt caactatgaa    300
gctggcgaat gggcagagaa ttgctataat ctggacatta aaaaggccga tggctccgag    360
tgtctccctg aagctcctga gggcgtgcgg ggattcccaa gatgtcgcta cgtccataaa    420
gtgtctggca ccggcccttg ccctgaagga tacgccttc ataaagaagg ggcctttttc    480
ctctatgatc gcctggcttc acaattatc tatcgctcta ctacctttc cgagggggtg    540
gtcgcttttc tcatcctccc cgagacaaag aaagatttct ttcagagtcc cccctgcat    600
gagcctgcca atatgactac cgatccttcc tcttactatc ataccgtgac actcaattat    660
gtcgctgata acttcggcac taacatgacc aactttctgt tccaggtcga ccacctgaca    720
tatgtccagc tcgagcctcg ctttaccca cagttcctgg tccagctcaa tgaaactatc    780
tatactaacg gacggcgctc taataccacc gggacctca tttggaaagt caatcccact    840
gtcgataccg gcgtcggaga gtgggccttt tgggaaaaca agaagaactt taccaagacc    900
ctgagtagcg aggaactctc tgtgatcttt gtgcctcgcg ctcaggatcc tggatccaac    960
cagaaaacca aagtgacacc tacatctttt gccaacaacc agacaagcaa gaaccatgag   1020
gacctcgtcc ccaagatcc tgcctctgtg gtccaggtcc gggacctcca gcgcgaaaat   1080
accgtgccta ctcccccccc tgataccgtc cctactaccc tcattcccga tacaatggaa   1140
gaacagacca cctctcatta cgagccacct aacatctcca gaaatcacca ggaacgaaat   1200
aacaccgctc atcccgagac tctggctaat aaccccccg acaatactac ccctagtacc   1260
cccctcagg acggggagag aaccagttcc catactacac cctccccaag acccgtccct   1320
acatctacca ttcatcccac cacccgcgag acacacattc ctaccactat gaccacatcc   1380
catgacaccg attccaatcg ccctaacccc atcgatatca gcgaatctac cgagcccgga   1440
cccctcacaa atacaacccg cggagccgct aatctgctga ctggctcccg gcgcactcga   1500
agagaaatca ccctgcgaac acaggccaag tgtaacccaa acctccatta ttggacaacc    1560
caggatgaag gggccgctat tggcctcgct tggatcccct atttcgggcc tgcagccgag    1620
gggatctata ccgaaggtat aatgcataat cagaacgggc tgatttgcgg gctgcgccag    1680
ctcgccaacg agactaccca ggccctccag ctctttctcc gggctactac cgaactgcga    1740
acctttccca ttctcaatag gaaagctatc gatttcttgc tccagcgctg gggggaacc    1800
tgtcatatcc tcggacccga ttgctgtatt gagcccacatg attggactaa aaacatcact    1860
gacaaaattg atcagatcat tcatgatttc attgataaac ccctccccga tcagactgat    1920
aatgacaatt ggtggacggg atggcgccag tgggtgcccg ctgggattgg cattacaggt    1980
gtcattattg ccgtgattgc actcctgtgt atctgtaaat ttctgctgtg a              2031

<210> SEQ ID NO 12
<211> LENGTH: 2031
<212> TYPE: DNA
<213> ORGANISM: Sudan ebolavirus strain Gulu

<400> SEQUENCE: 12
atgggcggcc tgagcctgct gcagctgccc cgggacaagt tccggaagtc cagcttcttc     60
```

```
gtgtgggtga tcatcctgtt ccagaaagcc ttcagcatgc ccctgggcgt ggtgaccaac    120
agcaccctgg aagtgaccga gatcgaccag ctggtgtgca aggaccacct ggccagcacc    180
gatcagctga agtccgtggg cctgaacctg gaaggcagcg gcgtgagcac cgacatcccc    240
agcgccacca agagatgggg cttcagatcc ggcgtgcccc ccaaggtggt gtcttatgag    300
gccggcgagt gggccgagaa ctgctacaac ctggaaatca gaagcccga cggcagcgag    360 tgtctgcctc cccctcccga tggcgtgaga ggcttccccc ggtgcagata cgtgcacaag    420
gcacaaggca ccggtccatg cccaggcgac tacgccttcc acaaggacgg cgccttttc    480 ctgtacgacc ggctggcctc caccgtgatc taccggggcg tgaactttgc cgagggcgtg    540
atcgccttcc tgatcctggc caagcccaaa gagacattcc tgcagagccc cccatccgg    600 gaggccgtga actacaccga gaacaccagc agctactacg ccacctccta cctggaatac    660
gagatcgaga acttcggcgc ccagcacagc accaccctgt tcaagatcga caacaacacc    720
ttcgtgcggc tggacagacc ccacaccccc cagtttctgt tccagctgaa cgacaccatc    780
catctgcatc agcagctgtc caacaccacc ggcagactga tctggaccct ggacgccaac    840
atcaacgccg acatcggtga atgggctttt gggagaaaca agaagaatct gagcgagcag    900
ctgcggggcg aagaactcag cttcgaggcc ctgagcctga cgagacaga ggacgacgac    960 gccgccagca gccggatcac caagggccgg atcagcgacc gggccaccag aaagtacagc    1020
gacctggtgc caagaacag ccccggcatg gtgcctctgc acatccccga gggcgagaca    1080
actctcccta gtcagaatag caccgagggc agacgcgtgg gcgtgaacac ccaggaaacc    1140
atcaccgaga cagccgccac catcattggt actaacggca accacatgca gatcagcacc    1200
atcggcatcc ggcccagcag cagccagatc ccaagtagta gtcctaccac agcccctagc    1260
cctgaggccc agaccctac cacacacacc agcggcccta gcgtgatggc caccgaggaa    1320
cctaccaccc ctcctggcag cagcccaggt ccaactaccg aggcaccaac cctgaccacc    1380
cccgagaaca tcaccaccgc cgtgaaaacc gtgctgcccc aggaaagcac cagcaacggc    1440
ctgatcacca gcaccgtgac cggcatcctg gcagcctgg gcctgcggaa cggagcaga    1500 cggcagacca caccaaggc caccggcaag tgcaacccca acctgcacta ctggaccgcc    1560
caggaacagc acaacgccgc tgggatcgcc tggatcccct actttggtcc tggtgctgag    1620
ggaatataca ccgagggcct gatgcacaac cagaacgccc tggtgtgcgg cctgagacag    1680
ctggccaacg aaaccactca ggcactgcag ctgttcctgc gggccaccac cgagctgcgg    1740
acctacacca tcctgaacag gaaggccatc gactttctgc tgcggagatg gggcggcacc    1800
tgtagaatcc tgggccccga ctgctgcatc gagccccacg actggaccaa gaatatcacc    1860
gacaagatca accagatcat ccacgacttc atcgacaacc ccctgcccaa ccaggacaac    1920
gacgacaact ggtggactgg ttggcgacag tggatccctg ccggcatcgg catcaccggc    1980
atcatcattg ccattatcgc tctcctctgc gtgtgcaagc tcctctgctg a              2031
```

<210> SEQ ID NO 13  
<211> LENGTH: 2031  
<212> TYPE: DNA  
<213> ORGANISM: Zaire ebolavirus Mayinga strain

<400> SEQUENCE: 13

```
atgggcgtga caggcattct gcagctcccc agagacagat tcaagcggac ctcctttttc     60
ctctgggtca tcattctgtt tcagcggacc ttctccatcc ctctgggcgt gatccacaat    120
agcaccctcc aggtgtccga cgtggacaag ctcgtgtgcc gggacaagct gtcctccacc    180
```

-continued

```
aaccagctga gaagcgtggg gctgaatctc gagggcaatg gcgtggccac agacgtgccc      240
tccgccacaa agcgctgggg ctttcggagc ggcgtccctc ctaaagtcgt gaactacgag      300
gcagggaat gggctgaaaa ttgttacaat ctcgagatca aaaaaccaga tggctctgag       360
tgcctgcctg ccgcaccaga cggcatcagg ggcttcccta gatgccgcta tgtgcacaag      420
gtgagtggta caggcccttg tgccggcgat tttgcctttc acaaagaggg ggctttcttt      480
ctgtacgaca ggctcgccag tacagtgata taccgaggta ctaccttcgc cgaaggcgtg      540
gtggcctttc tgattctgcc ccaggccaag aaggacttct tcagcagcca ccccctgaga      600
gaacccgtga acgccacaga ggaccccagc agcggctact acagcaccac aatcagatac      660
caggccacag gcttcggcac caatgagaca gagtacctgt tcgaggtgga caacctgacc      720
tacgtgcagc tggaaagccg gtttacccct cagttcctcc tgcagctcaa cgagacaatc      780
tacacctccg gcaagcggag caacacaaca ggcaagctca tctggaaagt gaaccccgag      840
atcgatacca ctataggga gtgggctttc tgggaaacta agaagaacct cacccggaag      900
atcagatccg aggaactgtc cttcaccgtg gtgtccaacg gcgccaagaa catttcagga     960
cagagccccg ccagaacaag cagcgacccc ggcaccaaca ccacaaccga ggaccacaag     1020
atcatggcca gcgagaactc cagcgccatg gtgcaggtcc acagccaggg aagagaagcc    1080
gccgtgagcc acctgaccac actggccacc atcagcacca gccccagag cctgaccacc     1140
aagcctggcc ccgacaacag cacacacaac accccgtgt acaagctgga catcagcgag      1200
gccacccagg tggagcagca ccacagacg accgacaacg acagcaccgc cagcgatacc      1260
ccttctgcca ccacagccgc cggacccct aaggccgaga ataccaacac cagcaagagc     1320
accgactttc tggatccagc caccaccacc agtccacaga accacagcga aaccgccggc     1380
aacaacaata cccaccacca ggacaccggc gaggaaagcg ccagctctgg caagctgggc    1440
ctgattacca acacaatcgc cggcgtggcc ggactgatca ccggcggcag acggaccaga     1500
cgggaggcca tcgtgaacgc ccagcccaaa tgtaatccta atctccacta ttggaccaca    1560
caggacgagg gcgctgccat cggactggca tggattcctt acttcggacc agccgctgaa    1620
gggatctata tcgaggggct catgcataac aggatggtc tgatttgtgg tctccggcag     1680
ctggctaatg agacaacaca ggctctccag ctgtttctga gagccacaac agagctgaga    1740
accttcagca tttctcaaccg caaggctatt gacttcctgc tccaacgatg gggaggcaca    1800
tgccacatcc tggggcctga ttgttgtatc gaacctcacg attggacaaa gaacattaca    1860
gataagatcg atcagattat ccatgacttt gtggacaaga ccctgcccga tcagggcgac    1920
aacgataatt ggtggacagg gtggagacag tggattccag ccgggattgg cgtgaccggc    1980
gtgattatcg ccgtgatcgc cctgttctgc atctgcaagt tcgtgttctg a             2031
```

VECTOR COMPRISING MULTIPLE HOMOLOGOUS NUCLEOTIDE SEQUENCES

BACKGROUND OF THE INVENTION

The phenomenon of homologous recombination of nucleic acids involves physical breaking and crosswise rejoining of nucleic acid strands within homologous sequences. Recombination and gene conversion in mammalian cells have been studied by many groups who have monitored the reconstruction of selectable genes after infection with appropriately constructed viral or plasmid substrates. (Chakrabarti et al., Mol. Cell. Biol. 6:2520-2526, 1986). The results of these experiments indicate that cells efficiently support both intra- and intermolecular recombination and gene conversion. (Id.) Intermolecular recombination refers to recombination between homologous sequences present on two different nucleic acid molecules, while intramolecular recombination refers to recombination between homologous sequences present on a single nucleic acid molecule.

Intermolecular recombination can occur between genes in a plasmid or virus and homologous sequences within a cell. (Miller et al., Mol. Cell. Biol. 6:2895-2902, 1986.) This type of recombination can cause the generation of an infectious virus from an attenuated virus. Fuller et al. codon-optimized the separated sequences of the HIV-1 gag and the HIV-1 pol gene to increase its expression in mammalian cells. These optimizations also reduced identity of nucleotides in an overlapping region of about 200 base pairs present in the gag-pol gene of HIV, which also resulted in reduced levels of intermolecular recombination between the gag and pol open reading frames placed on two independent plasmids and the truncated gag gene contained in a recombinant retroviral vector. (Fuller et al., Hum. Gene Ther. 12:2081-2093, 2001.)

Intramolecular recombination can occur with vectors in which duplicated regions of a gene or a gene fragment are present as direct repeats separated by intervening sequences. This type of recombination generally results in the deletion of the intervening sequences and one copy of the repeated sequences. The frequency of intramolecular recombination is generally a great deal higher than for intermolecular recombination.

The level of intramolecular recombination within a plasmid vector has been quantitated in mammalian cells. (Rubnitz and Subrami, Mol. Cell. Biol. 4:2253-2258, 1984.) Depending upon the size of the homologous regions, the frequency of intramolecular recombination within a transfected plasmid DNA varied between 0.306% and 0.002%. (Id.) Low recombination efficiencies were seen with as little as 14 bases of homology. (Id.)

Intramolecular recombination between homologous sequences has been also documented in a number of animal viruses including picornaviruses, influenza virus, adenovirus, and poxviruses. (Gritz et al., J. Virol. 64:5948-5957, 1990). In vaccinia viruses, it has been shown that tandemly duplicated sequences are genetically unstable. (Id.) In viruses, a level of intramolecular recombination has been seen that is much higher than that seen with plasmid vectors.

For example, in a retrovirus, the frequency of recombination between two identical sequences in the same RNA molecule was found to be about 62%. (Zhang et al., J. Virol. 75:6348-6358, 2001). 99% of these recombinations were intramolecular (between two sequences on one RNA molecule), as opposed to intermolecular (between two RNA molecules). (Id.) With adeno-associated virus, intramolecular recombination was also found to be far more efficient than intermolecular recombination. (Choi et al., J. Virol. 79:6801-6807, 2005). Herpes simplex virus type 1 has also been shown to exhibit high levels of recombination. (Dutch et al., J. Virol. 66:277-285.) In poxviruses, a high frequency of homologous recombination has been seen. An experimental system was used to measure recombination in a vaccinia virus by placing a thymidine kinase (tk) gene between two direct repeats of 1.5 kb of DNA. (Ball, J. Virol. 61:1788-1795, 1987.) During each of the first eight passages under non-selective conditions, 40% of tk+ vaccinia viruses lost their tk+phenotype. (Id.) Under non-selective conditions, the tk− virus increased to an abundance of 99.73% of the total virus population. (Id.) Even under selective conditions, recombination occurred with such high frequency that the majority of infectious virus particles that could be isolate from single plaques contained DNA that had already undergone recombination with subsequent loss of the tk gene. (Id.) Using a recombinant vaccinia virus designed to express three heterologous genes, all expressed from VV p7.5-promoters, Howley et al., Gene 172:233-237, 1996, demonstrated recombination between the repeated promoter sequences. A vaccinia virus recombinant designed to contain a C-repeat region (CRR) from the M protein of *Streptococcus pyogenes* contained a complex mixture of variants containing from 1 to more than 20 copies of the CRR. (Hruby et al., P.N.A.S. 88:3190-3194, 1991.)

Although it has been shown that multiple genes with homology of about 60-75% inserted into different insertion sites of MVA resulted in a stable multiple recombinant virus (WO 03/097846), there is, however, a need in the art for compositions and methods that reduce the level of intramolecular recombination in vectors, such as, e.g., viral vectors to allow the generation of stable vectors including multiple homologous nucleotide sequences containing longer stretches of identity.

THE INVENTION

The present invention relates to recombinant vectors and methods for making and using them.

In particular, the present invention encompasses a vector comprising two nucleotide sequences of 300 nucleotides in size each coding for 100 amino acids, wherein the 100 amino acids encoded by each of the two nucleotide sequences have at least 75% amino acid identity and wherein one of the two nucleotide sequences has at least 75 nucleotides different from the other nucleotide sequence, wherein the different nucleotides do not alter the identical amino acids encoded by said two nucleotide sequences.

Surprisingly, it was shown according to the present invention that the risk of intramolecular recombination can not only be significantly reduced, but even be avoided by systematically substituting synonymous codons in at least two similar or identical nucleotide sequences within one nucleic acid molecule, such as, for example a vector, thus leading to the generation of stable vectors containing at least two or more similar or identical nucleotide sequences. Unexpectedly, the strategy employed in the present invention is also applicable to vectors containing three or more similar nucleotide sequences.

The results obtained in the present invention show that it is possible to substitute a high number of nucleotides in nucleotide sequences to reduce intramolecular recombination within a vector, while, surprisingly, at the same time expression of the encoded protein is still retained: When introducing a high number of nucleotide variants into long stretches of a nucleotide sequence as was done according to the present invention, the skilled practitioner would have expected that expression of said sequence or gene would not work properly any more, i.e., it was not expected that the changed nucleotide sequence would remain suitable for efficient expression. The strategy employed herein is not only applicable to short nucleotide sequence stretches of 300 nucleotides, but also to much longer stretches as, e.g., full-length genes which, of course, include a stretch of 300 nucleotides as claimed. The results are applicable to many different genes, vectors and viruses and are highly advantageous for vaccine development, such as for example the development of multivalent vaccines, but may also be advantageous for other technologies as, for example, expression of proteins or for the generation of recombinant cell lines.

In other embodiments, the invention also encompasses methods for the generation of viruses and vectors, and methods for reducing intramolecular recombination.

The invention encompasses a method for generating a vector as described above, said method comprising the steps of a) providing a first nucleotide sequence of 300 nucleotides in size coding for 100 amino acids and b) providing a second nucleotide sequence of 300 nucleotides in size coding for 100 amino acids, wherein the 100 amino acids encoded by each of the two nucleotide sequences have at least 75% amino acid identity and wherein one of the two nucleotide sequences has at least 75 nucleotides different from the other nucleotide sequence, wherein the different nucleotides do not alter the identical amino acids encoded by said two nucleotide sequences; and c) inserting the two divergent nucleotide sequences into a vector.

In a particularly preferred embodiment, the invention encompasses a method for reducing intramolecular recombination within a vector containing two nucleotide sequences of 300 nucleotides in size, each coding for 100 amino acids, wherein the 100 amino acids encoded by each of the two nucleotide sequences have at least 75% amino acid identity, said method comprising substituting nucleotides in one or both nucleotide sequence(s) to generate two divergent sequences which show differences in at least 75 nucleotides, wherein the different nucleotides do not alter the identical amino acids encoded by said two nucleotide sequences.

When using viral vectors, the method reduces the level of intramolecular recombination during each generation of viral propagation. Preferably, the homologous nucleotide sequences recombine in less than 20%, 15%, 10%, 5%, 3%, 2%, 1%, 0.5%, 0.1%, 0.05% or 0.01%, of the progeny viruses per generation.

In another preferred embodiment, the invention encompasses a method for generating a virus, preferably a poxvirus, comprising two homologous nucleotide sequences, said method comprising the steps of a) providing a virus comprising a nucleotide sequence of 300 nucleotides in size coding for 100 amino acids and b) inserting a second nucleotide sequence of 300 nucleotides in size coding for 100 amino acids into the virus; wherein the 100 amino acids encoded by each of the two nucleotide sequences have at least 75% amino acid identity, and wherein one of the two nucleotide sequences has at least 75 nucleotides different from the other nucleotide sequence, wherein the different nucleotides do not alter the identical amino acids encoded by said two nucleotide sequences.

As used herein, a "vector" may be any agent capable of delivering and expressing nucleic acid molecules in a host cell or subject. Thus, a vector may be a PCR product or any piece of nucleic acid introduced into a cell and/or integrated in the cellular genome; or a replicon, such as a plasmid, phage, or cosmid, into which another DNA segment may be inserted so as to bring about the replication of the inserted segment. Generally, a vector may replicate when associated with the proper control elements. Suitable vector backbones for use in the present invention include, for example, those routinely used in the art such as plasmids, viruses, artificial chromosomes, BACs, YACs, or PACs or even recombinant cells like bacteria and eukaryotic cells. The term "vector" includes cloning and expression vectors, as well as viral vectors and integrating vectors. An "expression vector" is a vector that includes a regulatory region. Suitable expression vectors for use in the present invention include, without limitation, plasmids and viral vectors derived from, for example, plant viruses, bacteriophage, baculoviruses, tobacco mosaic virus, retroviruses, and poxviruses. Suitable non viral vectors include plasmids such as pREP4, pCEP4 (Invitrogene), pCI (Promega), pCDM8 (Seed, 1987, Nature 329, 840), pVAX and pgWiz (Gene Therapy System Inc; Himoudi et al, 2002, J. Virol. 76, 12735-12746). Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

In vaccine development, a recombinant virus can be used as the vehicle or vaccine vector for delivering genetic material to a cell. Once in the cell, genetic information is transcribed and translated into proteins, including the inserted antigen targeted against a specific disease. Treatment is successful if the antigen delivered by the vector into the cell induces the body's immune response against the antigen that protects against the disease.

In a preferred embodiment of the present invention, the vector is a plasmid or a viral vector.

A viral vector can be based on an attenuated virus, which cannot replicate in the host, but is able to introduce and express a foreign gene in the infected cell. The virus or the recombinant virus is thereby able to make a protein and display it to the immune system of the host. Some key features of viral vectors are that they can elicit a humoral (B-cell) and/or cell-mediated (T-cell) immune response.

Viral vectors may be obtained from a variety of different viruses. In one embodiment, the virus is an animal virus. The vector may be obtained especially from a virus selected from the group consisting of retrovirus, picornavirus, influenza virus, adenovirus, adeno-associated virus (AAV), poxvirus, herpes virus (e.g., HSV-1), measles virus and foamy virus.

Viral vectors are commonly used by researchers to develop vaccines for the prevention and treatment of infectious diseases and cancer. Of these, poxviruses (including canary pox, vaccinia, and fowl pox) are belonging to the group of the most common vector vaccine candidates. Poxviruses are a preferred choice for transfer of genetic material into new hosts due to the relatively large capacity for insertion of sequences into the viral genome and because of their ability to replicate their genomes and perform transcription in the infected cell's cytoplasm instead of the nucleus, thereby minimizing the risk of insertional mutagenesis by integrating genetic material into the genome of the host cell as seen with other vectors, e.g. retroviral vectors. The virions of poxviruses are large as compared to most other animal viruses (for more details see Fields et al., eds., Virology, 3rd Edition, Volume 2, Chapter 83, pages 2637 ff).

In a preferred embodiment of the invention, the viral vector is derived from a poxvirus (see for example Cox et al.

in "Viruses in Human Gene Therapy" Ed J. M. Hos, Carolina Academic Press). It may be obtained from any member of the poxviridae and may be, in particular an avipoxvirus or an orthopoxvirus.

Examples for avipoxviruses suitable for use in the present invention include any avipoxvirus such as Fowlpoxvirus, Canarypoxvirus, Uncopoxvirus, Mynahpoxvirus, Pigeonpoxvirus, Psittacinepoxvirus, Quailpoxvirus, Peacockpoxvirus, Penguinpoxvirus, Sparrowpoxvirus, Starlingpoxvirus and Turkeypoxvirus. Preferred avipoxviruses are Canarypoxvirus and Fowlpoxvirus.

Avipoxviruses are naturally host-restricted and productively replicate only in avian species and cells (Taylor et al., Biological and immunogenic properties of a canarypox-rabies recombinant, ALVAC-RG (vCP65) in non-avian species, Vaccine 13 :539-549, 1995). If human cells are infected with an avipoxvirus, heterologous genes are expressed from the viral genome. However, the avipoxvirus does not fully replicate in the human cells and there is, thus, no risk that the human being is harmed by productive virus replication. Various recombinant avipoxviruses have been constructed that express e.g. lentiviral gene products (U.S. Pat. No. 5,766,598), cytokines and/or tumor-associated antigens (U.S. Pat. No. 5,833,975) or rabies G glycoprotein (Taylor et al., Biological and immunogenic properties of a canarypox-rabies recombinant, ALVAC-RG (vCP65) in non-avian species, Vaccine 13: 539-549, 1995). A recombinant canarypox virus expressing the four HIV genes gag, pol, env and nef has already been used in clinical trials (Peters, B. S., The basis for HIV immunotherapeutic vaccines, Vaccine 20: 688-705, 2001).

Since avipoxviruses productively replicate only in avian cells, these cells have to be used for the amplification of the virus and for the generation of recombinant viruses.

An example for a canarypox virus is strain Rentschler. A plaque purified Canarypox strain termed ALVAC (U.S. Pat. No. 5,766,598) was deposited under the terms of the Budapest treaty with the American Type Culture Collection (ATCC), accession number VR-2547. Another Canarypox strain is the commercial canarypox vaccine strain designated LF2 CEP 524 24 10 75, available from Institute Merieux, Inc.

Examples of a Fowlpox virus are strains FP-1, FP-5 and TROVAC (U.S. Pat. No. 5,766,598). FP-1 is a Duvette strain modified to be used as a vaccine in oneday old chickens. The strain is a commercial fowlpox virus vaccine strain designated 0 DCEP 25/CEP67/2309 October 1980 and is available from Institute Merieux, Inc. FP-5 is a commercial fowlpox virus vaccine strain of chicken embryo origin available from American Scientific Laboratories (Division of Schering Corp.) Madison, Wis., United States Veterinary License No. 165, serial No. 30321.

Of the poxviruses, the vaccinia and variola species are the two best known. Variola virus is the cause of smallpox. In contrast to variola virus, vaccinia virus does not normally cause systemic disease in immune-competent individuals and it has therefore been used as a live vaccine to immunize against smallpox. Successful worldwide vaccination with vaccinia virus culminated in the eradication of smallpox as a natural disease in the 1980s (The global eradication of smallpox. Final report of the global commission for the certification of smallpox eradication; History of Public Health, No. 4, Geneva: World Health Organization, 1980). Since then, vaccination has been discontinued for many years, except for people at high risk of poxvirus infections (for example, laboratory workers). However, there is an increasing fear that, for example, variola causing smallpox may be used as a bio-terror weapon. Furthermore, there is a risk that other poxviruses such as cowpox, camelpox, and monkeypox may potentially mutate, through selection mechanisms, and obtain similar phenotypes as variola. Several governments are therefore building up stockpiles of vaccinia-based vaccines to be used either pre-exposure (before encounter with variola virus) or post-exposure (after encounter with variola virus) of a presumed or actual smallpox attack.

In a particular preferred embodiment of the invention, the vector is a vaccinia virus vector.

Vaccinia virus is highly immune-stimulating and provokes strong B-(humoral) and T-cell mediated (cellular) immunity to both, its own gene products and to many foreign gene product expressed from genes inserted in the vaccinia genome. Vaccinia virus is, therefore, seen as an ideal vector for vaccines against smallpox and other infectious diseases and cancer in the form of recombinant vaccines. Many of the recombinant vaccinia viruses described in the literature are based on the fully replication competent Western Reserve strain of Vaccinia virus. However, it is known that this strain has a high neurovirulence and is, thus, poorly suited for use in humans and animals (Morita et al. 1987, Vaccine 5, 65-70).

A suitable vaccinia virus can be selected from the group consisting of the Copenhagen strain (Goebel et al., 1990, Virol. 179, 247-266 and 517-563; Johnson et al., 1993, Virol. 196, 381-401), the Wyeth strain, NYVAC (see WO92/15672 and Tartaglia et al., 1992, Virology 188, 217-232) and the highly attenuated modified Ankara (MVA) strain (Mayr et al., 1975, Infection 3, 6-16).

A preferred example of a suitable vaccinia virus is the highly attenuated vaccinia virus strain NYVAC, which was derived from a plaque-cloned isolate of the Copenhagen vaccine strain by deletion of 18 ORFs from the viral genome (Tartaglia et al., NYVAC: A highly attenuated strain of vaccinia virus, Virology 188, 217-232, 1992). NYVAC is characterized by a dramatically reduced ability to replicate on a variety of human tissue culture cells, but retains the ability to induce strong immune responses to extrinsic antigens.

All of the above-described viruses are equally suitable for use in the present invention.

In a most preferred embodiment of the invention, the virus is a modified vaccinia virus Ankara (MVA) which is known to be exceptionally safe in vaccinations.

Modified Vaccinia virus Ankara (MVA) virus is related to Vaccinia virus, a member of the genus Orthopoxvirus in the family Poxviridae. MVA has been generated by 516 serial passages on chicken embryo fibroblasts of the dermal vaccinia strain Ankara (Chorioallantois vaccinia virus Ankara, CVA) (for review see Mayr, A., et al., Passage History: Abstammung, Eigenschaften and Verwendung des attenuierten Vaccinia-Stammes MVA, Infection 3, 6-14, 1975). As a consequence of these long-term passages the resulting MVA virus deleted about 31 kilobases of its genomic sequence and, therefore, was described as highly host cell restricted to avian cells (Meyer, H. et al., Mapping of deletions in the genome of the highly attenuated vaccinia virus MVA and their influence on virulence, J. Gen. Virol. 72, 1031-1038, 1991; (Meisinger-Henschel et al., Genomic sequence of chorioallantois vaccinia virus Ankara, the ancestor of modified vaccinia virus Ankara, J. Gen. Virol. 88, 3249-3259, 2007). It was shown, in a variety of animal models that the resulting MVA was significantly avirulent (Mayr, A. & Danner, K. Vaccination against pox diseases under immunosuppressive conditions, Dev. Biol. Stand. 41:

225-34, 1978). Additionally, this MVA strain has been tested in clinical trials as vaccine to immunize against the human smallpox disease (Mayr et al., Zbl. Bakt. Hyg. I, Abt. Org. B 167, 375-390 [1987], Stickl et al., MVA vaccination against smallpox: clinical tests with an attenuated live vaccinia virus strain (MVA) (author's transl), Dtsch. med. Wschr. 99, 2386-2392, 1974). These studies involved over 120,000 humans, including high risk patients, and proved that, compared to Vaccinia based vaccines, MVA had diminished virulence or infectiousness while it maintained good immunogenicity.

The invention encompasses recombinant MVA viruses generated with any and all MVA viruses. An example for an MVA strain is deposit VR-1508, deposited at the American Type Culture collection (ATCC), Manassas, Va. 20108, USA. In another embodiment the MVA-Vero strain or a derivative thereof can be used according to the present invention. The strain MVA-Vero has been deposited at the European Collection of Animal Cell Cultures under the deposition number ECACC V99101431 and ECACC 01021411. Further examples for MVA virus strains used according to the present invention are strains MVA 572 and 575 deposited at the European Collection of Animal Cell Cultures (ECACC), Salisbury (UK) with the deposition number ECACC V94012707 and ECACC V00120707, respectively. Particularly preferred MVA viruses are MVA variant strains MVA-BN® as, e.g., deposited at ECACC under number V00083008, and derivatives having the same properties as MVA-BN®.

MVA-BN® is a virus used in the manufacturing of a stand-alone third generation smallpox vaccine. MVA-BN® was developed by further passages from MVA strain 571/572. To date, more than 1500 subjects including subjects with atopic dermatitis (AD) and HIV infection have been vaccinated in clinical trials with MVA-BN® based vaccines.

Derivatives having the same properties as the deposited strain of MVA-BN® have the capability of reproductive replication in vitro in chicken embryo fibroblasts (CEF), but no capability of reproductive replication in human cells in which MVA 575 or MVA 572 can reproductively replicate. Most preferably, the MVA has no capability of reproductive replication in the human keratinocyte cell line HaCaT, the human embryo kidney cell line 293, the human bone osteosarcoma cell line 143B, and the human cervix adenocarcinoma cell line HeLa.

The term "not capable of reproductive replication" is used in the present application as defined in WO 02/42480 and U.S. Pat. No. 6,761,893, respectively. Thus, said term applies to a virus that has a virus amplification ratio at 4 days after infection of less than 1 using the assays described in U.S. Pat. No. 6,761,893, which assays are hereby incorporated by reference. The "amplification ratio" of a virus is the ratio of virus produced from an infected cell (Output) to the amount originally used to infect the cells in the first place (Input). A ratio of "1" between Output and Input defines an amplification status wherein the amount of virus produced from the infected cells is the same as the amount initially used to infect the cells.

In a most preferred embodiment, the MVA strain used in the present invention is MVA-BN® or a derivative as described above. The features of MVA-BN®, the description of biological assays allowing evaluating whether an MVA strain is MVA-BN® or a derivative thereof and methods allowing to obtain MVA-BN® or an MVA having the properties of MVA-BN® are disclosed in WO 02/42480. The content of this application is included in the present application by reference. The highly attenuated MVA-BN® virus can be derived, e.g., by the further passage of a modified vaccinia virus Ankara (MVA), such as MVA-572 or MVA-575 and, optionally, by plaque or clone purification. MVA-BN® lacks approximately 13% (26.5 kb from six major and multiple minor deletion sites) of the genome compared with ancestral CVA virus. The deletions affect a number of virulence and host range genes, as well as a large fragment of the gene coding for A-type inclusion protein (ATI) and a gene coding for a structural protein directing mature virus particles into A-type inclusion bodies.

In particular, reference is made to the definition of the properties of the MVA according to the invention as described in WO 02/42480, such as the properties of MVA-BN® and the properties and definitions of the derivates of MVA-BN®. Said reference also discloses how MVA and other vaccinia viruses can be propagated. Briefly, eukaryotic cells are infected with the virus. The eukaryotic cells are cells that are susceptible to infection with the respective poxvirus and allow replication and production of infectious virus. For MVA an example for this type of cells are chicken embryo fibroblasts (CEF) and BHK cells (Drexler et al., Highly attenuated modified vaccinia Ankara replicates in baby hamster kidney cells, a potential host for virus propagation, but not in various human transformed and primary cells, J. Gen. Virol. 79, 347-352, 1998). CEF cells can be cultivated under conditions known to the person skilled in the art. Preferably the CEF cells are cultivated in serum-free medium in stationary flasks or roller bottles. The incubation preferably takes place 48 to 96 hours at 37° C. For the infection MVA is preferably used at a multiplicity of infection (MOI) of 0.05 to 1 $TCID_{50}$ and the incubation preferably takes place 48 to 72 hours at 37° C.

The viruses as used according to the invention can be propagated on various cell cultures, particularly animal cell cultures. The virus is allowed to infect susceptible cell cultures and reproductively replicate. Progeny viruses are collected by routine techniques in the art.

For example, with MVA viruses and other vaccinia viruses, chicken embryo fibroblasts (CEFs) in serum-containing or serum-free medium can be infected with the viruses. After the virus has been allowed to reproductively replicate, progeny viruses are collected.

The present invention also relates to a recombinant poxvirus, preferably vaccinia virus, in particular MVA, capable of expressing two or more homologous nucleotide sequences, in particular coding sequences. The virus can contain two, three, four or more homologous nucleotide coding sequences.

The vector of the present invention comprises two nucleotide sequences of 300 nucleotides in size. In a preferred embodiment, the vector comprises three, four, five, six or more nucleotide sequences, which, of course, encompass also two nucleotide sequences as claimed. 300 nucleotides may, of course, also be part of a longer nucleotide sequence.

Additionally, in various embodiments, the two or more nucleotide sequences are 300, 350, 400, 450, 500, 600, 700, 800, 900, 1000, 1500, 2000, 2500, or 3000 or even more nucleotides in size which may all be part of longer nucleotide sequences and which, of course, all include 300 nucleotides as claimed.

As used herein, the terms "polynucleotide", "nucleotide sequence", "nucleic acid", "nucleic acid molecule" "nucleic acid sequence" are used interchangeable and define a polymer of either polydeoxyribonucleotides (DNA) or polyribonucleotides (RNA) molecules or any combination thereof. The definition encompasses single or double-stranded, linear or circular, naturally occurring or synthetic polynucleotides.

The nucleotide sequences of the present invention may be coding sequences and can contain complete genes, respectively. The term "coding sequence", as used herein, refers to a nucleotide sequence that codes for a specific amino acid sequence. Non-coding sequences of genes include introns and control regions, such as promoters, operators, and terminators.

The nucleotide sequences can also contain gene fragments. The nucleotide sequences can contain synthetic sequences, such as nucleotide sequences encoding amino acid linker sequences or epitopes. The nucleotide sequences can be composed of a mixture of genes, gene fragments, and synthetic sequences. The nucleotide sequence may also contain analogs such as nucleotide analogs, phosphate ester analog and/or pentose sugar analog. Also included within the definition of nucleotide analogs are nucleotides in which the phosphate ester and/or sugar phosphate ester linkages are replaced with other types of linkages, such as N-(2-aminoethyl)-glycine amides and other amides (see, e.g., Nielsen et al., 1991, Science 254: 1497-1500; WO 92/20702; U.S. Pat. No. 5,719,262; U.S. Pat. No. 5,698,685); morpholinos (see, e.g., U.S. Pat. No. 5,698,685; U.S. Pat. No. 5,378,841; U.S. Pat. No. 5,185,144); carbamates (see, e.g., Stirchak & Summerton, 1987, J. Org. Chem. 52: 4202); methylene(methylimino) (see, e.g., Vasseur et al., 1992, J. Am. Chem. Soc. 114: 4006); 3'thioformacetals (see, e.g., Jones et al., 1993, J. Org. Chem. 58: 2983); sulfamates (see, e.g., U.S. Pat. No. 5,470,967); 2-aminoethylglycine, commonly referred to as PNA (see, e.g., Buchardt, WO 92/20702; Nielsen (1991) Science 254:1497-1500); and others (see, e.g., U.S. Pat. No. 5,817,781; Frier & Altman, 1997, Nucl. Acids Res. 25:4429 and the references cited therein). Phosphate ester analogs include, but are not limited to, (i) C1-C4 alkylphosphonate, e.g. methylphosphonate; (ii) phosphoramidate; (iii) C1-C6 alkyl-phosphotriester; (iv) phosphorothioate; and (v) phosphorodithioate.

Further modifications include chemical modifications (e.g. see WO 92/03568; U.S. Pat. No. 5,118,672) in order to increase the in vivo stability of the nucleic acid, enhance the delivery thereof, or reduce the clearance rate from the host subject.

Furthermore, in one embodiment, the nucleotide sequence can contain fusion genes, artificial genes and polyepitopes.

A fusion gene, as denoted herein, is a hybrid gene formed from two previously separate genes, gene fragments or artificial DNA or epitopes. It can occur as the result of a translocation, interstitial deletion, or inversion.

A fusion gene can be constructed by linking at least two DNA fragments, wherein the DNA fragments encode identical or different amino acid sequences Fusion proteins may facilitate the expression and/or purification of proteins. For example, a polypeptide of the invention may be generated as a glutathione-S-transferase (GST) fusion protein. Such GST fusion proteins may be used to simplify purification of a polypeptide of the invention, such as through the use of glutathione-derivatized matrices (see, for example, Current Protocols in Molecular Biology, eds. Ausubel et al., (N.Y.: John Wiley & Sons, 1991)). In another embodiment, a fusion gene coding for a purification leader sequence, such as a poly-(His)/enterokinase cleavage site sequence at the N-terminus of the desired portion of the recombinant protein, may allow purification of the expressed fusion protein by affinity chromatography using a Ni2+ metal resin. The purification leader sequence may then be subsequently removed by treatment with enterokinase to provide the purified protein (e.g., see Hochuli et al., (1987) J. Chromatography 411: 177; and Janknecht et al., PNAS USA 88:8972). Further heterologous sequences encoding a polypeptide permitting the detection, isolation, solubilization and/or stabilization of the polypeptide to which it is fused, include poly His tag, myc, HA, protein A, protein G, calmodulin-binding peptide, thioredoxin, maltose-binding protein, poly arginine, poly His-Asp, FLAG, a portion of an immunoglobulin protein, and a transcytosis peptide.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene may be synthesized by conventional techniques including automated DNA synthesizers. Alternatively, PCR amplification of gene fragments may be carried out using anchor primers which give rise to complementary overhangs between two consecutive gene fragments which may subsequently be annealed to generate a chimeric gene sequence (see, for example, Current Protocols in Molecular Biology, eds. Ausubel et al., John Wiley & Sons: 1992) and by fusion PCR wherein two or more polynucleotides are sharing a stretch of identity, which in a PCR reaction can result in fused polynucleotide sequences.

In another preferred embodiment, the nucleotide sequence of the present invention encodes a polyepitope. A polyepitope is a chimeric protein containing isolated epitopes from at least one protein/antigen, preferably from more than one protein/antigen.

Said epitopes can be "isolated" or "biologically pure". The term "isolated" refers to material that is substantially free from components that normally accompany it as found in its naturally occurring environment. An "isolated" epitope refers to an epitope that does not include the neighbouring amino acids of the whole sequence of the antigen or protein from which the epitope was derived.

With regard to a particular amino acid sequence, an "epitope" is a set of amino acid residues which is involved in recognition by a particular immunoglobulin, or in the context of T cells, those residues necessary for recognition by T cell receptor proteins and/or Major Histocompatibility Complex (MHC) molecules. The term "peptide" designates a series of amino acids, connected one to the other, typically by peptide bonds between the amino and carboxyl groups of adjacent amino acids.

The epitopes are of a certain length and bind to a molecule functioning in the immune system, preferably a HLA class I and a T-cell receptor. The epitopes in a polyepitope construct can be HLA class I epitopes and optionally HLA class II epitopes. HLA class I epitopes are referred to as CTL epitopes and HLA class II epitopes are referred to as HTL epitopes. Some polyepitope constructs can have a subset of HLA class I epitopes and another subset of HLA class II epitopes. A CTL epitope usually consists of 13 or less amino acid residues in length, 12 or less amino acids in length, or 11 or less amino acids in length, preferably from 8 to 13 amino acids in length, most preferably from 8 to 11 amino acids in length (i.e. 8, 9, 10, or 11). A HTL epitope consists of 50 or less amino acid residues in length, and usually from 6 to 30 residues, more usually from 12 to 25, and preferably consists of 15 to 20 (i.e. 15, 16, 17, 18, 19, or 20) amino acids in length. The polyepitope construct of the present invention preferably includes 2 or more, 5 or more, 10 or more, 13 or more, 15 or more, 20 or more, or 25 or more CTL epitopes. More specific, the polyepitope construct comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60 or more CTL epitopes.

The homologous nucleotide sequences according to the present invention can be derived from any organism, microorganism, such as any virus, any bacterium, any fungus or parasite. The homologous nucleotide sequences can be either heterologous to the sequence of the vector, but also homologous thereto: When, for example, a virus is used as a vector, also viral own nucleotide sequences can be multiplied according to the present invention, for example, in order to overexpress a protein of the virus for getting enhanced immune reactivity or safety. Preferably, the homologous nucleotide sequences are derived from an infectious or pathogenic microorganism and most preferably from different strains or clades, variants, subtypes or serotypes of said microorganism. The terms "strain" or "clade" are technical terms, well known to the practitioner, referring to the taxonomy of microorganisms. The taxonomic system classifies all so far characterised microorganisms into the hierarchic order of Families, Genera, Species, Strains (Fields Virology, ed. by Fields B. N., Lippincott-Raven Publishers, 4th edition 2001). While the criteria for the members of Family is their phylogenetic relationship, a Genera comprises all members which share common characteristics, and a Species is defined as a polythetic class that constitutes a replicating lineage and occupies a particular ecological niche. The term "strain" or "clade" describes a microorganism, i.e. virus, which shares the common characteristics, like basic morphology or genome structure and organisation, but varies in biological properties, like host range, tissue tropism, geographic distribution, attenuation or pathogenicity. The term "variants" or "serotypes" further distinguishes between members of the same strain, also called subtypes, which show individual infection spectra or antigenic properties due to minor genomic variations.

According to a further embodiment of the present invention the homologous nucleotide sequences are preferably selected from viruses. Representative examples of viruses include without limitation HIV (HIV-I or HIV-2), herpes viruses (e.g. HSVI or HSV2), cytomegalovirus (CMV), Epstein Barr virus (EBV), hepatitis viruses (e.g. hepatitis A virus (HAV), HBV, HCV and hepatitis E virus), flaviviruses (e.g. Yellow Fever Virus), varicella-zoster virus (VZV), paramyxoviruses, respiratory syncytial viruses (RSV), parainfluenza viruses, measles virus, influenza viruses, and papillomaviruses.

According to another embodiment, the homologous nucleotide sequences are selected from Dengue virus genes. Most preferred are homologous genes derived from different serotypes of the virus, wherein said genes may be derived from one, two, three or from all of the 4 Dengue virus serotypes.

In a preferred embodiment, the two homologous nucleotide sequences encode respiratory syncitial virus (RSV) genes. In a preferred embodiment, the homologous nucleotide sequences encode RSV-F and/or RSV-G proteins. Preferably, one of the RSV genes is full-length and the other is truncated.

In another preferred embodiment, the two, preferably three homologous nucleotide sequences encode Ebola virus (EBOV) proteins. Three homologous nucleotide sequences encoding Ebola virus (EBOV) proteins do, of course, also cover two homologous nucleotide sequences. In a preferred embodiment, the homologous nucleotide sequences encode EBOV glycoproteins (GP). In a particular preferred embodiment, the nucleotide sequences encode glycoprotein precursor proteins from the EBOV strains EBOV-B (Bundibugyo), EBOV-S (Sudan ebolavirus strain Gulu) and EBOV-Z (Zaire ebola virus strain Mayinga).

In another embodiment, the homologous nucleotide sequences are selected from bacteria. Representative examples of suitable bacteria include without limitation *Neisseria* (e.g. *N. gonorrhea* and *N. meningitidis*); *Bordetella* (e.g. *B. pertussis, B. parapertussis* and *B. bronchiseptica*), *Mycobacteria* (e.g. *M. tuberculosis, M. bovis, M. leprae, M. avium, M. paratuberculosis, M. smegmatis*); *Legionella* (e.g. *L. pneumophila*); *Escherichia* (e.g. enterotoxic *E. coli*, enterohemorragic *E. coli*, enteropathogenic *E. coli*); *Shigella* (e.g. *S. sonnei, S. dysenteriae, S. flexnerii*); *Salmonella* (e.g. *S. typhi, S. paratyphi, S. choleraesuis, S. enteritidis*); *Listeria* (e.g. *L. monocytogenes*); *Helicobacter* (e.g. *H. pylori*); *Pseudomonas* (e.g. *P. aeruginosa*); *Staphylococcus* (e.g. *S. aureus, S. epidermidis*); *Enterococcus* (e.g. *E. faecalis, E. faecium*); *Bacillus* (e.g. *B. anthracis*); *Corynebacterium* (e.g. *C. diphtheriae*), and *Chlamydia* (e.g. *C. trachomatis, C. pneumoniae, C. psittaci*). Representative examples of parasites include without limitation *Plasmodium* (e.g. *P. falciparum*); *Toxoplasma* (e.g. *T. gondii*); *Leshmania* (e.g. *L. major*); *Pneumocystis* (e.g. *P. carinii*); and *Schisostoma* (e.g. *S. mansoni*). Representative examples of fungi include without limitation *Candida* (e.g. *C. albicans*) and *Aspergillus*.

The at least two nucleotide sequences can be of the same size or of different sizes. In a preferred embodiment, one of the two nucleotide sequences is truncated relative to the other. The truncation can be at the 5' or 3' end.

In various embodiments, the 300 nucleotides of the two nucleotide sequences encode 100 amino acids, which have at least 75%, 80%, 85%, 90%, 95%, 98%, 99%, or 100% amino acid identity. In a preferred embodiment, said amino acid identity is within a stretch of 100, 125, 150, 175, 200, 250, 300, 350, 400, 450, 500, 600, 700, 800, 900 or 1000 or more contiguous amino acids.

In a particular preferred embodiment, the amino acids have at least 75%, 80%, 85%, 90%, 95%, 98%, 99%, or 100% amino acid identity within a stretch of at least 150 or 200 contiguous amino acids.

In other preferred embodiments, the proteins encoded by the two nucleotide sequences have at least 75%, 80%, 85%, 90%, 95%, 98%, 99%, or 100% amino acid identity within a stretch of 300 or 500 contiguous amino acids. In other preferred embodiments, the proteins encoded by the at least two nucleotide sequences have 85%-100%, in particular 100% amino acid identity within a stretch of 100, 200, 400, 600, or 800 contiguous amino acids in pairwise comparison.

As used herein, any term referring to "percent sequence identity", such as "amino acid identity" refers to the degree of identity between any given query sequence and a subject sequence.

Specifically, the following terms are used to describe the sequence relationships between two or more nucleic acids, polynucleotides or amino acid sequences: "reference sequence", "comparison window", "sequence identity", "percentage of sequence identity", and "substantial identity". A "reference sequence" is a defined sequence used as a basis for a sequence comparison; a reference sequence may be a subset of a larger sequence.

The terms "identical" or percent "identity," in the context of two or more nucleic acids or polypeptide sequences, refer to two or more sequences or subsequences that are the same or have a specified percentage of amino acid residues or nucleotides that are the same (e.g., 75% identity, 80% identity, 85% identity, 90% identity, 99%, or 100% identity in pairwise comparison), when compared and aligned for maximum correspondence over a comparison window, or designated region as measured using a sequence comparison algorithm or by manual alignment and visual inspection. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity.

The phrase "substantially identical", in the context of two nucleic acids or polypeptides, refers to two or more sequences or subsequences that have at least about 85%, identity, at least about 86%, 87%, 88%, 89%, 90%, 91%, 92%, 93%, 94%, 95%, 96%, 97%, 98%, 99%, or 100% nucleotide or amino acid residue identity, when compared and aligned pairwise for maximum correspondence, as measured using a sequence comparison algorithm or by visual inspection. In an exemplary embodiment, the substantial identity exists over a region of the sequences that is at least about 50 residues in length. In another exemplary embodiment, the substantial identity exists over a region of the sequences that is at least about 100 residues in length. In still another exemplary embodiment, the substantial identity exists over a region of the sequences that is at least about 150 residues or more, in length. In one exemplary embodiment, the sequences are substantially identical over the entire length of nucleic acid or protein sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually 20 to 50, about 50 to about 100, about 100 to about 200, more usually about 100 to about 150, or of about 20, 50, 100, 150, 200, 250, 300, 350, 400, 450, 500, 600, 700, 800, 900, 1000, 1500, 2000, 2500, or 3000 or even more in which a sequence may be compared to a reference sequence of the same number of contiguous positions after the two sequences are optimally aligned.

Percent identity can be determined using the alignment method of Needleman and Wunsch (J. Mol. Biol. 48; 443-453 (1970)) that has been shown to be equivalent to Sellers (SIAM J. of Applied Math 26; 787-793 (1974). The percent identity may be determined, for example, by comparing sequence information using the GAP computer program, version 6.0 described by Devereux et al. (Nucl. Acids Res. 12:387, 1984) and available from the University of Wisconsin Genetics Computer Group (UWGCG), which utilizes this alignment method. The preferred default parameters for the GAP program include: (1) a unary comparison matrix (containing a value of 1 for identities and 0 for non-identities) for nucleotides, and the weighted comparison matrix of Gribskov and Burgess, Nucl Acids Res. 14:6745, 1986, as described by Schwartz and Dayhoff, eds., Atlas of Protein Sequence and Structure, National Biomedical Research Foundation, pp. 353-358, 1979; (2) a penalty of 3.0 for each gap and an additional 0.10 penalty for each symbol in each gap; and (3) no penalty for end gaps. An other suitable tool is to use the ContigExpress from the VectorNTI Advance program (INVITROGEN), e.g. version 10.3.1 from 2007.

According to the present invention, the degeneracy of the genetic code is used to make homologous or identical nucleotide sequences less homologous in order to prevent intramolecular recombination. Said differences may already be included in the nucleotide sequences by nature and/or are included artificially by substitutions. In various embodiments, the number of different nucleotides originating from nature plus from artificial substitution is at least 75, 80, 85, 90, 95, 100, 125, 150, 175, 200, 250, 300, 350, 400, 450, or 500. Preferably, the number of different bases is at least 75, 200 or 450. The number of differences does, of course, vary and increase, respectively, with the number of nucleotides of the nucleotide sequences.

In a preferred embodiment, at least 75, 80, 85, 90, 95, 100, 125, 150, 175, 200, 250, 300, 350, 400, 450, or 500 nucleotides are substituted. Said substitutions are artificially introduced independently of already present numbers of different nucleotides included, for example, by silent mutations.

In various embodiments, two nucleotide sequences with stretches of identity of no more than 13, 12, 11, 10, 9, 8, 7, 6, 5, or 4 contiguous nucleotides after substitution are preferred. In case of more than two nucleotide sequences, stretches of identity of no more than 20, 19, 18, 17, 16, 15, 14, 13, 12, 11, 10, 9, 8, 7, 6, 5 or 4 contiguous nucleotides after subsititution are preferred.

In another embodiment, the nucleotide sequences can have at least 75, 100, 150, 200, 250, 300, 350, 400, or 450 nucleotides substituted out of 300, 400, 500, 600, 700, 800, 900, 100, 1100, 1200, 1300, 1400, 1500, or 1600 or more nucleotides.

In the context of this invention, substitution of nucleotides with different nucleotides means the technical or artificial replacement of nucleotides by other nucleotides. Preferably, the substituted nucleotides do not alter the encoded amino acid sequence. Substitution can be performed by identifying codons in the two homologous nucleotide sequences encoding the same amino acids and altering codons in one of the two homologous nucleotide sequences such that the codons still encodes the same amino acids. The alterations can be made in one, both or all of the homologous nucleotide sequences.

For example the amino acid proline is encoded by the codons CCA, CCC, CCG and CCU (on the DNA level the U is replaced by a T). A simple nucleotide sequence, CCCCCC, initially encoding two prolines in two homologous nucleotide sequences could be changed to CCACCG, also encoding two prolines, in one of the two homologous nucleotide sequences. Alternatively, one of the sequences encoding proline-proline could be changed to CCCCCG, and the other to CCACCC.

A more complicated example is the amino acid serine, which is encoded by UCA, UCC, UCG, UCU, AGC and AGU. Similarly, UCAUCA, initially encoding two different serines could be changed in multiple homologous sequences, to AGCAGC (sharing no common nucleotide with UCAUCA) and UCGAGU (sharing only one position with UCAUCA or two position with AGCAGC) and so on.

This allows a higher flexibility in introducing different nucleotide variants into two or more nucleotide sequences encoding a serine-serine.

Preferably codon optimization as described in the present invention avoids the use of rare codons for a desired host since rare codons may block or reduce expression of the encoded protein. Also, substitutions that may introduce nucleic acid signals for the desired host are preferably avoided. Such signals include, but are not limited to, splice signals, termination signals, and initiation signals. Preferably, the following sequence motifs may be avoided depending on the type of vector used, e.g., the vaccinia virus early transcription termination signal needs not to be avoided in many other vectors, being no poxvirus vectors:

internal TATA-boxes, chi-sites, and ribosomal entry sites;
AT-rich and GC-rich sequence stretches;
ARE, INS, and CRS sequence elements;
repeat sequences and RNA secondary structures;
(cryptic) splice donor and acceptor sites, and branch points; and
vaccinia early transcription termination signals: (TTTTTNT).

BRIEF DESCRIPTION OF THE DRAWINGS

The invention is more fully understood with reference to the drawings, in which:

FIG. 1 depicts an alignment of the nucleotide sequence encoding the full-length RSV-F (F) protein (SEQ ID NO:1) with the nucleotide sequence encoding the substituted, truncated RSV-F_trunc (F_trunc) protein (SEQ ID NO:2). The identical sequences are highlighted in black, and the substituted nucleotides remain unhighlighted. The locations of primers A1 and B2 are indicated.

FIG. 2 depicts an alignment of the full-length RSV-F (F) protein (SEQ ID NO:3) with the truncated RSV-F_trunc (F_trunc) protein (SEQ ID NO:4). The full length sequence of RSV-F is truncated by 50 aa to result in the truncated RSV-F_trunc protein. The RSV-F_trunc protein covers approximately 91% of the full length protein.

FIGS. 5A-C depict the hypothetical recombination $F/F_{trunc}$ between the full lengthRSV-F gene (F) and the truncated F gene ($F_{trunc}$) in the double recombinant MVA and the locations of the PCR primers in the recombinant and non-recombinant viruses and control plasmids. A. MVA-mBN175B. B. pMISC173. C. pMISC172.

FIG. 7 depicts an alignment of three EBOV (ebolavirus) GP (glycoprotein) protein sequences. The amino acid sequences of three GP proteins of the ebola virus strains EBOV-B (SEQ ID NO:5), EBOV-S(SEQ ID NO:6), and EBOV-Z (SEQ ID NO:7) are aligned. No gaps were allowed in the alignment. The overall identity in all three protein sequences is 48.5%. Gray background: identical in all three protein sequences. Black background: identical in two proteins.

Figure 8A:
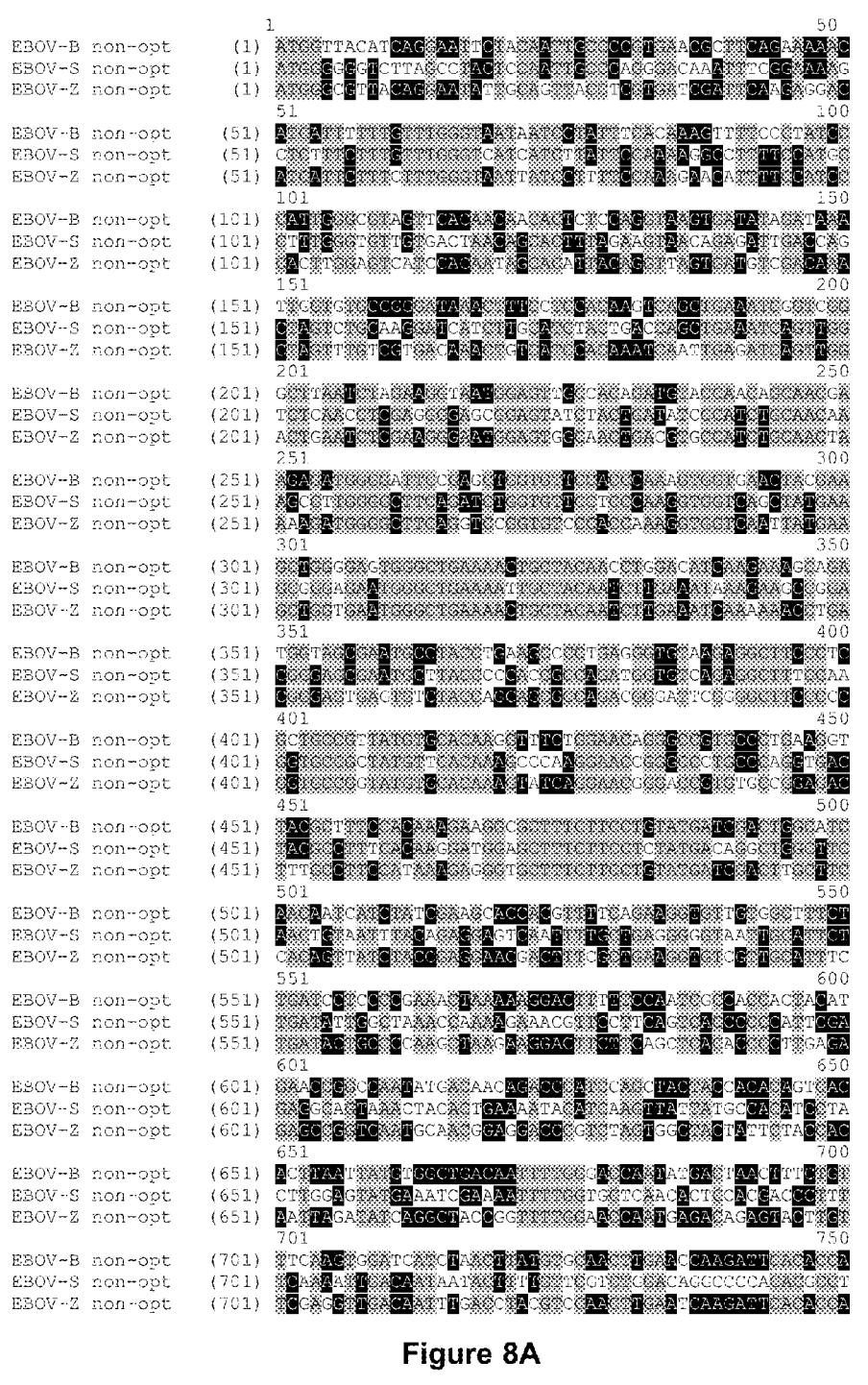
Figure 8A:
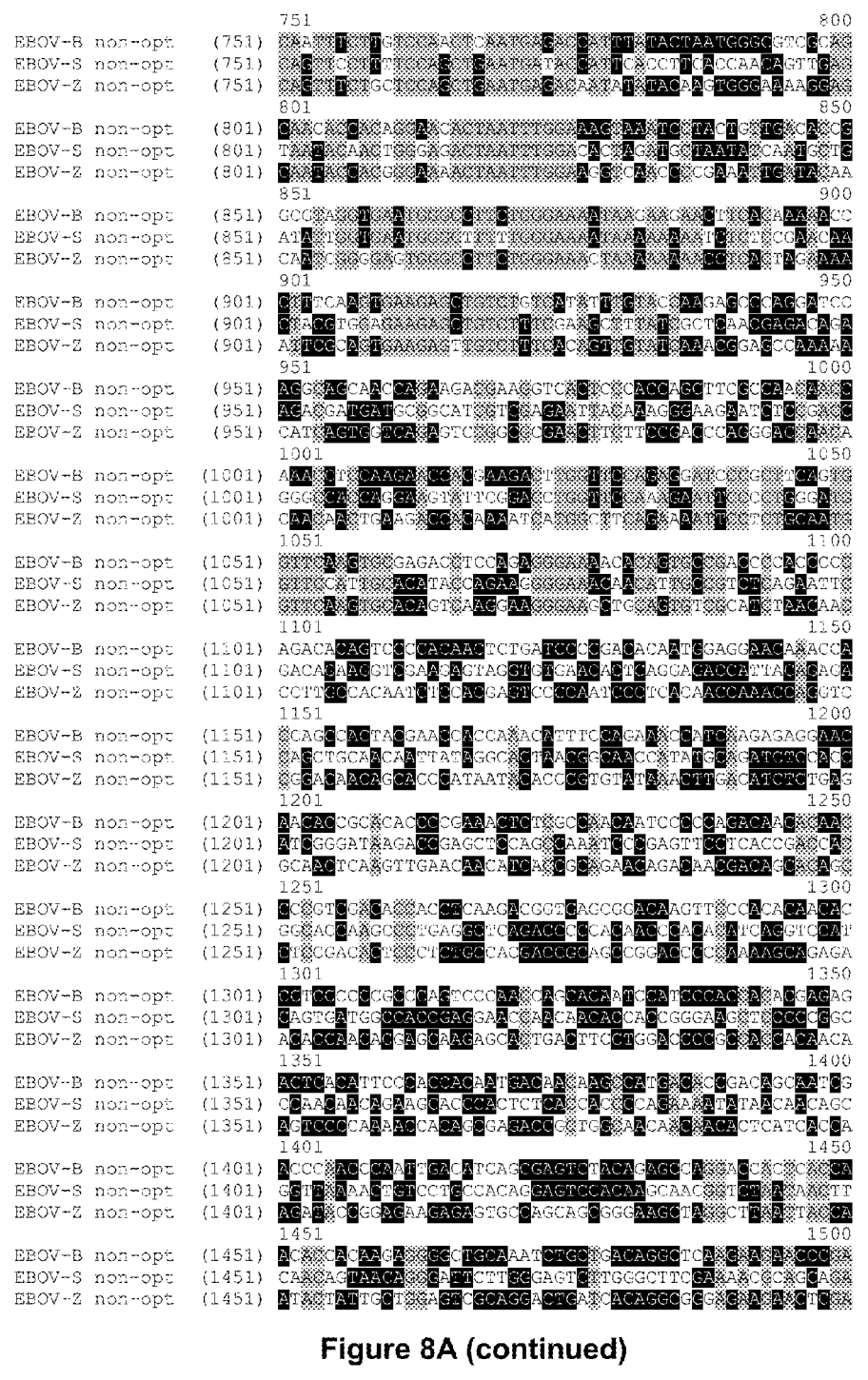
Figure 8A:
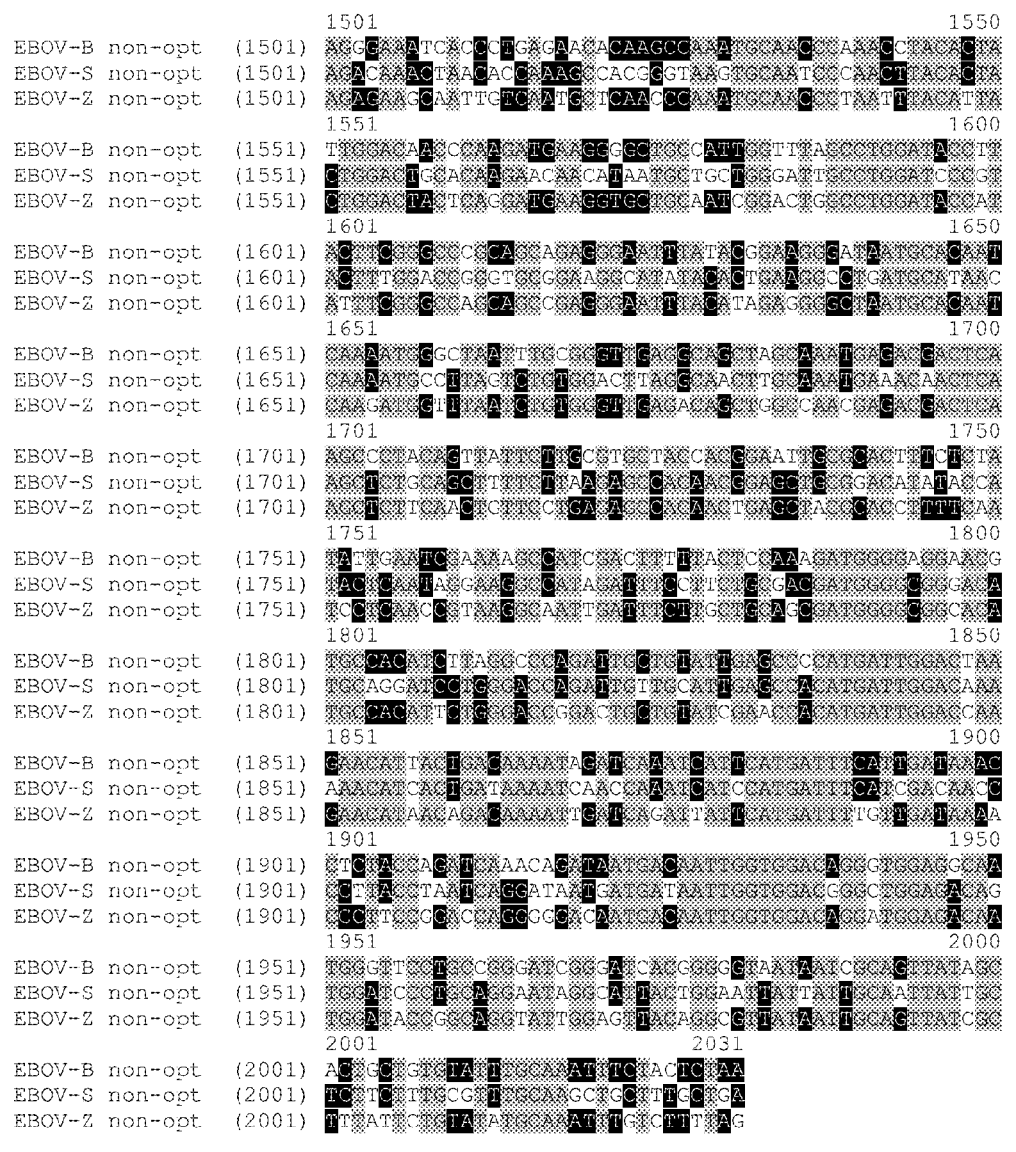
Figure 8B:
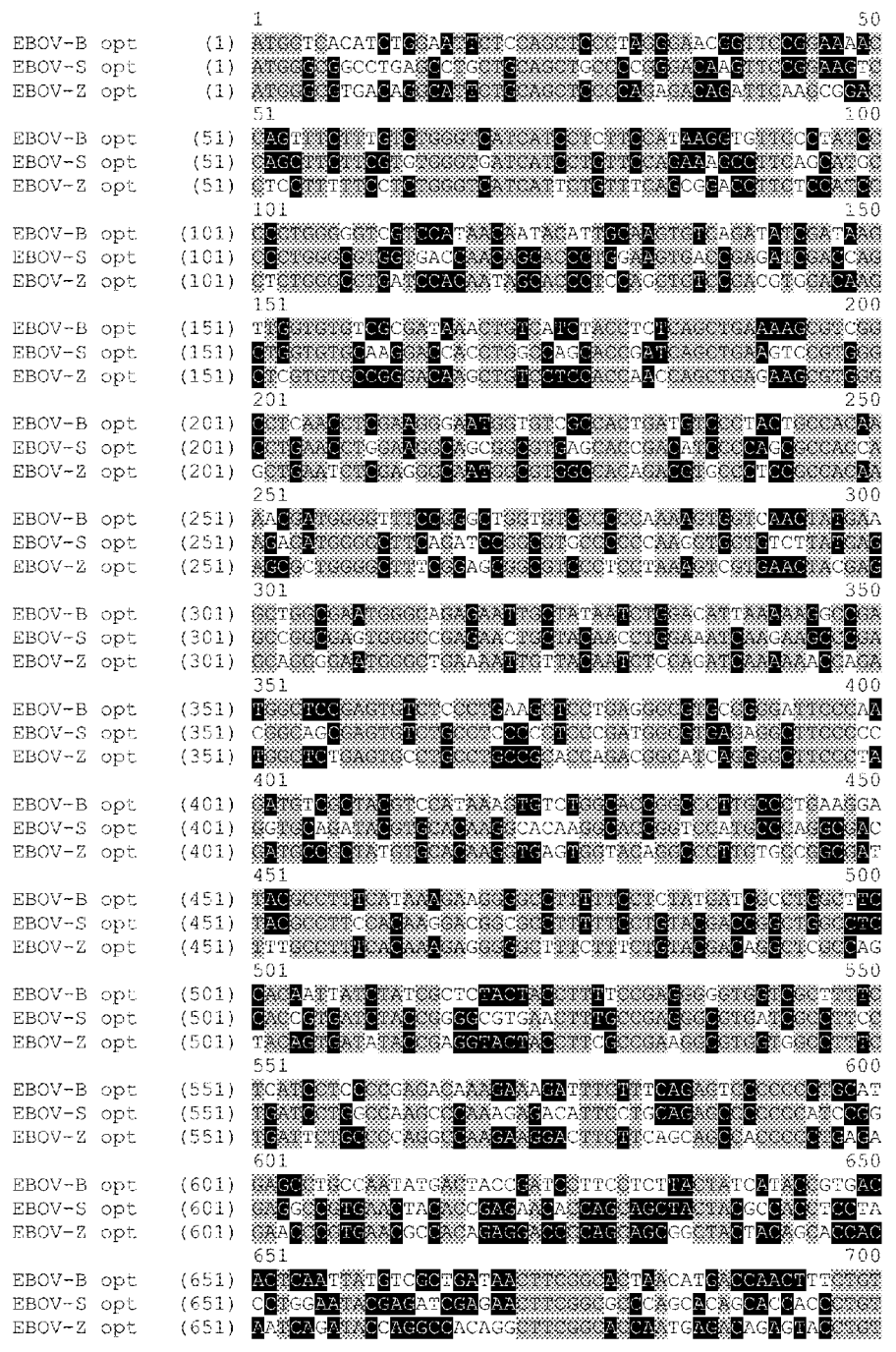
Figure 8B:
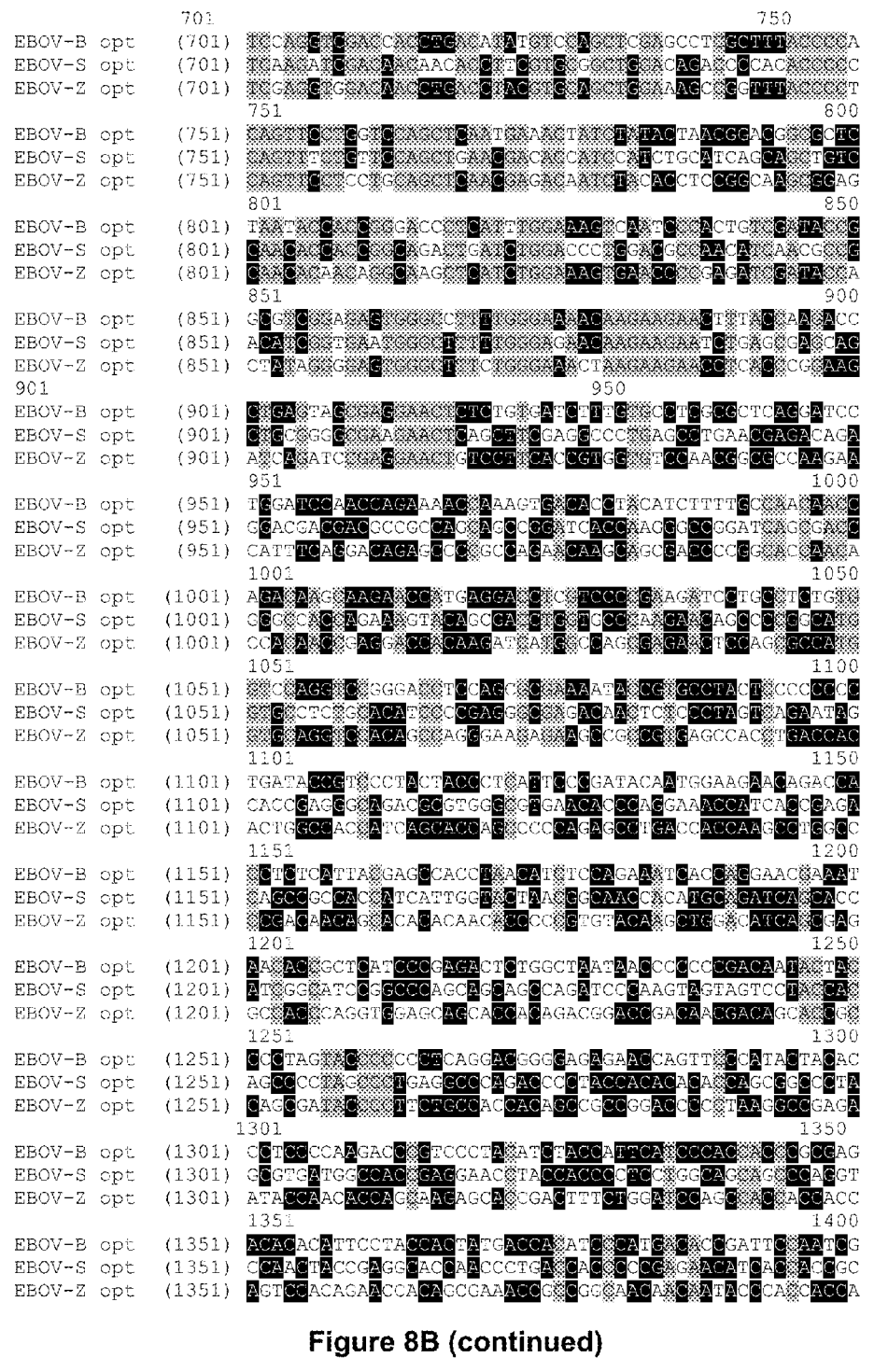
Figure 8B:
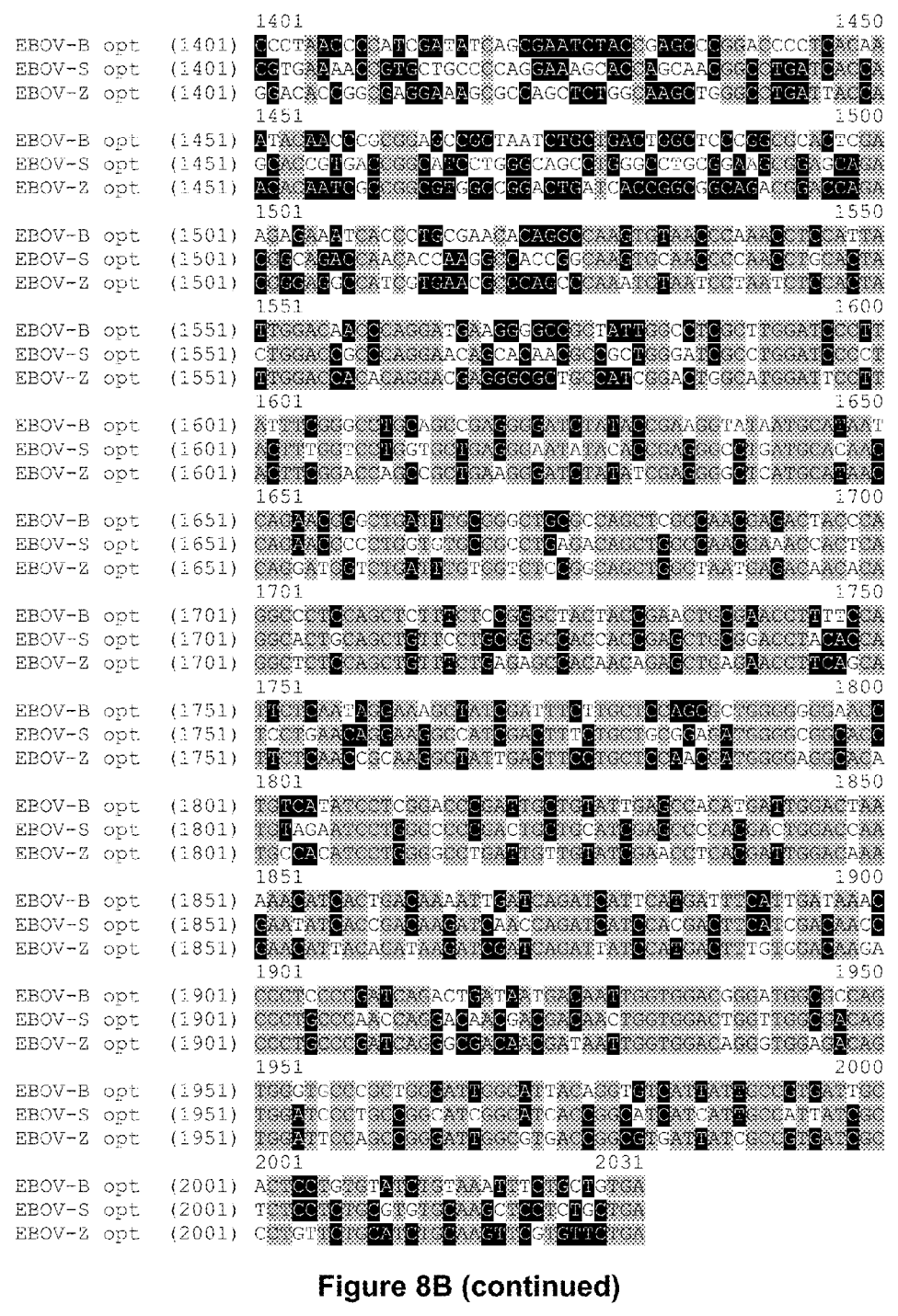

FIGS. 8A and 8B depict an alignment of three EBOV GP coding sequences used in the recombinant MVA-BN® based construct. The coding sequences for the GP genes originating from three EBOV strains EBOV-B (SEQ ID NO: 8), -S (SEQ ID NO: 9) and -Z (SEQ ID NO: 10) were aligned before (non-opt; see FIG. 8A, (SEQ ID NOs:8-10)) and after (opt; see FIG. 8B, (SEQ ID NOs:11-13)) optimization. No gaps were allowed in the alignment. Gray background: identical nucleotide positions in three coding sequences. Black background: identical nucleotide positions in two coding sequences. The identity in nucleotide positions of three genes prior optimization (non-opt) is 45.3%, while after optimization (opt) it is 44.6%.

FIG. 9 depicts pairwise alignments of three EBOV GP coding sequences used in the recombinant MVA-BN® based construct. The coding sequences for the GP genes originating from three EBOV strains EBOV-B, -S and -Z were aligned pairwise before (non-opt; see FIG. 9A, (SEQ ID NOs:8-10)) and after (opt; see FIG. 9B, (SEQ ID NOs:11-13)) optimization. FIG. 9A: EBOV-B non-opt SEQ ID NO: 8, EBOV-S non-opt SEQ ID NO:9, EBOV-Z non-opt SEQ ID NO:10; FIG. 9B: EBOV-B opt SEQ ID NO: 11, EBOV-S opt SEQ ID NO:12, EBOV-Z opt SEQ ID NO:13. No Gaps were allowed in the alignments. Gray background: identical nucleotide positions in the coding sequence. The identity in nucleotide positions of three genes prior (non-opt) and after (opt) optimization is tabulated in Table C.

EXAMPLES

Example 1

Preparation of Substituted, Truncated F Gene

Creation of a recombinant MVA expressing both a full-length RSV-F protein and a truncated Version RSV-F_trunc was desired. However, based on results with MVA and other vaccinia viruses containing repeat sequences, it was expected that intramolecular recombination would lead to recombination between the two copies of the F gene, resulting in deletion of one of the copies of the F gene.

To minimize the presence of long stretches of identical nucleotides between the two F genes, the codons in the nucleotide sequence encoding the RSV-F_trunc gene were substituted, while maintaining the amino acid sequence of the F genes. The use of rare codons for mammals and chickens was avoided. Also, substitutions that might introduce nucleic acid signals were avoided. Such signals included internal TATA-boxes, chi-sites, and ribosomal entry sites; AT-rich and GC-rich sequence stretches; ARE, INS, and CRS sequence elements; repeat sequences and RNA secondary structures; (cryptic) splice donor and acceptor sites, and branch points; and vaccinia termination signals (TTTTTNT). The substituted nucleotide sequence is shown in FIG. 1, compared to a coding sequence for a full-length RSV-F protein. Although significant identity remains throughout the two coding sequences, there are no remaining large stretches of identity greater than nine contiguous nucleotides within the two coding sequences. The proteins encoded by the two coding sequences are aligned in FIG. 2. The two proteins have 100% identity over the first 524 amino acids (the substituted F protein is truncated at the carboxy terminus). Thus, although these two coding nucleotide sequences encode a stretch of identical amino acids, one of the sequences has been substituted relative to the other.

Example 2

Preparation of Recombinant Viruses Comprising RSV-F Genes

The DNA encoding the full-length RSV-F gene was inserted into MVA at two different integration sites to generate MVA-mBN170B and MVA-mBN172B (in the IGR88/89 site). The substituted, RSV-F_trunc gene was inserted into MVA at the IGR148/149 site to generate MVA-mBN173B.

Figure 4A:
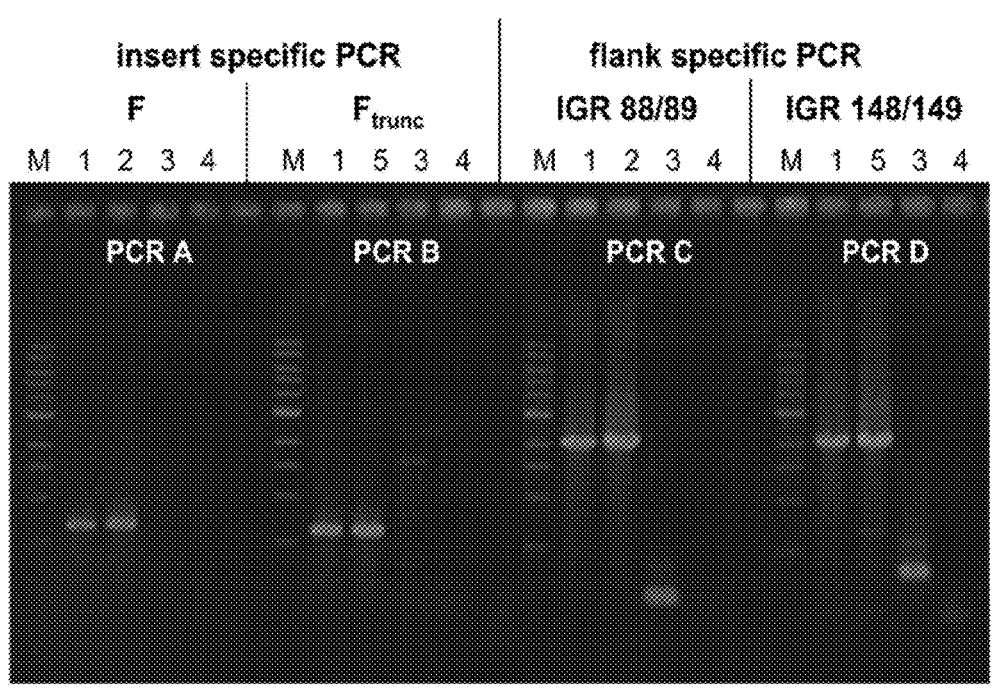
FIGS. 4A-C depict PCR analysis of MVA-mBN175B. RSV-F (F) and RSV-F_trunc (F_trunc) are shown. A. PCR results with various primer pairs. M=markers (1 kb-ladder, New England Biolabs). Lane 1 is MVA-mBN175B. Lane 2 is a positive control plasmid (pBN345). Lane 3 is MVA-mBN®. Lane 4 is a water control. Lane 5 is a positive control plasmid (pBN343). B. Schematic of MVA-mBN175B showing locations of primers used for the PCRs shown in FIG. 4A. C. Schematic of wild type MVA-mBN® showing locations of primers.
Figure 4B:
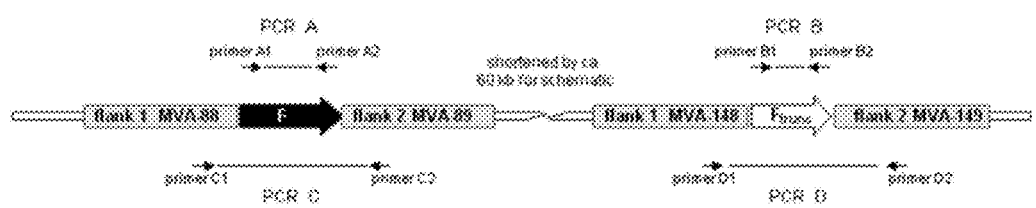
Figure 4C:
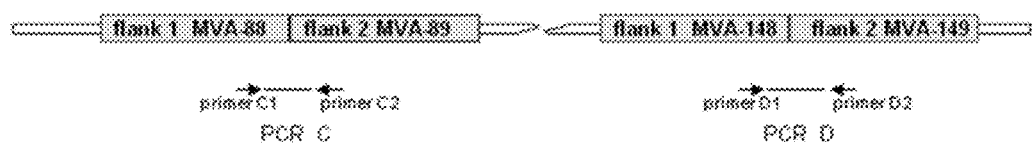

A double recombinant MVA was then created containing the full-length RSV-F gene inserted into MVA at the IGR88/89 site and the substituted, RSV-F_trunc gene inserted into the same MVA at the IGR148/149 site. The double recombinant virus was called MVA-mBN175B. A schematic of this virus is shown in FIG. 4B.

Example 3

Expression of F Proteins from Recombinant Viruses

Figure 3:
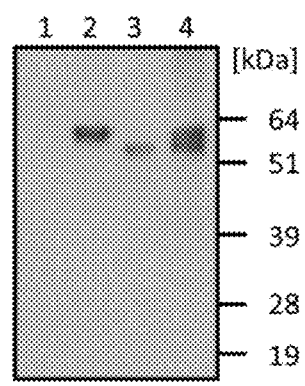
FIG. 3 depicts expression of RSV-F and RSV-F_trunc from recombinant MVA-BN® viruses in a human cell line. Western blot with extracts from infected human cells upon infection with different MVA-BN® based viruses with an MOI of 10 and lysis at 24 h post infection. MVA-BN® (empty vector control; lane 1), MVA-mBN172B (recombinant MVA-BN® with full length RSV-F; lane 2), MVA-mBN173B (recombinant MVA-BN® with truncated RSV-F_trunc; lane 3) and lane 4: MVA-mBN175B (recombinant MVA-BN® with RSV-F and RSV-F_trunc). The calculated molecular weight of the proteins is: RSV-F (61.6 kDa) and RSV-F_trunc (56.1 kDa).

To determine whether protein was expressed from the substituted nucleotide sequence, western blot analysis was performed on protein extracts from a human cell line infected with a recombinant MVA-BN®-based virus encoding the full-length RSV-F gene (MVA-mBN172B), the virus encoding the substituted, RSV-F_trunc gene (MVA-mBN173B) and a double recombinant virus encoding both, the full length and the RSV-F_trunc gene (MVA-mBN175B). All three viruses showed the production of the appropriately sized RSV-F proteins by Western blot analysis (FIG. 3), while the MVA-BN® control (empty vector) did not show any bands, as expected. Thus, the full length and the truncated F protein expressed from the substituted coding nucleotide sequence were expressed individually from single recombinant MVA-BN® but both were also co-expressed from one double recombinant MVA-BN® virus (MVA-mBN175B) in a human cell line.

Example 4

Growth of Recombinant Viruses

Chicken embryo fibroblast cells were infected with MVA-mBN175B, a construct containing both the full-length F gene and the substituted, RSV-F_trunc gene, or a construct containing only the full-length F gene to receive a first virus crude stock. Similar titers of the double recombinant virus containing both full length F and truncated F genes (1.34× $10^7$ TCID50) were seen in comparison with titers of the virus containing only the full length F gene (1.46×$10^7$ TCID50). These results indicated that a stable double recombinant MVA was being produced, and that recombination between the two copies of the F gene had been limited by substituting nucleotide bases in the sequences.

Example 5

PCR Analysis of Recombinant Viruses

PCR analysis was performed on DNA from cells infected with MVA-mBN175B or MVA-BN® using the insert-specific and flank-specific primer pairs depicted in FIGS. 4B and C. PCR A with primers A1/A2, which are specific for the full-length F gene, detected a band with the size of 663 base pairs (bp) in cells infected with MVA-mBN175B and in a specific plasmid positive control as expected. This band as expected is absent in cells infected with MVA-BN® or in the water control (FIG. 4A). PCR B with primers B1/B2, which are specific for the substituted, truncated F gene, detected a band with the size of 625 bp in cells infected with MVA-mBN175B and in a specific plasmid positive control as expected. This band, as expected, is absent in cells infected with MVA-BN® or in the water control (FIG. 4A). PCR C with primers C1/C2, which detect insertions into the IGR88/89 site, detected a band with the size of 2047 bp in cells infected with MVA-mBN175B and in a specific plasmid positive control as expected. This band, as expected, is absent in cells infected with the empty vector control MVA-BN®, instead a band of 161 bp indicates the wildtype situation at IGR88/89 in MVA-BN® (FIG. 4A). PCR D with primers D1/D2, which detect insertions into the IGR148/149 site, detected a band with the size of 2062 bp in cells infected with MVA-mBN175B and in a specific plasmid positive control as expected. This band as expected is absent in cells infected with the empty vector control MVA-BN®, instead a band of 360 bp indicates the wildtype situation at IGR88/89 in MVA-BN®. (FIG. 4A).

Figure 5A:
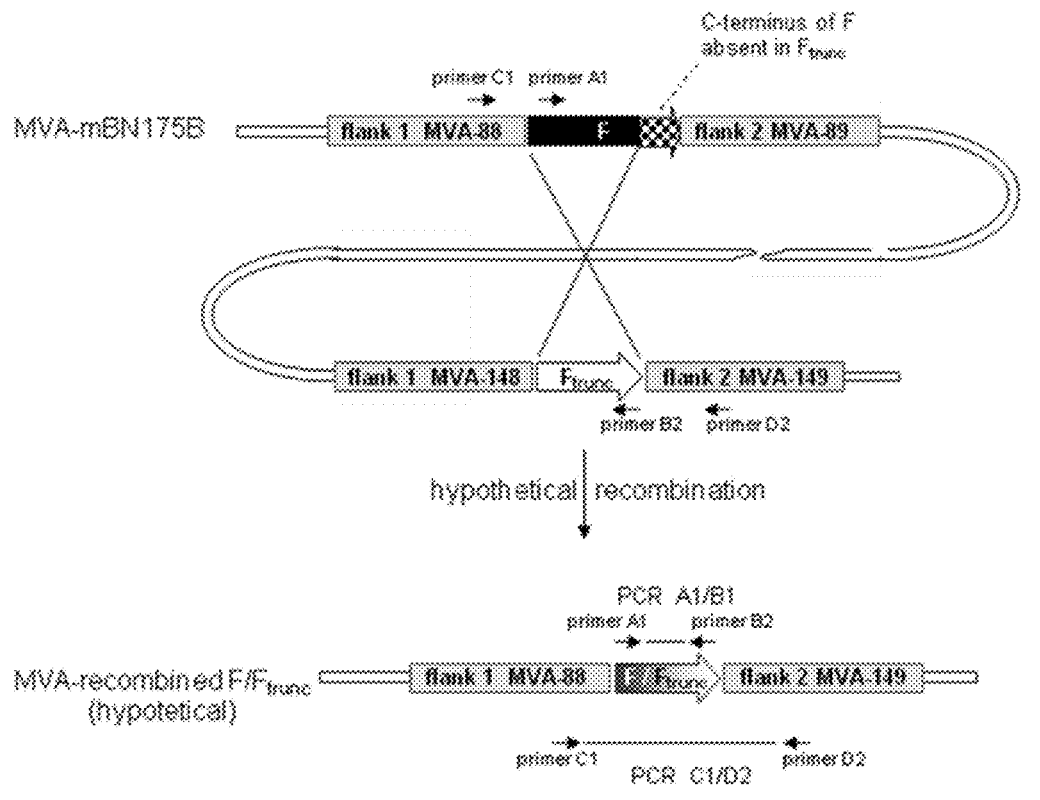
Figure 5B:
Figure 5C:
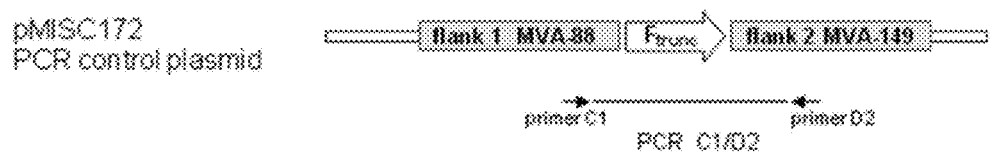
Figure 6:
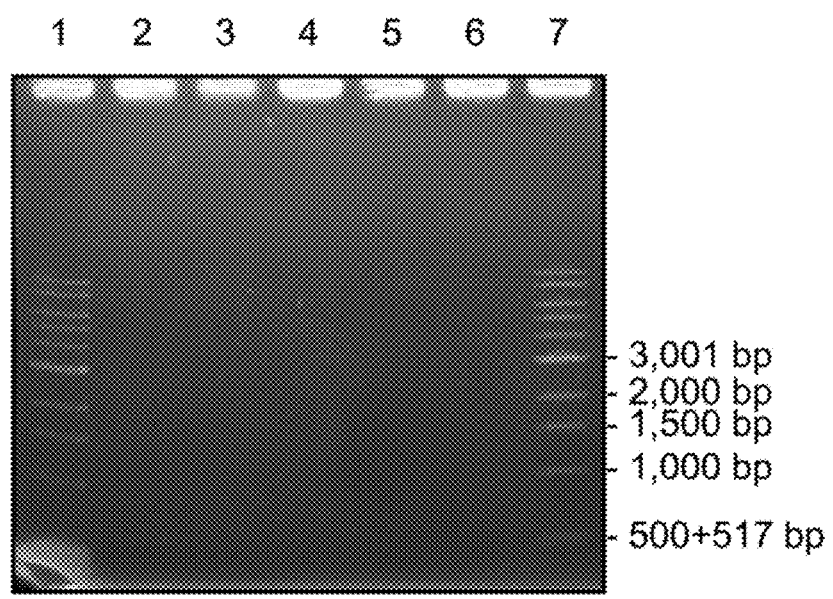
FIG. 6 depicts PCR analysis of DNA isolated from cells infected with MVA-nnBN175B. Lanes 1 and 7 are marker lanes. Lane 2 is MVA-mBN175B. Lane 3 is a plasmid control for the F gene (pBN343). Lane 4 is a plasmid control for the truncated F gene (pBN345). Lane 5 is MVA-BN®. Lane 6 is a water control. The expected PCR product from a hypothetical recombination between the RSV-F gene and truncated F gene RSV-F_trunc in MVA-mBN175B is 613 base pairs.

Recombination between the F genes would yield a hybrid F gene having parts of the wild-type F gene and parts of the truncated F gene. (FIG. 5A.) To detect the presence of any such recombinants, PCR analysis was performed on DNA from cells infected with MVA-mBN175B or MVA-BN® using the primer pairs A1/B2 (FIG. 5B.), which should generate a 613 base pair product, specific for the recombinant F gene. The results of this PCR showed no detectable recombinants. (FIG. 6.) These results indicated that a stable double recombinant MVA was being produced, and that recombination between the two copies of the F gene had been limited.

Example 6

Figure 7:
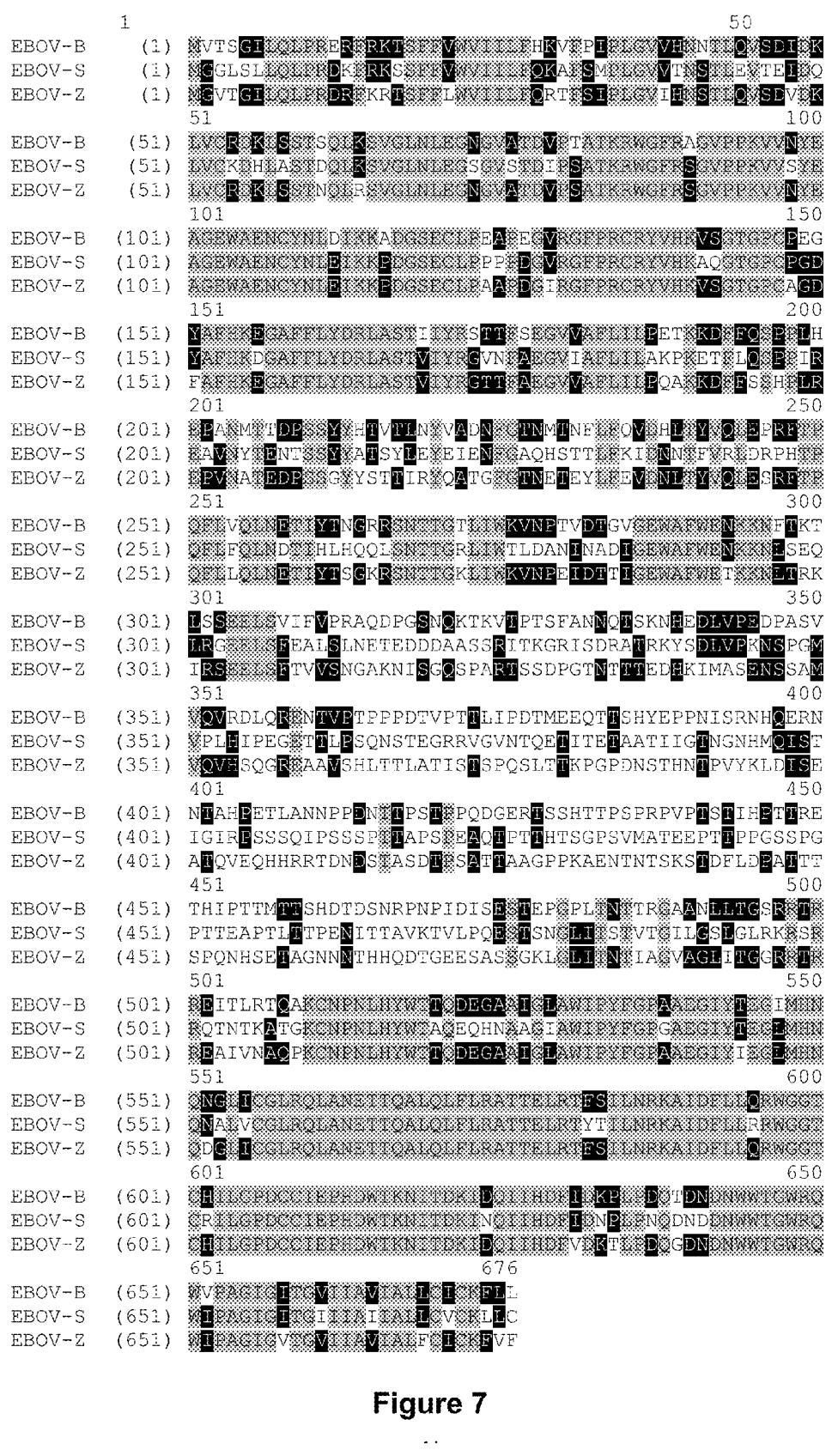

Preparation of Recombinant Glycoprotein (GP) Genes of Three Different Ebolavirus (EBOV) Strains Generation of a recombinant MVA expressing three ebolavirus (EBOV) glycoproteins (GP) was desired. The EBOV strains used herein are EBOV-B (Bundibugyo), EBOV-S (Sudan) and EBOV-Z (Zaire), all belonging to virus strains with high lethality in infected humans. Said three GP share an overall identity of 48.5%, indicating that nearly every second amino acid in the GP proteins is identical in all three strains, while the percent identities over the full-length protein sequences in comparison of combinations of two strains are between 57.0% and 64.2% (FIG. 7).

To minimize the presence of long stretches of identical nucleotides within the three EBOV GP genes, the codons in the three nucleotide sequences were substituted, while maintaining the encoded amino acid sequences of the three GP genes. The use of rare codons for mammals and chickens, as well as substitutions that might introduce nucleic acid signals were avoided. Such signals included internal TATA-boxes, chi-sites, and ribosomal entry sites; AT-rich and GC-rich sequence stretches; ARE, INS, and CRS sequence elements; repeat sequences and RNA secondary structures; (cryptic) splice donor and acceptor sites, and branch points; and vaccinia termination signals (TTTTTNT). The G after the ATG start codon allows for high expression and is present in the original coding sequence of all three EBOV GP genes and was maintained.

Although 23.3 to 24.9% of the nucleotides in each of the 3 optimized EBOV GP coding sequences were exchanged (see Table A), the overall identities did not dramatically change between the three GP coding sequences (Table B). In two cases, the pair wise comparisons even showed marginally higher identities after optimization of the coding sequences, as shown below in Table B.

TABLE A

Nucleotide exchanges in three optimized EBOV GP genes. The table shows the number of changed nucleotides at the corresponding positions in the optimized GP coding sequences (opt) compared to the non-optimized (non-opt) sequence of different EBOV strains based on the total number of nucleotides in [%]. The total number of nt is 1147.

|  | exchanged nt positions in optimized GP coding sequences compared to non-optimized sequences [%] |
|---|---|
| EBOV-B non-opt:EBOV-B opt | 23.3 |
| EBOV-S non-opt:EBOV-S opt | 24.9 |
| EBOV-Z non-opt:EBOV-Z opt | 23.9 |

TABLE B

Identical nucleotide positions of three EBOV GP coding sequences. The table shows the number of identical nucleotides at the corresponding positions in two GP coding sequences of different EBOV strains based on the total number of nucleotides in [%].

| pairwise comparison of GP genes | identity of nucleotides in non-optimized genes [%] | identity of nucleotides in optimized genes [%] |
|---|---|---|
| EBOV-B:EBOV-S | 57.0 | 57.3 |
| EBOV-B:EBOV-Z | 64.2 | 61.1 |
| EBOV-S:EBOV-Z | 57.6 | 60.4 |

Figure 9B:
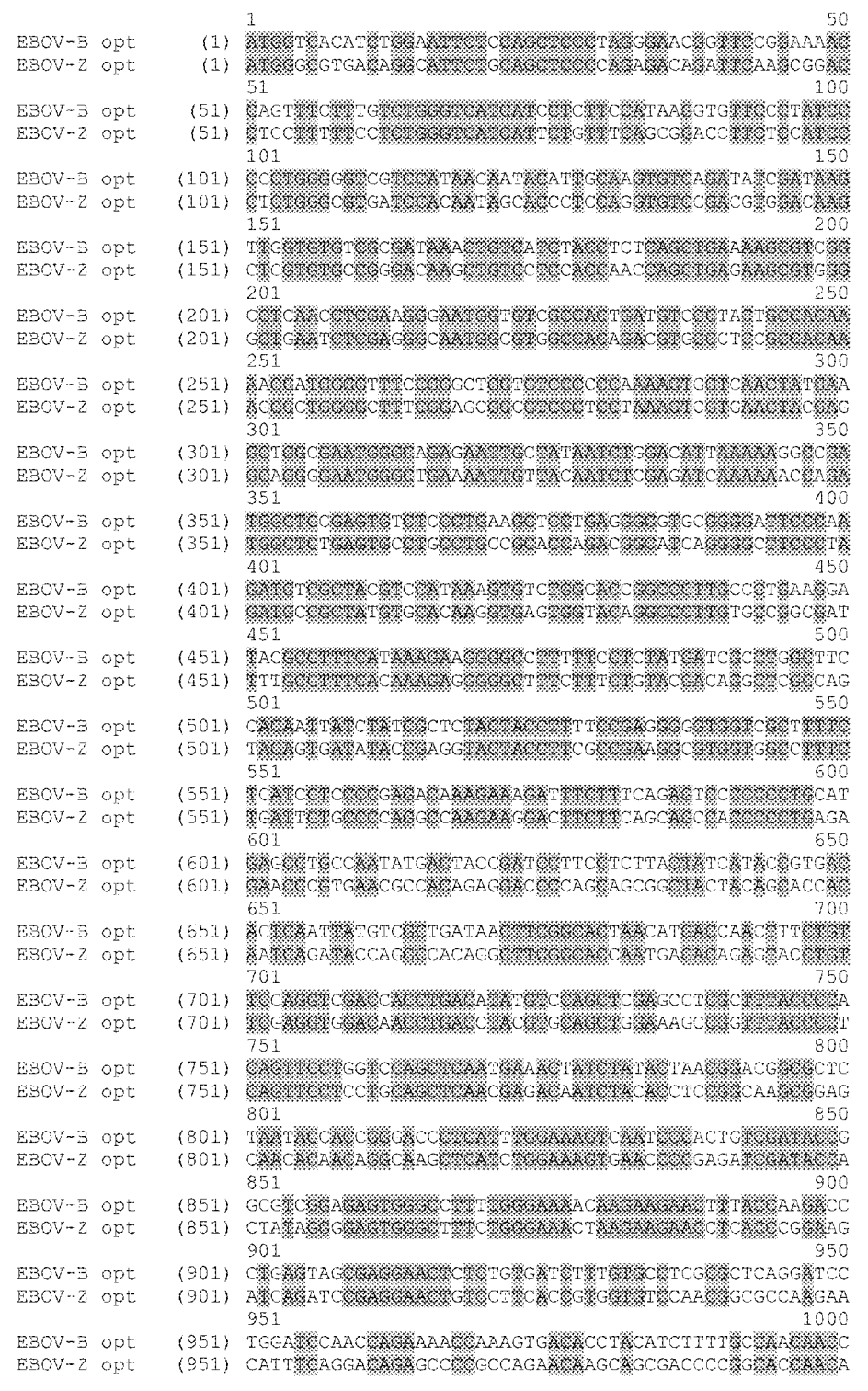
Figure 9B:
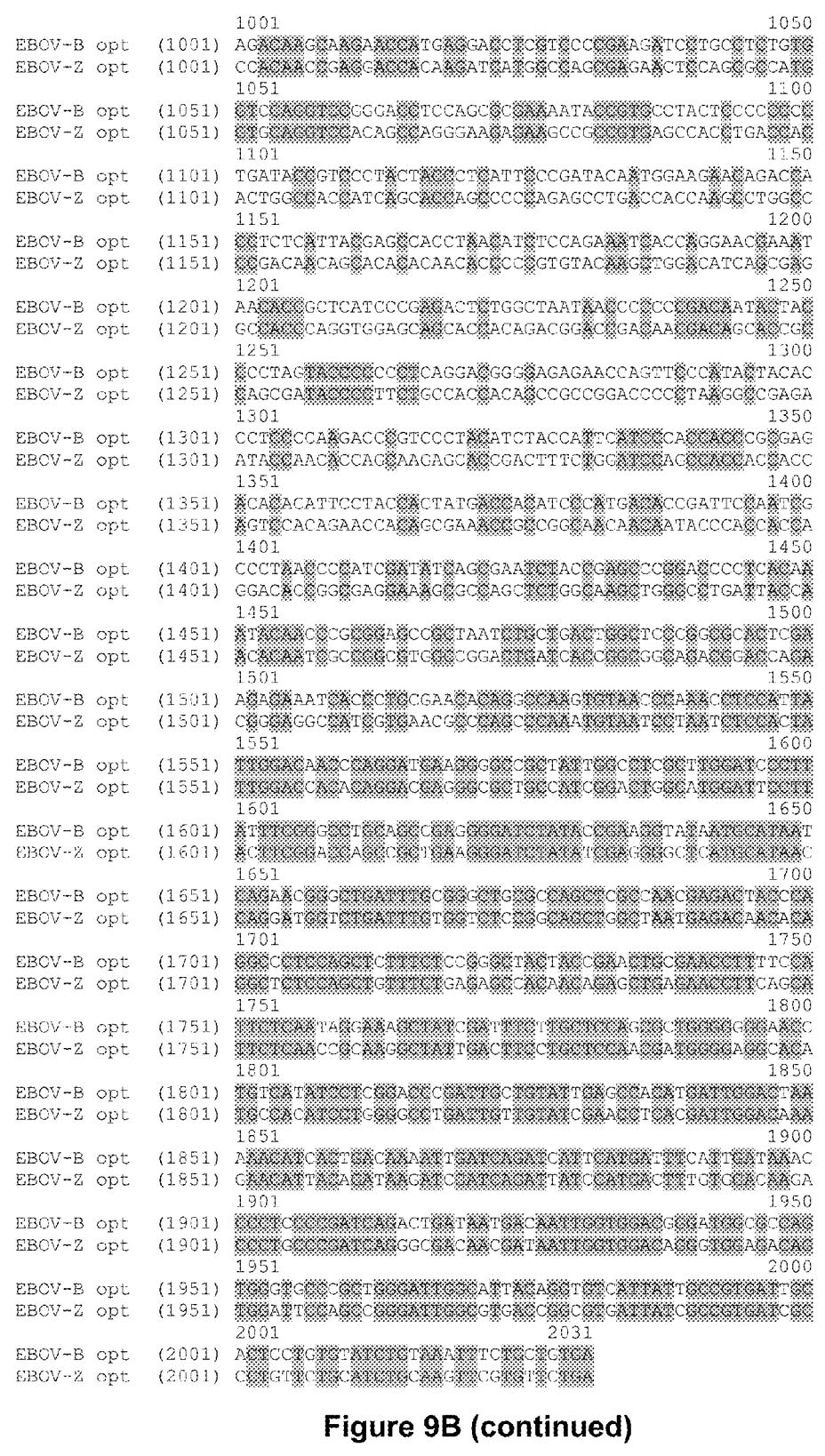
Figure 9B:
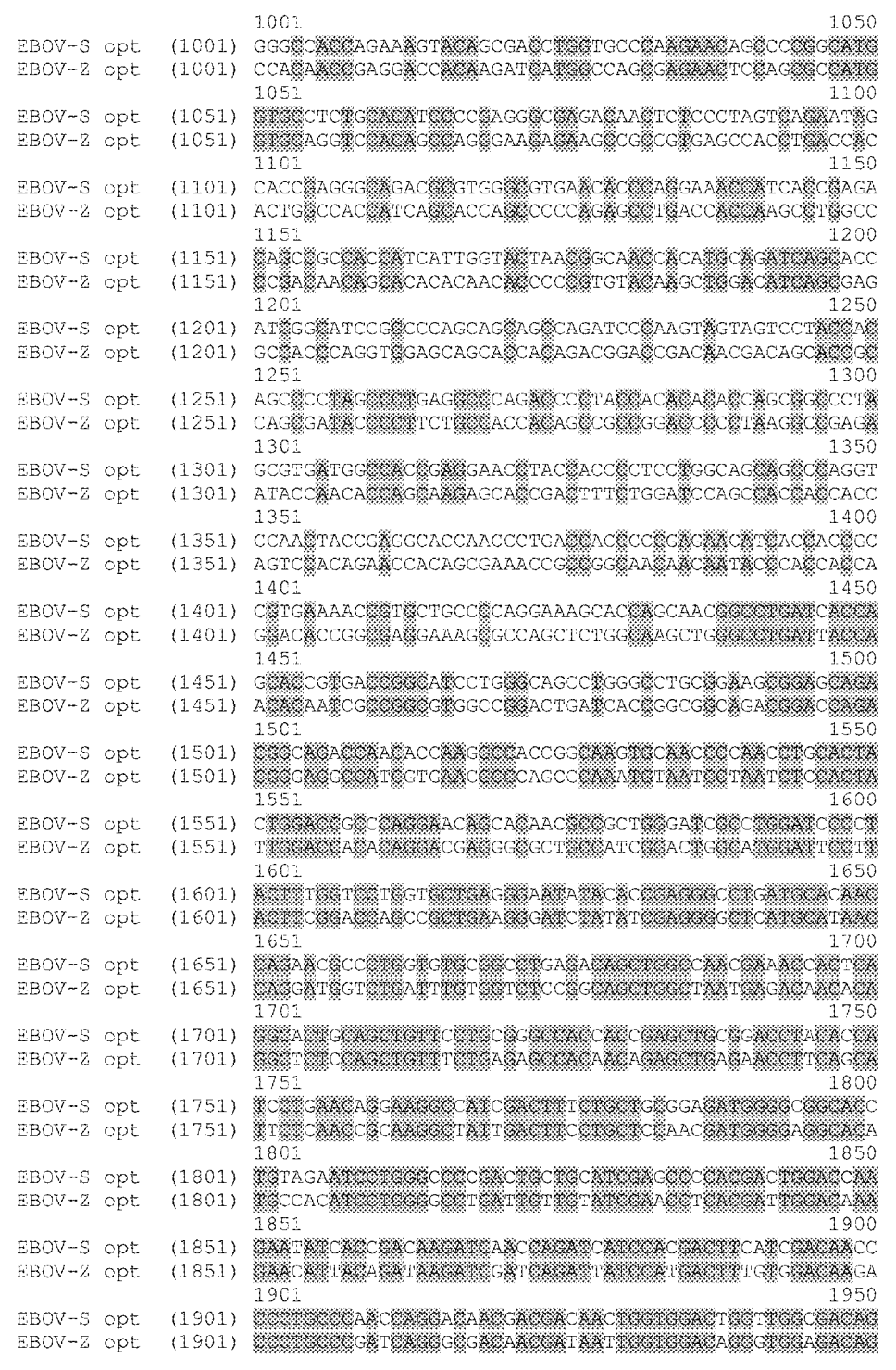

Pairwise alignments of the GP coding sequences of three EBOV strains EBOV-B, -S and -Z showed the identities in nucleotide positions and the distribution of identities (FIGS. 9A and 9B). Consequently, the method of the present invention led to shorter stretches of nucleotide identity in the EBOV GP-sequences. When considering long stretches of identical consecutive nucleotides, it is evident that the interruption or shortening of such stretches of identities is an important part of the strategy to avoid recombination between sequences sharing a certain degree of nucleotide identities. In Table C (see below) the number of stretches of consecutive identical nucleotides from pair wise comparison of the GP coding sequences are shown. Prior to optimization, there are stretches of up to 23 bp length and in summary there are 41 stretches of 10 or more identical nucleotides. In the optimized version of the GP genes, only one 13 bp stretch is found and 7 stretches of 10 or more identical nucleotides can be found.

TABLE C

Long stretches of consecutive identical nucleotides. The table shows the number of stretches of consecutive identical nucleotides of a certain length in pair wise comparison of EBOV GP coding sequences before (non-opt) and after (opt) optimization. The numbers of the pairwise comparisons are summarized in the column 'combined numbers'. The longest stretch in the non-optimized comparisons are 23 consecutive identical nucleotides, while in the optimized genes, it is reduced to a maximum of 13 nucleotides. Only stretches of 10 or more nucleotides are listed.

| | EBOV-B:EBOV-S | | EBOV-B:EBOV-Z | | EBOV-S:EBOV-Z | | combined numbers | |
|---|---|---|---|---|---|---|---|---|
| length | non-opt | opt | non-opt | opt | non-opt | Opt | non-opt | opt |
| 23 nt |  |  | 1 |  |  |  | 1 |  |
| 20 nt |  |  | 2 |  |  |  | 2 |  |
| 17 nt |  |  |  |  | 1 |  | 1 |  |
| 16 nt |  |  | 2 |  |  |  | 2 |  |
| 14 nt |  |  | 2 |  | 2 |  | 4 |  |
| 13 nt |  |  | 1 | 1 | 1 |  | 2 | 1 |
| 12 nt | 1 |  | 2 |  |  |  | 3 |  |
| 11 nt | 10 | 2 | 4 | 1 | 8 |  | 22 | 3 |
| 10 nt | 1 |  | 2 | 1 | 1 | 2 | 4 | 3 |

Example 7

Preparation of Recombinant MVA-BN® Viruses with GP Genes of EBOV Strains

The three EBOV GP genes were synthesized by GeneArt (Regensburg, Germany) and cloned into recombination vectors to allow for integration into MVA-BN®. A recombinant virus comprising the three optimized homologous GP gene sequences from three different EBOV strains was generated. The transcription of the three inserted GP coding sequences is controlled by different individual early-late promoters.

Specific PCR reactions for the three optimized EBOV-GP sequences showed the presence of the three individual genes in the recombinant MVA-BN®.

Example 8

Preparation of Plasmid Comprising RSV-F Genes

Figure 10:
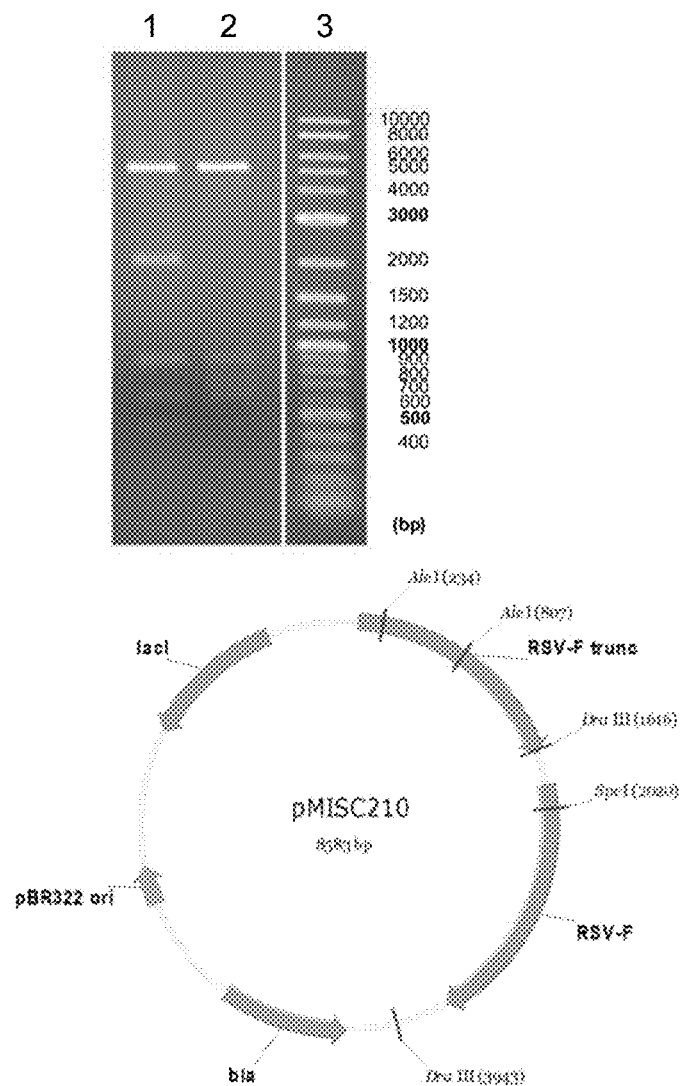
FIG. 10 depicts a restriction enzyme digest and plasmid map of plasmid pMISC210 comprising the full-length (RSV-F) and truncated (RSV-F_trunc) protein. Lane 1: plasmid pMISC210 comprising RSV-F and RSV-F_trunc; Lane 2: control plasmid pMISC209 comprising RSV-F_trunc only; Lane 3: Molecular weight marker. The size of the marker-bands in base pairs (bp) is shown.

The two versions of the RSV-F gene used in examples 1-5 and shown in FIG. 1 were cloned into one plasmid and maintained in *E. coli* TZ101 (Trenzyme GmbH, Konstanz, Germany) using standard cloning techniques. The plasmid (see plasmid map in FIG. 10) was isolated and digested with the restriction enzymes Ale I, Dra III and Spe I and separated on a 1% TAE agarose gel (see FIG. 10). The band patterns for pMISC210 encoding the full-length RSV-F protein and RSV-F_trunc protein (lane 1) as well as the control plasmid pMISC209 encoding the RSV-F_trunc protein only (lane 2) were compared with the patterns expected from the results of analysis of the electronic sequence of the plasmids. The expected size of bands for pMISC210 was 404, 573, 809, 1923 and 4874 bp, while for pMISC209 a pattern of bands with sizes of 573, 661, 809 and 4874 bp was expected. All expected bands and no additional bands were found experimentally. In case recombination between the RSV-F variants in pMISC210 occurred, one or more of the smaller fragments would be lost, depending on the sites of recombination. This was clearly not found in the current example. Thus, the results show the stability of the plasmid pMISC210 with the two RSV-F genes (RSV-F and RSV-F_trunc) in *E. coli*.

The invention claimed is:

1. A method for generating a stable modified vaccinia Ankara (MVA) virus vector comprising:
   providing a vector or vectors containing two nucleotide sequences of at least 2000 nucleotides each, wherein each nucleotide sequence encodes a single Ebola virus glycoprotein;
   substituting at least 400 nucleotides in one or both of the nucleotide sequence(s) to generate two divergent sequences;
   wherein the 400 substituted nucleotides do not alter the amino acids encoded by the two divergent sequences; and
   generating a stable MVA vector comprising the two divergent sequences stably inserted into the MVA genome,
   wherein the two divergent sequences share stretches of identity of no more than 10 contiguous nucleotides; and
   wherein the two nucleotide sequences encode Ebola virus Sudan and Ebola virus Zaire glycoproteins.

2. The method of claim 1, wherein the substitutions increase the overall nucleotide identity between the two nucleotide sequences.

3. The method of claim 1, wherein the two divergent sequences comprise the nucleotide sequences of SEQ ID NO:12 and SEQ ID NO:13.

4. A method for generating a stable modified vaccinia Ankara (MVA) virus vector comprising:
provide two nucleotide sequences of at least 2000 nucleotides each, wherein each nucleotide sequence encodes a single Ebola virus glycoprotein;
substituting at least 400 nucleotides in one or both of the nucleotide sequence(s) to generate two divergent sequences;
wherein the 400 substituted nucleotides do not alter the amino acids encoded by the two divergent sequences; and
generating a stable MVA vector comprising the two divergent sequences stably inserted into the MVA genome,
wherein the two divergent sequences share stretches of identity of no more than 10 contiguous nucleotides; and
wherein the two nucleotide sequences encode Ebola virus Sudan and Ebola virus Zaire glycoproteins.

5. The method of claim 4, wherein the substitutions increase the overall nucleotide identity between the two nucleotide sequences.

6. The method of claim 4, wherein the two divergent sequences comprise the nucleotide sequences of SEQ ID NO:12 and SEQ ID NO:13.

7. A method for generating a stable modified vaccinia Ankara (MVA) virus vector comprising:
providing first and second nucleotide sequences of at least 2000 nucleotides each,
wherein each nucleotide sequence encodes a single Ebola virus glycoprotein,
wherein one of the two nucleotide sequences is a substituted nucleotide sequence, having at least 400 substituted nucleotides different from the other nucleotide sequence,
wherein the substituted nucleotides do not alter the amino acids encoded by the first and second nucleotide sequences,
and wherein the two nucleotide sequences share stretches of identity of no more than 10 contiguous nucleotides; and
inserting the first and second nucleotide sequences into an MVA vector to generate a stable MVA vector,
wherein the two nucleotide sequences encode Ebola virus Sudan and Ebola virus Zaire glycoproteins.

8. The method of claim 7, wherein the first and second nucleotide sequences comprise the sequences of SEQ ID NO:12 and SEQ ID NO:13.

* * * * *